(12) United States Patent
Steinberg

(10) Patent No.: US 7,758,653 B2
(45) Date of Patent: Jul. 20, 2010

(54) IMPLANTS

(75) Inventor: Amiram Steinberg, Avihail (IL)

(73) Assignee: Active Implants Corporation, Memphis, TN (US)

( * ) Notice: Subject to any disclaimer, the term of this patent is extended or adjusted under 35 U.S.C. 154(b) by 1009 days.

(21) Appl. No.: 10/515,486

(22) PCT Filed: May 21, 2003

(86) PCT No.: PCT/IL03/00416

§ 371 (c)(1),
(2), (4) Date: Jul. 1, 2006

(87) PCT Pub. No.: WO03/009156

PCT Pub. Date: Dec. 4, 2003

(65) Prior Publication Data

US 2005/0202371 A1    Sep. 15, 2005

Related U.S. Application Data

(60) Provisional application No. 60/383,483, filed on May 23, 2002.

(30) Foreign Application Priority Data

Dec. 3, 2002    (WO) .................. PCT/IL02/00972

(51) Int. Cl.
*A61F 2/28* (2006.01)
(52) U.S. Cl. ................. 623/23.5; 623/23.44; 623/22.19
(58) Field of Classification Search ............... 623/22.16, 623/22.11, 22.15, 22.17, 23.5, 23.51, 20.28, 623/20.3, 20.21, 22.19, 23.44, 20.15, 23.43; 433/201.1
See application file for complete search history.

(56) References Cited

U.S. PATENT DOCUMENTS

| | | | |
|---|---|---|---|
| 2,765,787 | A | 9/1954 | Pellet |
| 3,576,133 | A | 4/1971 | Krupick et al |
| 3,600,718 | A | 8/1971 | Boone |
| 3,875,594 | A | 4/1975 | Swanson |
| 3,879,767 | A | 4/1975 | Subtad |
| 3,938,198 | A | 2/1976 | Kahn et al. |
| 4,089,071 | A | 5/1978 | Kalnberz et al. |
| 4,195,409 | A | 4/1980 | Child |

(Continued)

FOREIGN PATENT DOCUMENTS

DE    923 383 C    2/1955

(Continued)

OTHER PUBLICATIONS

Stanford C. et al. May 1999 Journal of Prosthetic Dentistry, vol. 81, No. 5 pp. 553-561."Toward the understanding of implant occlusion and strain adaptive bone modeling and remodeling".

(Continued)

*Primary Examiner*—Pedro Philogene
(74) *Attorney, Agent, or Firm*—Haynes and Boone LLP

(57) ABSTRACT

An implantable prosthesis including at least one element defining a bone-engaging surface, the bone-engaging surface including an anchoring mechanism operative for enhancing anchoring and adhesion of the joint defining element to the bone and thus improving the stability and longevity of the prosthesis.

29 Claims, 17 Drawing Sheets

U.S. PATENT DOCUMENTS

| | | | |
|---|---|---|---|
| 4,279,041 A | 7/1981 | Buholtz | |
| 4,292,695 A | 10/1981 | Koeneman | |
| 4,344,193 A | 8/1982 | Kenny | |
| 4,433,440 A | 2/1984 | Coher | |
| 4,570,270 A | 2/1986 | Oechsle, III | |
| 4,624,674 A | 11/1986 | Pappas et al. | |
| 4,650,491 A | 3/1987 | Parchinski | |
| 4,661,112 A | 4/1987 | Muller | |
| 4,662,889 A | 5/1987 | Zicher et al. | |
| 4,715,859 A | 12/1987 | Schlehas et al. | |
| 4,735,625 A | 4/1988 | Davidson | |
| 4,795,470 A | 1/1989 | Goymann et al. | |
| 4,795,474 A | 1/1989 | Horvath | |
| 4,808,186 A | 2/1989 | Smith | |
| 4,813,962 A | 3/1989 | Deckner et al. | |
| 4,822,365 A | 4/1989 | Walker et al. | |
| 4,883,490 A * | 11/1989 | Oh | 623/22.39 |
| 4,888,020 A | 12/1989 | Horber | |
| 4,892,551 A | 1/1990 | Haber | |
| 4,904,269 A | 2/1990 | Elloy et al. | |
| 4,908,035 A | 3/1990 | Deckner et al. | |
| 4,919,674 A | 4/1990 | Schelhas | |
| 4,919,678 A | 4/1990 | Kranz | |
| 4,936,856 A | 6/1990 | Keller | |
| 4,938,771 A | 7/1990 | Vecsei et al. | |
| 4,938,773 A | 7/1990 | Strand | |
| 4,950,298 A | 8/1990 | Gustilo et al. | |
| 4,955,912 A | 9/1990 | Berchem | |
| 4,955,919 A | 9/1990 | Pappas et al. | |
| 4,963,153 A | 10/1990 | Noes Berger et al. | |
| 4,963,154 A | 10/1990 | Anapliotis et al. | |
| 4,997,444 A | 3/1991 | Farling | |
| 4,997,447 A | 3/1991 | Shelley | |
| 5,002,579 A | 3/1991 | Copf et al. | |
| 5,002,581 A | 3/1991 | Paxson et al. | |
| 5,011,497 A | 4/1991 | Persson et al. | |
| 5,019,107 A | 5/1991 | Schelhas | |
| 5,026,280 A | 6/1991 | Duerr et al. | |
| 5,032,134 A | 7/1991 | Lindwer | |
| 5,041,140 A | 8/1991 | Teinturies | |
| 5,049,393 A | 9/1991 | Noon et al. | |
| 5,080,675 A | 1/1992 | Lawes et al. | |
| 5,080,677 A | 1/1992 | Shelley | |
| 5,080,678 A | 1/1992 | Spotorno et al. | |
| 5,108,446 A | 4/1992 | Wagner et al. | |
| 5,108,449 A | 4/1992 | Gray | |
| 5,108,451 A | 4/1992 | Forte | |
| 5,116,374 A | 5/1992 | Stone | |
| 5,133,762 A | 7/1992 | Branmark | |
| 5,133,763 A | 7/1992 | Mullers | |
| 5,146,933 A | 9/1992 | Boyd | |
| 5,147,406 A | 9/1992 | Houston et al. | |
| 5,151,521 A | 9/1992 | Morita et al. | |
| 5,156,631 A | 10/1992 | Merletee | |
| 5,171,276 A | 12/1992 | Casperi et al. | |
| 5,181,925 A | 1/1993 | Houston et al. | |
| 5,181,929 A | 1/1993 | Prats et al. | |
| 5,197,987 A | 3/1993 | Koch et al. | |
| 5,197,989 A | 3/1993 | Hinckfuss et al. | |
| 5,201,881 A | 4/1993 | Evans | |
| 5,201,882 A | 4/1993 | Paxson | |
| 5,211,666 A | 5/1993 | Fetto | |
| 5,217,498 A | 6/1993 | Henssge et al. | |
| 5,217,499 A | 6/1993 | Shelley | |
| 5,222,985 A | 6/1993 | Homsy | |
| 5,244,459 A | 9/1993 | Hill | |
| 5,246,461 A | 9/1993 | Tepic | |
| 5,281,226 A | 1/1994 | Davydov et al. | |
| 5,282,868 A | 2/1994 | Bahler | |
| 5,290,314 A | 3/1994 | Koch et al. | |
| 5,314,478 A | 5/1994 | Oka et al. | |
| 5,314,492 A | 5/1994 | Hamilton et al. | |
| 5,314,493 A | 5/1994 | Mikhail | |
| 5,314,494 A | 5/1994 | Huiskes et al. | |
| 5,316,550 A | 5/1994 | Forte | |
| 5,323,765 A | 6/1994 | Brown | |
| 5,326,376 A | 7/1994 | Warner et al. | |
| 5,330,534 A | 7/1994 | Herrington et al. | |
| 5,336,268 A | 8/1994 | Rispeter | |
| 5,344,459 A | 9/1994 | Swartz | |
| 5,358,525 A | 10/1994 | Fox et al. | |
| 5,364,839 A | 11/1994 | Gerhart et al. | |
| 5,370,699 A | 12/1994 | Hood et al. | |
| 5,373,621 A | 12/1994 | Ducheyne et al. | |
| 5,376,064 A | 12/1994 | Cerny | |
| 5,376,120 A | 12/1994 | Sarver et al. | |
| 5,376,123 A | 12/1994 | Klaue et al. | |
| 5,376,125 A | 12/1994 | Winkler | |
| 5,376,126 A | 12/1994 | Lin | |
| 5,387,244 A | 2/1995 | Breard | |
| 5,389,107 A | 2/1995 | Nassar et al. | |
| 5,393,739 A | 2/1995 | Bentz et al. | |
| 5,397,359 A | 3/1995 | Mittelmeier et al. | |
| 5,405,394 A | 4/1995 | Davidson | |
| 5,405,403 A | 4/1995 | Mikhail | |
| 5,405,411 A | 4/1995 | McCoy | |
| 5,413,610 A | 5/1995 | Amino et al. | |
| 5,415,662 A | 5/1995 | Ferrante et al. | |
| 5,425,779 A | 6/1995 | Schlosser et al. | |
| 5,433,750 A | 7/1995 | Gradinger et al. | |
| 5,443,383 A | 8/1995 | Kuehn | |
| 5,443,512 A | 8/1995 | Parr et al. | |
| 5,448,489 A | 9/1995 | Reuben | |
| 5,458,643 A | 10/1995 | Oka et al. | |
| 5,458,651 A | 10/1995 | Lawes | |
| 5,480,437 A | 1/1996 | Drafnert | |
| 5,480,449 A | 1/1996 | Hamilton et al. | |
| 5,489,311 A | 2/1996 | Cippoletti | |
| 5,491,882 A | 2/1996 | Walston et al. | |
| 5,496,375 A | 3/1996 | Sisik et al. | |
| 5,507,814 A | 4/1996 | Gilbert et al. | |
| 5,507,817 A | 4/1996 | Craig et al. | |
| 5,507,818 A | 4/1996 | McLaughlin | |
| 5,507,820 A | 4/1996 | Pappas | |
| 5,507,823 A | 4/1996 | Walston et al. | |
| 5,507,829 A | 4/1996 | Thongspreda et al. | |
| 5,507,830 A | 4/1996 | DeMane et al. | |
| 5,507,832 A | 4/1996 | Michielli et al. | |
| 5,507,833 A | 4/1996 | Bohn | |
| 5,507,834 A | 4/1996 | Laghi | |
| 5,507,835 A | 4/1996 | Jore | |
| 5,507,836 A | 4/1996 | Pohling | |
| 5,510,418 A | 4/1996 | Rhee et al. | |
| 5,514,182 A | 5/1996 | Shea | |
| 5,514,184 A | 5/1996 | Doi et al. | |
| 5,522,894 A | 6/1996 | Draenert | |
| 5,522,904 A | 6/1996 | Moran et al. | |
| 5,549,700 A * | 8/1996 | Graham et al. | 623/22.14 |
| 5,641,323 A | 6/1997 | Caldarise | |
| 5,658,345 A | 8/1997 | Willi | |
| 5,660,225 A | 8/1997 | Saffran | |
| 5,743,918 A | 4/1998 | Calandruccio et al. | |
| 5,755,799 A | 5/1998 | Oehy et al. | |
| 5,755,801 A | 5/1998 | Walker et al. | |
| 5,755,804 A | 5/1998 | Schmotzer et al. | |
| 5,755,810 A | 5/1998 | Cunningham | |
| 5,755,811 A | 5/1998 | Tanamal et al. | |
| 5,766,257 A | 6/1998 | Goodman et al. | |
| 5,766,260 A | 6/1998 | Whiteside | |
| 5,776,202 A | 7/1998 | Copf et al. | |
| 5,782,925 A | 7/1998 | Collazo et al. | |
| 5,782,928 A | 7/1998 | Ries et al. | |
| 5,788,704 A | 8/1998 | Timperley | |
| 5,800,553 A | 9/1998 | Albrektsson et al. | |

| Patent | Date | Name |
|---|---|---|
| 5,800,554 A | 9/1998 | Scholz |
| 5,800,555 A | 9/1998 | Gray, III |
| 5,800,557 A | 9/1998 | Elhami |
| 5,800,558 A | 9/1998 | LaHaise, Sr. |
| 5,800,560 A | 9/1998 | Drafnert |
| 5,824,079 A | 10/1998 | Siegler et al. |
| 5,824,098 A | 10/1998 | Stein |
| 5,824,101 A | 10/1998 | Pappas |
| 5,824,102 A | 10/1998 | Buscayret |
| 5,824,103 A | 10/1998 | Williams |
| 5,824,107 A | 10/1998 | Tscherren |
| 5,824,108 A | 10/1998 | Hubner |
| 5,871,547 A | 2/1999 | Abouaf et al. |
| 5,871,548 A | 2/1999 | Sanders et al. |
| 5,879,387 A | 3/1999 | Jones et al. |
| 5,879,390 A | 3/1999 | Kubein-Meesenburg et al. |
| 5,879,392 A | 3/1999 | McMinn |
| 5,879,393 A | 3/1999 | Whiteside et al. |
| 5,879,395 A | 3/1999 | Tornier et al. |
| 5,879,396 A | 3/1999 | Walston et al. |
| 5,879,397 A | 3/1999 | Kalberer et al. |
| 5,879,398 A | 3/1999 | Swarts et al. |
| 5,879,401 A | 3/1999 | Besemer et al. |
| 5,879,402 A | 3/1999 | Lawes et al. |
| 5,879,404 A | 3/1999 | Bateman et al. |
| 5,879,405 A | 3/1999 | Ries et al. |
| 5,879,407 A | 3/1999 | Waggoner |
| 5,882,206 A | 3/1999 | Gillio |
| 5,888,204 A | 3/1999 | Ralph et al. |
| 5,902,340 A | 5/1999 | White et al. |
| 5,904,688 A | 5/1999 | Gilbert et al. |
| 5,904,720 A | 5/1999 | Farrar et al. |
| 5,906,210 A | 5/1999 | Herbert |
| 5,906,643 A | 5/1999 | Walker |
| 5,906,644 A | 5/1999 | Powell |
| 5,910,171 A | 6/1999 | Kummer et al. |
| 5,910,172 A | 6/1999 | Penenberg |
| 5,911,758 A | 6/1999 | Oehy et al. |
| 5,911,759 A | 6/1999 | Rogala |
| 5,913,858 A | 6/1999 | Calandruccio et al. |
| 5,916,268 A | 6/1999 | Schollner et al. |
| 5,916,269 A | 6/1999 | Serbousek et al. |
| 5,916,270 A | 6/1999 | Lipman |
| 5,919,236 A | 7/1999 | Pfaff et al. |
| 5,928,285 A | 7/1999 | Bigliani et al. |
| 5,928,286 A | 7/1999 | Ashby et al. |
| 5,928,287 A | 7/1999 | Keller |
| 5,928,288 A | 7/1999 | Wilson |
| 5,928,289 A | 7/1999 | Deckner |
| 5,931,870 A | 8/1999 | Cucker et al. |
| 5,931,871 A | 8/1999 | Baur et al. |
| 5,935,171 A | 8/1999 | Schnider et al. |
| 5,935,172 A | 8/1999 | Ochoa et al. |
| 5,935,173 A | 8/1999 | Roger et al. |
| 5,935,174 A | 8/1999 | Dye |
| 5,935,175 A | 8/1999 | Ostiguy, Jr. et al. |
| 5,938,702 A | 8/1999 | Lopez et al. |
| 5,944,756 A | 8/1999 | Fischetti et al. |
| 5,944,757 A | 8/1999 | Grammont |
| 5,944,758 A | 8/1999 | Mansat et al. |
| 5,944,759 A | 8/1999 | Link |
| 7,402,177 B2 * | 7/2008 | Jones et al. ............... 623/22.39 |

FOREIGN PATENT DOCUMENTS

| | | |
|---|---|---|
| DE | 2 247 721 | 4/1974 |
| EP | 0 066092 | 12/1982 |
| EP | 0 190 446 | 8/1986 |
| EP | 0 253 941 | 1/1988 |
| EP | 0 308 081 | 3/1989 |
| EP | 0 698 382 | 2/1996 |
| EP | 1 208 819 | 5/2002 |
| GB | 2 069 338 | 8/1981 |
| GB | 2 126 096 | 3/1984 |
| WO | WO 92/17127 A | 10/1992 |
| WO | WO 97/10776 A | 3/1997 |
| WO | WO 97/41809 A | 11/1997 |
| WO | WO 03/099156 A2 | 12/2003 |

OTHER PUBLICATIONS

Binderman I. et al. Calcified Tissue International 1988; 42, pp. 261-267.

Yasui N. et al.: J Bone Joint Surg. 1997; 79B: pp. 824-830.

International Search Report PCT/IL03/00416 dated Feb. 12, 2004.

* cited by examiner

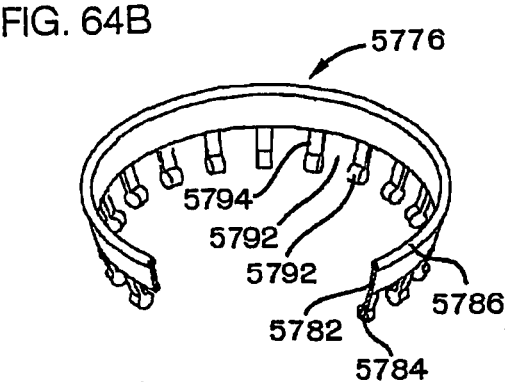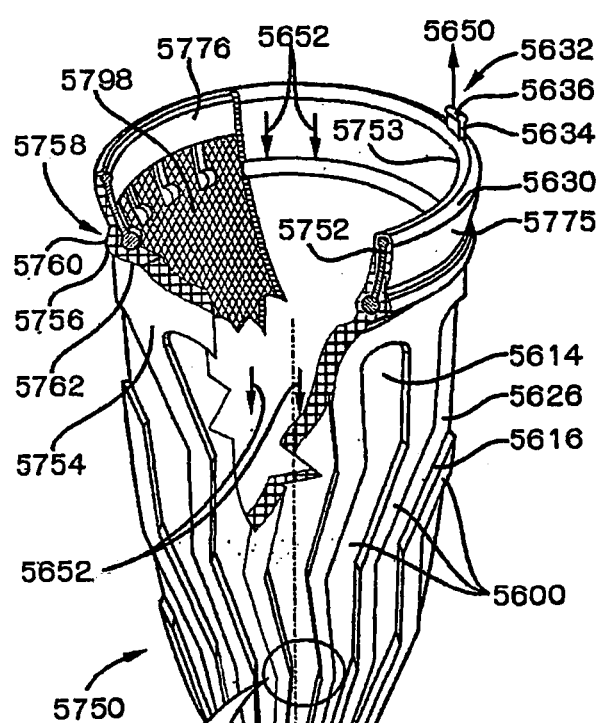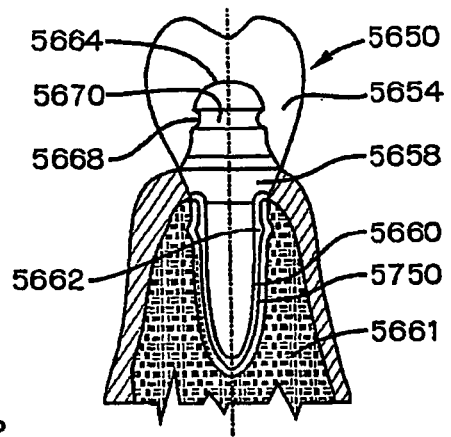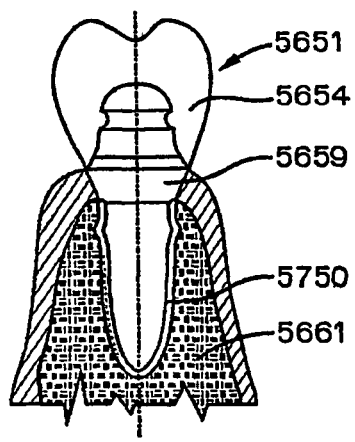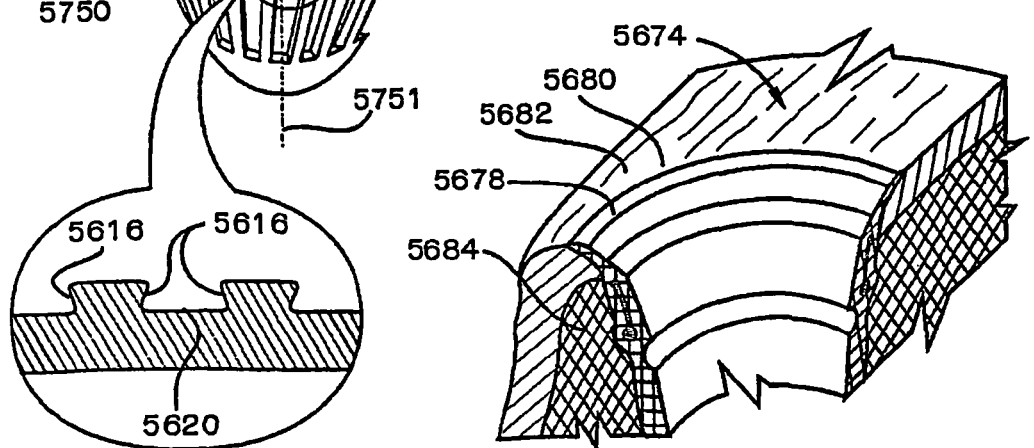

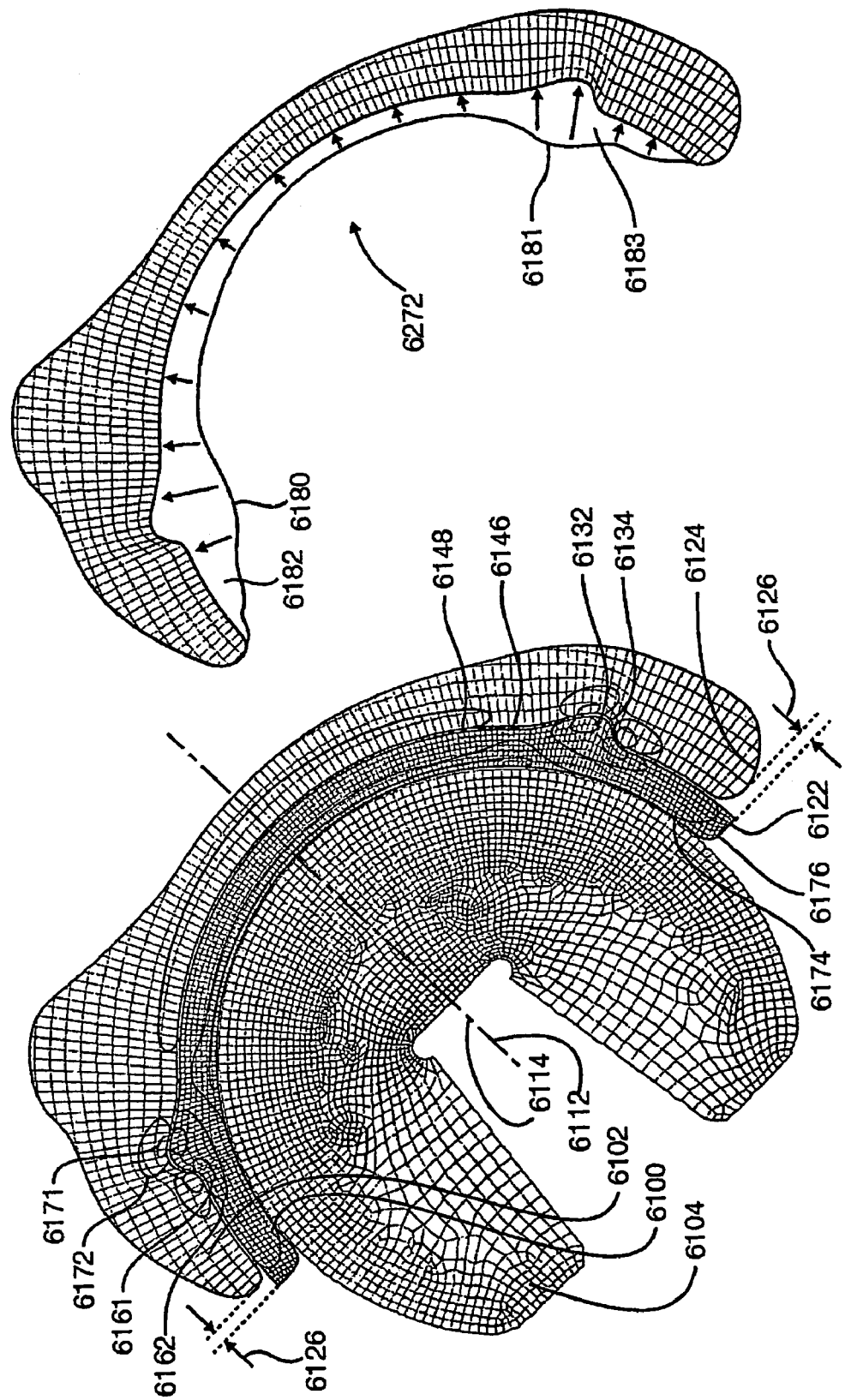

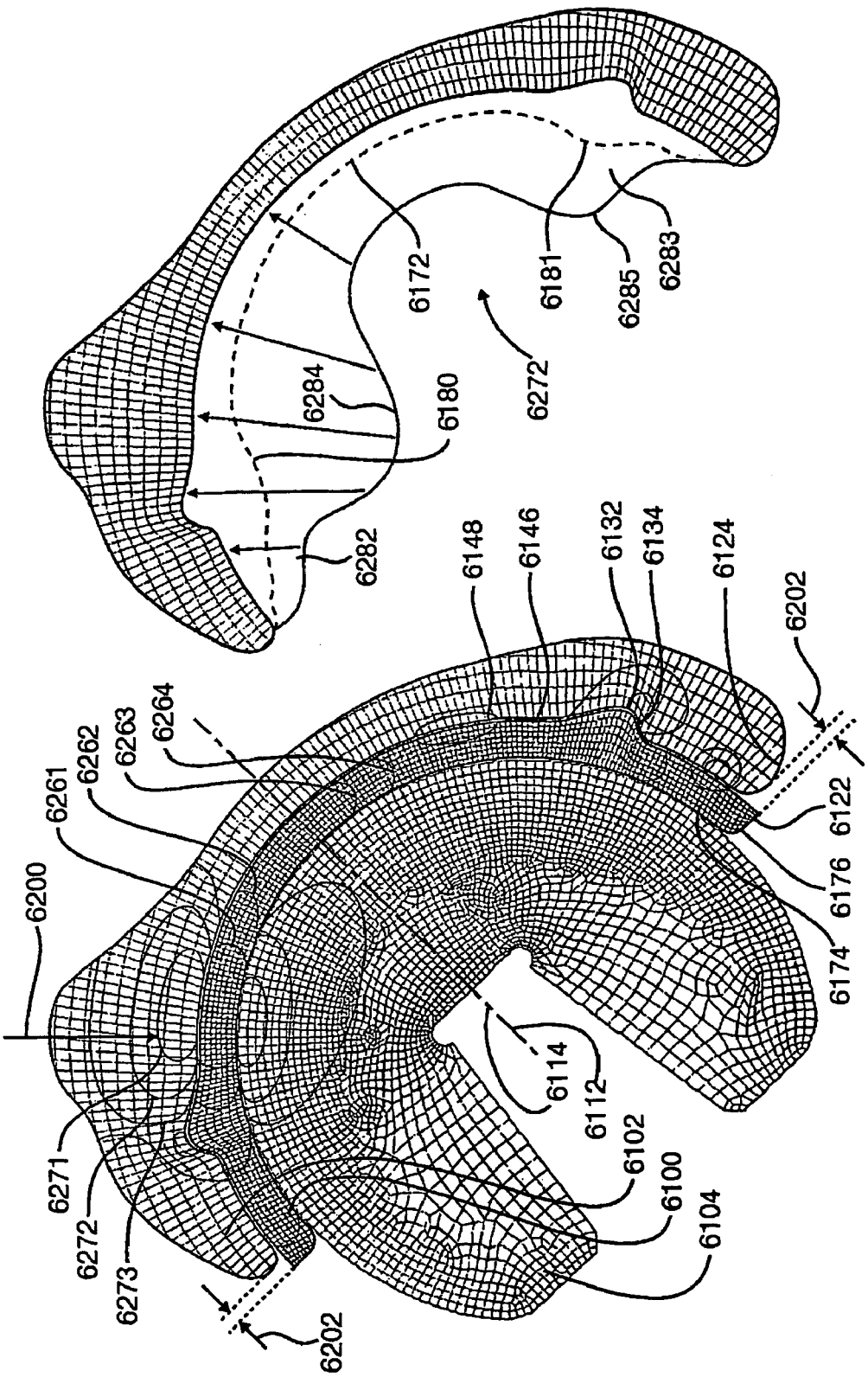

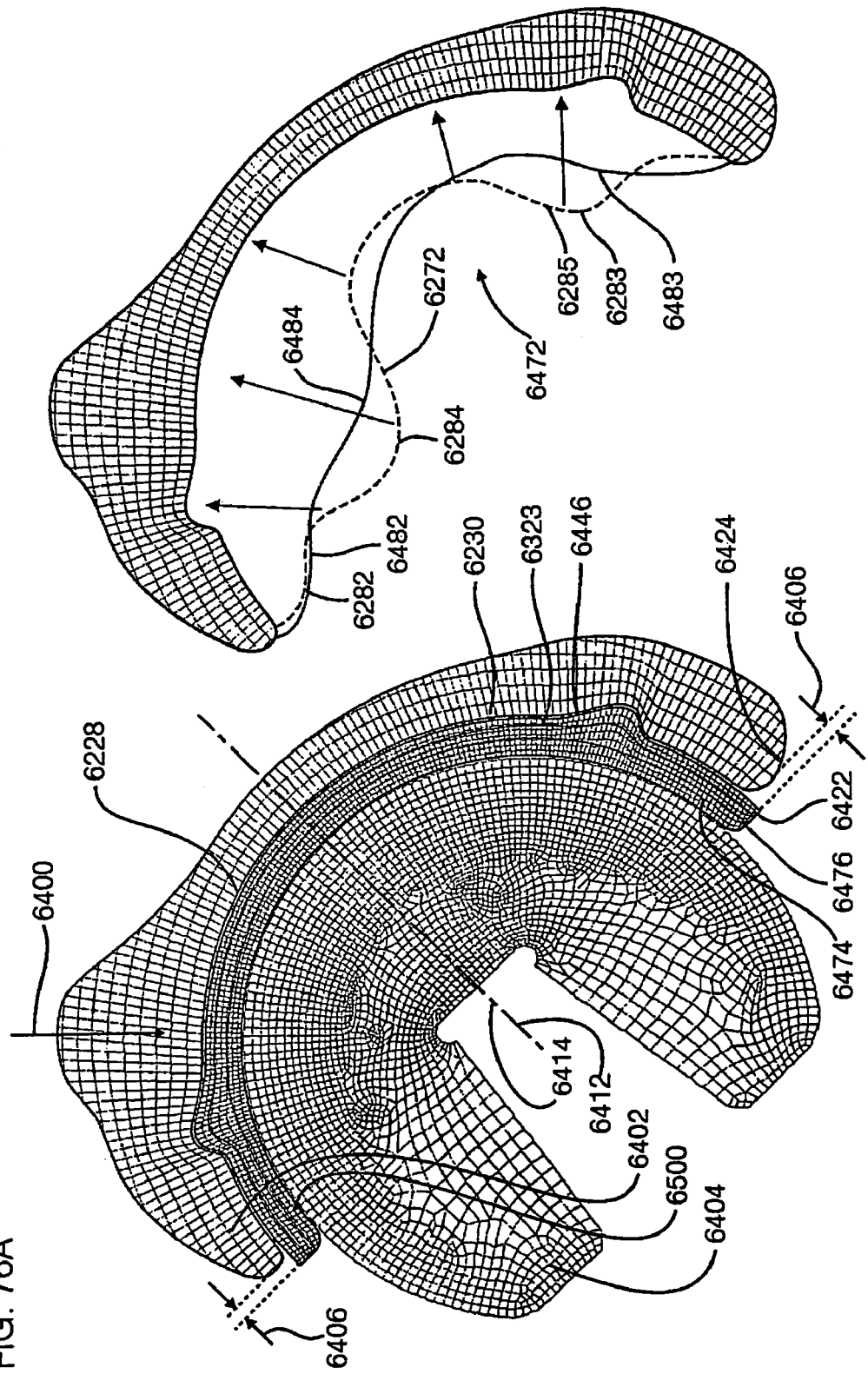

IMPLANTS

REFERENCE TO RELATED APPLICATIONS

This application is partially based upon and claims priority from:

U.S. Provisional Patent Application Ser. No. 60/383,483 filed May 23, 2002 and entitled "JOINT IMPLANTS SYSTEM AND METHODOLOGY AND IMPLANTS AND TOOLS USEFUL THEREWITH"; and PCT Patent Application Serial No. PCT/IL02/00972 filed on Dec. 3, 2002 and entitled: "CUSHION BEARING IMPLANTS FOR LOAD BEARING APPLICATIONS"; and PCT Patent Application Serial No. PCT/IL03/00063.A filed on Jan. 24, 2003 and entitled: "JOINT PROSTHESIS"

FIELD OF THE INVENTION

The present invention relates generally to implants and methods relating thereto.

BACKGROUND OF THE INVENTION

The following patents are believed to be relevant to the subject matter of this application:

---

U.S. Pat. Nos. 5,201,881; 5,011,497; 4,279,041; 5,080,675; 4,650,491; 3,938,198; 4,292,695; 4,624,674; 2,765,787; 4.735,625; 5,370,699; 5,641,323; 5,323,765; 5,658,345; 3,875,594; 3,938,198; 4,292,695; 4,344,193; 4,570,270; 4,650,491; 4,279,041; 4,661,112; 4,662,889; 4,664,668; 4,715,859; 4,795,470; 4,795,474; 4,808,186; 4,813,962; 4,822,365; 4,888,020; 4,904,269; 4,908,035; 4,919,674; 4,919,678; 4,936,856; 4,938,771; 4,938,773; 4,950,298; 4,955,912; 4,955,919; 4,963,153; 4,963,154; 4,997,447; 5,002,581; 5,019,107; 5,041,140; 5,049,393; 5,080,677; 5,108,446; 5,108,451; 5,116,374; 5,133,763; 5,146,933; 5,147,406; 5,151,521; 5,156,631; 5,171,276; 5,181,925; 5,197,987; 5,197,989; 5,201,881; 5,201,882; 5,217,498; 5,217,499; 5,222,985; 5,282,868; 5,290,314; 5,314,478; 5,314,494; 5,316,550; 5,326,376; 5,330,534; 5,314,493; 5,336,268; 5,344,459; 5,358,525; 5,370,699; 5,376,064; 5,376,125; 5,387,244; 5,389,107; 5,405,403; 5,405,411; 5,415,662; 5,425,779; 5,448,489; 5,458,643; 5,458,651; 5,489,311; 5,491,882; 5,507,814; 5,507,818; 5,507,820; 5,507,823; 5,507,830; 5,507,833; 5,507,836; 5,514,182; 5,514,184; 5,522,904; 5,507,835; 5,246,461; 5,364,839; 5,376,120; 5,393,739; 5,480,449; 5,510,418; 5,522,894; 4,892,551; 5,660,225; 4,089,071; 5,281,226; 5,443,383; 5,480,437; 5,032,134; 4,997,444; 5,002,579; 5,443,512; 5,133,762; 5,080,678; 5,944,759; 5,944,758; 5,944,757; 5,944,756; 5,938,702; 5,935,174; 5,935,175; 5,935,173; 5,935,172; 5,935,171; 5,931,871; 5,931,870; 5,928,289; 5,928,288; 5,928,287; 5,928,286; 5,928,285; 5,919,236; 5,916,270; 5,916,269; 5,916,268; 5,913,858; 5,911,759; 5,911,758; 5,910,172; 5,910,171; 5,906,644; 5,906,643; 5,906,210; 5,904,720; 5,904,688; 5,902,340; 5,882,206; 5,888,204; 5,879,407; 5,879,405; 5,879,404; 5,879,402; 5,879,401; 5,879,398; 5,879,397; 5,879,396; 5,879,395; 5,879,393; 5,879,392; 5,879,390; 5,879,387; 5,871,548; 5,871,547; 5,824,108; 5,824,107; 5,824,103; 5,824,102; 5,824,101; 5,824,098; 5,800,560; 5,800,558; 5,800,557; 5,800,555; 5,800,554; 5,800,553; 5,788,704; 5,782,928; 5,782,925; 5,776,202; 5,766,260; 5,766,257; 5,755,811; 5,755,810; 5,755,804; 5,755,801; 5,755,799; 5,743,918; 5,910,172; 5,211,666; 5,507,832; 4,433,440; 5,397,359; 5,507,834; 5,314,492; 5,405,394; 5,316,550; 5,314,494; 5,413,610; 5,507,835; 5,373,621; 5,433,750; 3,879,767; 5,376,123; 5,480,437; 3,576,133; 5,376,126; 5,496,375; 3,600,718; 5,108,449; 5,507,817; 5,181,929 and 5,507,829.

Foreign patents DE 2,247,721; EP 0,308,081; GB 2,126,096; GB 2,069,338; EP 0,190,446; EP 0,066,092 and EP 0,253,941.

---

Foreign patents DE 2,247,721; EP 0,308,081; GB 2,126,096; GB 2,069,338; EP 0,190,446; EP 0,066,092 and EP 0,253,941.

SUMMARY OF THE INVENTION

The present invention seeks to provide improved joint and dental implants and methods relating to joint and tooth implantation by employing a novel set of mechanical techniques which are interface with the biological medium and improve anchoring to the surrounding bone.

It is known in the art that bones react to stress and strain according to Wolff's Law. Wolff's Law is known to express the biological response to stress fields generated within the bone substance. The biological response to a certain normal stress magnitude generates the growth of new bone cells. The biological response to a certain extreme stress magnitude does not generate the growth of new bone cells but causes bone resorption.

It is additionally known that bone adaptively responds to frequency and magnitude of applied load. Therefore it can be stated that temporal and spatial regulation of loads may result in bone remodeling and overall increase of bone mass. Furthermore, bone tissue of a wide range of organisms remodels its shape and constitution to fit the same level of strain under normal activity. The application of different strain levels results in the growth of different types of cells: calcellous, cortical or cartilage.

It is further known in the art that in the vicinity of rigid implants, such as metal implants, there are regions of stress shielding in some parts of the bone, meaning that such rigid implants take load formerly transferred to the bone, thereby shielding the bone from the load and causing bone resorption. This process has been observed in regions such as in the proximal medial bone after hip replacement, and such as under the tibial component of knee replacements.

Prostheses described herein apply a set of design features which are all aimed at the utilization of the abovemensioned bone-growth properties. These include design of loading, interface configuration, mechanical properties of the pliable material from which the prostheses are formed, and the molding of deformation control elements within the prostheses. All of these, employed by persons skilled in the art, are expected to produce desired controlled deformations within the prosthesis. Under these combined conditions desired controlled deformations produced within the prosthesis substance are associated with the transmission of compression stress of desired magnitude distributed in desired region within the prosthesis.

The present invention departs from prior art in the intentional handling of stresses. While prior art allows for the presence of sharp or narrow features in the resilient material design, the inventions described herein adhere to the principles of fluid pressure management: in particular, the pliable implant described in the invention may distribute stresses in such a way that while load is exerted in one part of the implant, stress field develops in other regions, resembling the way stress is distributed by a contained fluid. Control of the cross section may further determine pressures in a similar way to the flow of fluid within a conduit. The preferred embodiments of the invention avoid sharp features in accordance with this principle, since sharp features impede the flow of fluid and pressure lines.

The implants of the present invention comprise of flexible elements, and also preferably include deformation control elements, resulting in improved load distribution, which prevent or significantly reduce stress shielding.

One method of stress control is by interface geometry utilizing oversized thickness to exert constant compression stress. As discussed hereinabove, it is appreciated that the stresses produced in the natural bone, such as in the natural acetabulum socket, produce corresponding strains therein. Both the stresses and the strains have positive medical implications which are expressed in bone remodeling by growing new bone cells of structural characteristics. The resulting, long term regeneration of bone distributes stresses optimally within the bone substance. Distributing stresses optimally brings the stress conditions as close as possible to the natural conditions. The improved stress-field distribution at the interface between the prosthesis and the bone helps prevent lysis.

Avoidance of bone resorption and deterioration and loss of bone geometry responsible for sustaining the long term effectiveness of the mechanical locking fixation of the artificial acetabulum socket is brought about by the implant strain control in accordance with this invention described hereinabove and more specific by the targeting of specific locations within the bone substance to be subjected to desired strain as is thought to promote bone regeneration and strengthening as detailed in bibliography known in the art cited hereinabove as opposed to the bone resorption and deterioration phenomena common in prior art devices.

There is thus provided in accordance with a preferred embodiment of the present invention an implantable artificial joint prosthesis including at least one joint defining element defining a bone-engaging surface, the bone-engaging surface including an anchoring mechanism operative for enhancing anchoring and adhesion of the joint defining element to the bone and thus improving the stability and longevity of the prosthesis.

In accordance with another preferred embodiment of the present invention an implantable tooth implant including at least one implant defining element defining a bone-engaging surface, the bone-engaging surface including an anchoring mechanism operative for enhancing anchoring and adhesion of the implant defining element to the bone and thus improving the stability and longevity of the prosthesis.

In accordance with another preferred embodiment of the present invention the at least one joint defining element is formed of a material having mechanical properties which are characterized by a nonlinear stress strain relationship.

In accordance with yet another preferred embodiment of the present invention the at least one joint defining element defines a generally hemispherical convex bone-engaging surface. Preferably, the at least one bone engagement surface has formed thereon a generally annular outwardly extending protrusion.

Alternatively, the at least one joint defining element defines a generally hemispherical concave bone-engaging surface. Preferably, the at least one bone engagement surface has formed thereon a generally annular inwardly extending protrusion.

In accordance with another preferred embodiment of the present invention the protrusion defines a generally annular undercut.

In accordance with still another preferred embodiment of the present invention the at least one bone-engaging surface is arranged for snap fit engagement with a bone. Additionally or alternatively, the at least one bone-engaging surface is arranged for press fit engagement with a bone.

In accordance with a preferred embodiment of the present invention, the at least one bone-engaging surface is configured with a hexagonal configuration pattern. Preferably, the hexagonal configuration pattern is defined by a plurality of protruding hexagonal contact surface portions, each surrounded by a peripheral channel. Alternatively, the hexagonal configuration pattern is defined by a plurality of recessed hexagonal contact surface portions, each surrounded by a peripheral channel. Preferably, the channels are each defined by wall surfaces and a bottom surface. Additionally or alternatively, the channels are defined to provide an undercut engagement portion.

In accordance with yet another preferred embodiment of the present invention the undercut engagement portion includes a relatively wider cross sectional dimension near the bottom surface and a relatively narrower cross sectional dimension away from the bottom surface.

In accordance with another preferred embodiment, the at least one bone-engaging surface is configured with a spiral configuration pattern. Preferably, the spiral configuration pattern is defined by spiral recess. Additionally, the spiral recess is defined by wall surfaces and a bottom surface. Additionally or alternatively, the spiral recess is defined to provide an undercut engagement portion. Preferably, the undercut engagement portion includes a relatively wider cross sectional dimension near the bottom surface and a relatively narrower cross sectional dimension away from the bottom surface.

In accordance with still another preferred embodiment of the present invention the at least one bone-engaging surface is configured with a pattern defined by a plurality of multidirectional generally radially extending elongate recesses. Preferably, the recesses are defined by wall surfaces and a bottom surface. Additionally or alternatively, the recesses are defined to provide an undercut engagement portion. Preferably, the undercut engagement portion includes a relatively wider cross sectional dimension near the bottom surface and a relatively narrower cross sectional dimension away from the bottom surface.

In accordance with another preferred embodiment of the present invention the at least one bone-engaging surface is configured with a geometric configuration pattern.

In accordance with yet another preferred embodiment of the present invention the at least one bone-engaging surface is configured with a fractal configuration pattern.

Further in accordance with a preferred embodiment of the present invention the implantable artificial socket for a joint is adapted for use as a tibial socket and defining an articulation portion having a concave inner articulation surface and a bone engagement portion having a bone engagement surface.

Preferably, the articulation portion is formed with a highly resilient hollow peripheral rim arranged for snap fit engagement with a corresponding peripheral socket formed in a surface of the bone engagement portion, opposite to the bone engagement surface.

Additionally in accordance with a preferred embodiment of the present invention the articulation portion is formed with a support protrusion, defining an undercut and arranged for resilient snap fit locking engagement with a corresponding groove formed in the bone engagement portion.

Further in accordance with a preferred embodiment of the present invention the articulation surface has formed therein a plurality of throughgoing apertures and side openings, which allow synovial fluid to pass therethrough for lubrication of the articulation surface.

Still further in accordance with a preferred embodiment of the present invention the implantable artificial socket for a joint is mounted onto a tibia and arranged such that application of force to the joint causes the articulation portion to be resiliently displaced toward the bone engagement portion, thus causing synovial fluid, located between the articulation portion and the bone engagement portion, to be forced through apertures and openings so as to lie on and over the articulation surface and to provide enhanced lubrication for the articulation of an articulation surface of a femur with the articulation surface.

Typically, the application of force causes the movement of the articulation portion by resilient buckling of at least one protrusion and compression of a resilient rim and release of the force causes movement of the articulation portion, accompanied by resilient return of the protrusion to its unstressed orientation and decompression of the resilient rim, wherein the application of force does not cause significant deformation of the geometry of the articulation surface.

In accordance with a preferred embodiment of the present invention insertion of implants by gently positioning, gently engaging the artificial acetabulum socket at locations on an inner concave surface thereof and pressing thereon in a direction generally along an axis of symmetry of the snap fit configured natural acetabulum, thereby causing displacement of the artificial acetabulum socket, which produces radially inward compression of the artificial acetabulum socket at the protrusion and thereby resulting in deformation of the artificial acetabulum socket at the protrusion and in the general region thereof.

Further in accordance with a preferred embodiment of the present invention the radially inward compression and the resulting deformation of the artificial acetabulum socket produce stresses in the acetabulum socket and cause forces to be applied to the acetabulum, producing compression stresses and strains therein.

Additionally in accordance with a preferred embodiment of the present invention the displacement of the artificial acetabulum socket reduces the separation between the planes of the outer edge of the implantable artificial acetabulum socket and the outer edge of the acetabulum.

Still further in accordance with a preferred embodiment of the present invention the method includes, following the gentle engaging, pressing further on the artificial acetabulum socket at locations on an inner concave surface thereof, thereby causing further displacement of the artificial acetabulum socket producing sliding pressure engagement between an underlying surface portion of the protrusion at the undercut and a radially outward extending surface portion of the groove, wherein resiliency of the artificial acetabulum socket causes radially outward displacement of the protrusion and corresponding radially outward decompression of the artificial acetabulum socket, resulting in reduced and changed stress patterns in both the artificial acetabulum socket and in the acetabulum.

Further in accordance with a preferred embodiment of the present invention the displacement of the artificial acetabulum socket further reduces the separation between the planes of the outer edge of the implantable artificial acetabulum socket and the outer edge of the acetabulum.

Further in accordance with a preferred embodiment of the present invention the method further includes, following the pressing further, pressing on the artificial acetabulum socket at locations on edges thereof, thereby causing further displacement of the artificial acetabulum socket and producing sliding snap fit engagement between the protrusion and the groove, wherein the resiliency of the artificial acetabulum socket causes radially outward displacement of the protrusion, thereby generally eliminating deformation of the artificial acetabulum socket at the protrusion and in the general region thereof.

Preferably, the snap fitting provides a generally non-press fit engagement, wherein touching engagement between the artificial acetabulum socket and the acetabulum produces stresses in both the acetabulum socket and in the acetabulum which are generally small and localized in the region of the snap fit engagement therebetween.

Further in accordance with a preferred embodiment of the present invention the snap fitting produces locking of the artificial acetabulum socket in the groove and the undercut prevents disengagement of the protrusion from the groove.

Additionally in accordance with a preferred embodiment of the present invention the snap fitting provides a generally press fit engagement, wherein touching engagement between the artificial acetabulum socket and the acetabulum produces stresses in both the acetabulum socket and in the acetabulum which are not localized in the region of the snap fit engagement therebetween.

Further in accordance with a preferred embodiment of the present invention the snap fitting in a generally press fit engagement produces pressure engagement between the acetabulum and a convex facing surface of the artificial acetabulum socket generally along the entire extent thereof.

In accordance with a preferred embodiment of the present invention, additional stress fields exerted by external forces may be superimposed onto the stress fields produced by the snap fit and press fit engagements described hereinabove. Together with the external loads produced by loading of the joint, the stress field may be designed as to stimulate the growth of cells of structural characteristics.

In accordance with a preferred embodiment of the present invention, interface to the bone engaging surface may be configured over a limited area of the implant, or not configured at all, thus being particularly suitable for patients with limited mobility and who are only capable of low level of activity. It is appreciated that the fixation strength achieved by press fit and snap fit alone is sufficient for the loads imposed by the level of activity of such patients.

In accordance with a preferred embodiment of the present invention, implantable artificial acetabulum is not configured and is therefore allowed to deform towards the rim of the acetabulum. In accordance with yet another preferred embodiment of the present invention, the application of texture and configuration to the outer rim of an acetabular socket implant results in improved fixation and may thus prevent the crawl of said socket under the reduced pressure present near the rim.

The present invention provides a dental implant which effectively adheres to the mandibular bone by transmitting forces which are similar in orientation and magnitude to those transmitted via the periodontal membrane, thus preventing wear of the bone.

There is thus provided in accordance with a preferred embodiment of the present invention a bone engaging interface of an implantable tooth implant assembley, which is particularly suitable for use in a dental fixture and may serve as an artificial periodontal ligament replacement. Said bone engaging interface is preferably formed by injection molding of polyurethane, is preferably of generally uniform thickness, defining a concave inner fixture anchoring surface. Said bone engaging interface may have a beveled edge and a recess matched to provide for snap fit engagement of an implantable tooth implant assembly. Said bone engaging interface having at least one generally annular outwardly extending protrusion arranged for snap fit engagement with a corresponding groove formed by machining of a jaw bone. Preferably, said protrusion has a cross-section with an underlying slope sharper than the overlying slope.

There is further provided in accordance with a preferred embodiment of the present invention a method for implanting a peripheral and continuous recess between said protrusion and the rim of bone engaging interface allowing for bone to grow into the recess and form a protective barrier against germs.

It is also provided in accordance with a preferred embodiment of the present invention that the bone engaging interface is constructed from a single layer, preferably, molded of a polyurethane, and includes an inserted internal deformation control element. Said deformation control element preferably constructed of a rigid material. Alternatively the deformation control element is preferably formed of woven high performance fibers. Said deformation control element is preferably covered by PU inwardly, outwardly, and towards the rim. Said deformation control element preferably has an overall generally annular configuration defined by a web portion and a thickened portion, and is further defined by rectangular cutouts separated by flaps.

According to another preferred embodiment of the present invention the bone engaging interface incorporates a reinforcement constructed of high performance fibers, which allows it to imitate the function of the periodontal ligament.

In accordance with the principle described hereinabove the bone engaging interface design avoids sharp and narrowed features, thus avoiding stress compression, and keeping said fibers strength.

In another preferred embodiment of the present invention, the bone engaging interface is configured from material layers and reinforcement, providing shock absorbing characteristics and allowing a small amount of movement of the tooth. Such movement is preferable in view of reasons described in detail hereinbelow. The shock absorbing capability thus provided seeks to replace the functionality of the lost periodontal ligament.

In accordance with another preferred embodiment of the present invention the relationship between the form and the dimensions of bone engaging interface and the protrusion mounted upon it are, with respect to the form and the dimensions of the corresponding machined jaw bone, preferably arranged for press fit and snap fit engagement.

In accordance with a preferred embodiment of the present invention the bone engagement surface is configured with a pattern defined by a plurality of multidirectional generally radially extending elongated recesses. Said recesses are defined by wall surfaces and a bottom surface where walls are preferably inclined outwardly toward the bottom surface. It is a particular feature of these embodiments that when the bone engaging interface experiences forces and/or impacts, the resulting stresses and strains exerted within the jaw bone induce growth of new bone cells, which migrate into said recesses, creating an undercut locking engagement with the interface.

In accordance with yet another preferred embodiment of the present invention, the generally annular outwardly extending protrusion mounted on the bone engaging interface is configured with a similar configuration pattern.

In accordance with another preferred embodiment of the present invention, the outer surface of the bone engaging interface is preferably configured with a hexagonal configuration pattern.

Still further in accordance with a preferred embodiment of the present invention, preferably at least two ridge elements are integrally formed with the rim of the bone engaging interface. These grip elements preferably have an overall generally segmented or continuous annular configuration and are constructed operatively in accordance with still another preferred embodiment of the present invention to be gripped by the jaws of an implanter tool.

In accordance with a preferred embodiment of the present invention a dental crown prosthesis is mounted on a crown abutment preferably constructed from a shock absorbing material. The Crown abutment is fixed into a fixture in the bone engaging interface.

In accordance with a preferred embodiment of the present invention the crown abutment may be fixed to the bone engaging interface by fixing into a fixture, or snap fitting, or alternatively snap fitting and press fitting, or by a bayonet-type connection, or by screwing.

In accordance with a preferred embodiment of the present invention dental fixture may be fixed to bone engaging interface by any of snap-fit, press-fit, bayonet-type connection or screwed.

In accordance with a preferred embodiment of the present invention the crown abutment may be directly fixed into the bone engaging interface without an intermediary element. All fixation method listed in the previous paragraph may apply here as well.

Still further in accordance with a preferred embodiment of the present invention, the implantable tooth implant assembly is preferably implanted into the jaw bone by an implanter tool. The grip ridge elements of the bone engaging interface are constructed and operative in accordance with still another preferred embodiment of the present invention to be gripped by the jaws of an implanter tool. Said implanter tool may be provided for the surgeon to perform the implanting of the implantable dental implant simultaneously with the bone engaging interface in one smooth installation process.

In accordance with a preferred embodiment of the present invention an implanter tool simultaneously stretch bone interface by grasping grip ridge elements at the rim of the bone engaging interface and push the concave inner fixture anchoring surface and by implanter tool element or dental implant.

In accordance with a preferred embodiment of the present invention, a surgeon using an implanter tool inserts into the suitably machined jaw bone the implantable tooth assembly parts according to their order and then proceeds to operate the implanter to continuously change flexing and pushing forces until the assembly parts are properly installed.

Still further in accordance with a preferred embodiment of the present invention, preferably grip ridge elements are formed on implantable sockets and operative with an implanter tool.

In accordance with a preferred embodiment of the present invention therein provided a flexible gum embankment element formed bone interface and extended outwardly and upwardly from the rim.

There is also provided in accordance with a preferred embodiment of the present invention an artificial femoral head prosthesis for use with a natural femoral head. This includes a bone interface element configured to be mounted onto the natural femoral head, the bone interface element having an inner concave surface which is configured to directly contact the natural femoral head in generally static engagement therewith. The bone interface element being particularly configured for retainable snap fit engagement with a suitably machine-shaped surface of the natural femoral head and a press fit acetabulum engagement element being particularly configured for retainable press fit engagement with the bone interface element. Having a smooth outer convex surface the implant is configured to be directly contacted by an acetabulum socket in moveable engagement therewith.

In accordance with yet another preferred embodiment of the present invention all bone engaging implants described herein may include a bioactive coating. Preferably, the bioactive coating is formed by grit blasting. Alternatively, the bioactive coating is formed by spraying. In accordance with another preferred embodiment, the bioactive coating also includes an elastomer, or may be composite, including an elastomer and bioactive materials, such as Hydroxylapatite (HA). HA may resorb with time. These bioactive materials cause the contact surface of the artificial implantation device to become bioactive, stimulating bone growth to provide an adhesion of the implant to the bone and accelerate osteointegration.

The feedstock for said coating can be in powder form or a PU rod or any combination.

In accordance with a preferred embodiment of the present invention a spraying apparatus is used, where coating is preferably provided using a combustion process, directed by a nozzle. The process may start with a preheating step that is designed to melt the surface of the implant and provide for a chemical bond between the surface and the polyurethane particles. Alternatively, a coating can be deposited onto the contact surface of artificial the implantation device by means of dipping.

The coating may be an elastomer on elastomer coating.

In addition to the enhanced bone adhesion methods described herein, the contact surface of an artificial implantation device may also be treated using one of the following Surface Modification processes: Atomic cleaning, adhesion promotion, molecular grafting, cell attachment enhancement, and Plasma Enhanced Chemical Vapor Deposition (PECVD) coatings, such as implemented by the MetroLine Surface, Inc. Surface modification processes improve the articulating properties of the contact surface by reducing friction and thereby enhance the resistance to wear.

BRIEF DESCRIPTION OF THE DRAWINGS

The present invention will be understood and appreciated more fully from the following detailed description, taken in conjunction with the drawings in which:

FIGS. 64A and 64B are respective pictorial and partially cut away illustrations of a bone engaging interface of an implantable tooth root implant constructed and operative in accordance with a preferred embodiment of the present invention;

FIGS. 65A and 65B are sectional illustrations of an implantable tooth implant assembly mounted onto a jaw bone in accordance with a preferred embodiments of the present invention;

FIG. 66 is a pictorial and partially cut away illustration of a bone engaging interface of an implantable tooth root implant mounted onto a jaw bone in accordance with a preferred embodiments of the present invention constructed and operative in accordance with a preferred embodiment of the present invention;

FIGS. 74A and 74B are simplified meshed sectional illustrations of an artificial hip joint constructed and operative in accordance with a preferred embodiment of the present invention, showing stress fields produced by press fit installation of an implantable artificial socket;

FIGS. 75A and 75B are simplified meshed sectional illustrations of the artificial hip joint of FIG. 74, showing changed stress fields resulting from loading of the joint;

FIGS. 76A and 76B are simplified meshed sectional illustrations of an artificial hip joint constructed and operative in accordance with another preferred embodiment of the present invention, showing stress fields resulting from loading of the joint which are modified by provision of deformation control layers in the implantable artificial socket and by variations in the thickness of an implantable artificial socket;

DETAILED DESCRIPTION OF PREFERRED EMBODIMENTS

Figure 1:
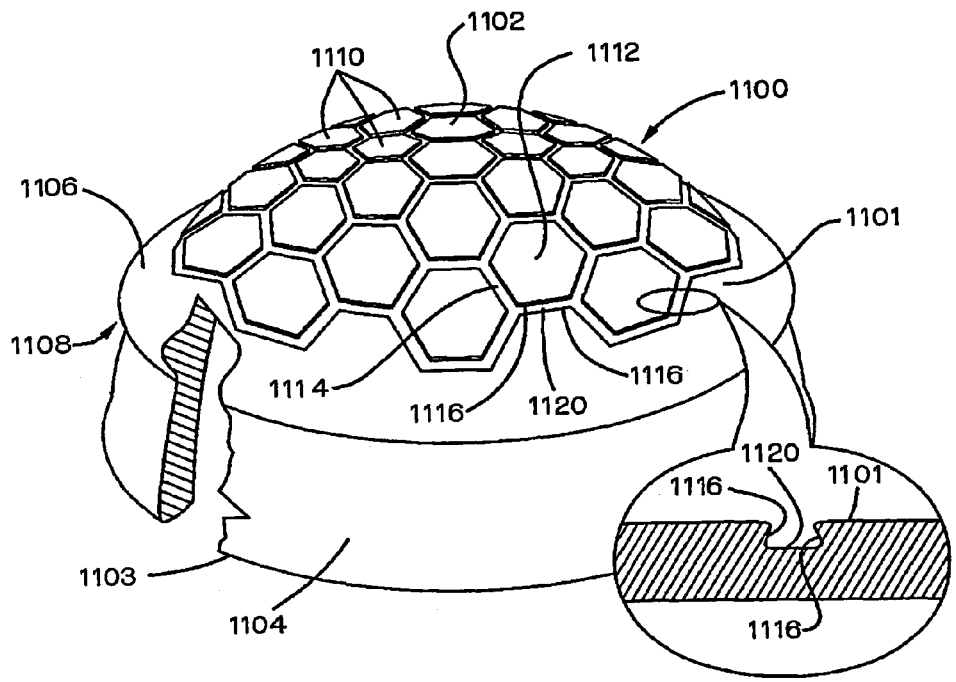
FIGS. 1, 2, 3 and 4 are pictorial illustrations of an implantable artificial socket constructed and operative in accordance with a preferred embodiment of the present invention.

Reference is now made to FIG. 1, which is a pictorial illustration of an implantable artificial socket constructed and operative in accordance with a preferred embodiment of the present invention and which is particularly suitable for use in a hip joint. The embodiment of FIG. 1 is particularly directed to providing an anchoring mechanism on a bone-engaging surface of the artificial socket for enhancing the anchoring and adhesion of the socket to the bone and thus improving the stability and longevity of the prosthesis.

As seen in FIG. 1, an implantable artificial socket, designated by reference numeral 1100, is formed preferably by injection molding of a bio stable and bio compatible pliable material such as an elastomer, preferably polyurethane, having mechanical properties which are characterized by a non-linear stress strain relationship.

Preferably, implantable artificial socket 1100 is of generally uniform thickness and defines a generally hemispherical convex bone engagement surface 1101 and a partially hemispherical convex bone engagement surface 1104 which preferably have formed thereon, at any suitable location between its apex 1102 and its rim 1103, a generally annular outwardly extending protrusion 1106, preferably defining a generally annular undercut 1108. Alternatively, the protrusion 1106 may be any other suitable annular or non-annular, continuous or discontinuous, generally peripheral, protrusion. The protrusion 1106 is preferably arranged for snap fit engagement with a corresponding groove formed by reaming of a bone.

In accordance with another preferred embodiment of the present invention, the relationship between the form and the dimensions of implantable artificial socket 1100 and the protrusion 1106 are, with respect to the form and the dimensions of the corresponding reamed bone, preferably arranged for press fit and snap fit engagement with the bone. The press fit feature is typically provided by making the outer dimensions of socket 1100 slightly larger than the corresponding dimensions of the machined bone surface onto which the socket fits.

The convex bone engagement surface 1101 is preferably configured with a hexagonal configuration pattern 1110, preferably defined by a plurality of protruding hexagonal contact surface portions 1112, each surrounded by a peripheral channel 1114. Channels 1114 are defined by wall surfaces 1116 and a bottom surface 1120. In accordance with a preferred embodiment of the present invention, channels 1114 are configured with wall surfaces 1116 being inclined outwardly toward the bottom surface 1120, creating an undercut configuration having a relatively wider cross sectional dimension near the bottom surface and a relatively narrower cross sectional dimension away from the bottom surface.

It is a particular feature of the embodiment of FIG. 1 that when the artificial joint equipped with implantable artificial socket 1100 experiences forces and/or impacts, such as those having a cyclic nature resulting from walking or running, the resulting stresses and strains exerted within the bone in proximity to the bone engagement surface 1101 induce growth of new bone cells, which, gradually, over time migrate into the channels 1114. The new bone cells typically press on other cells, creating remodeling of the bone in engagement with bone engagement surface 1101, causing the bone to migrate into the channels 1114 gradually, over time, and thus create an undercut locking engagement with the socket 1100.

In accordance with another preferred embodiment of the present invention, the partially hemispherical convex bone engagement surface 1104 is preferably configured with a configuration pattern similar to the hexagonal configuration pattern 1110.

In accordance with yet another preferred embodiment of the present invention, the generally annular outwardly extending protrusion 1106 is preferably configured with a configuration pattern similar to the hexagonal configuration pattern 1110 or configured with a pattern made of pattern segments similar to the hexagonal configuration pattern 1110.

Figure 2:
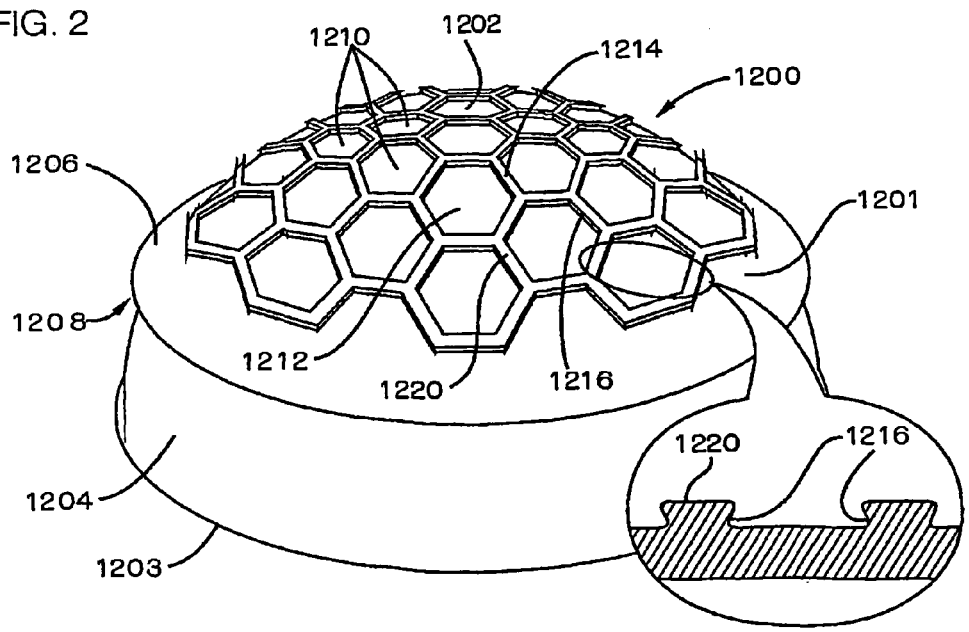

Reference is now made to FIG. 2, which is a pictorial illustration of an implantable artificial socket constructed and operative in accordance with a preferred embodiment of the present invention and which is particularly suitable for use in a hip joint. The embodiment of FIG. 2 is also particularly directed to providing an anchoring mechanism on a bone-engaging surface of the artificial socket for enhancing the anchoring and adhesion of the socket to the bone and thus improving the stability and longevity of the prosthesis.

As seen in FIG. 2, an implantable artificial socket, designated by reference numeral 1200, is formed preferably by injection molding of a bio stable and bio compatible pliable material such as an elastomer, preferably polyurethane, having mechanical properties which are characterized by a non-linear stress strain relationship.

Preferably, implantable artificial socket 1200 is of generally uniform thickness and defines a generally hemispherical convex bone engagement surface 1201 and a partially hemispherical convex bone engagement surface 1204 which preferably have formed thereon, at any suitable location between its apex 1202 and its rim 1203, a generally annular outwardly extending protrusion 1206 similar to a generally annular outwardly extending protrusion 1106 as shown in FIG. 1 hereinabove, preferably defining a generally annular undercut 1208. Alternatively, the protrusion 1206 may be any other suitable annular or non-annular, continuous or discontinuous, generally peripheral, protrusion. The protrusion 1206 is preferably arranged for snap fit engagement with a corresponding groove formed by reaming of a bone.

In accordance with another preferred embodiment of the present invention, the relationship between the form and the dimensions of implantable artificial socket 1200 and the protrusion 1206 are, with respect to the form and the dimensions of the corresponding reamed bone, preferably arranged for press fit and snap fit engagement with the bone. The press fit feature is typically provided by making the outer dimensions of socket 1200 slightly larger than the corresponding dimensions of the machined bone surface onto which the socket fits.

The convex bone engagement surface 1201 is preferably configured with a hexagonal configuration pattern 1210 preferably defined by a plurality of recessed hexagonal contact surface portions 1212, each surrounded by a peripheral ridge 1214. Ridges 1214 are defined by wall surfaces 1216 and a top surface 1220. In accordance with a preferred embodiment of the present invention, ridges 1214 are configured with wall surfaces 1216 being inclined outwardly toward the top surface 1220, creating an undercut configuration at said recessed hexagonal contact surface portions 1212 having a relatively wider cross sectional dimension near surface portions 1212 and a relatively narrower cross sectional dimension away from the surface portions 1212.

It is a particular feature of the embodiment of FIG. 2 that when the artificial joint equipped with implantable artificial socket 1200 experiences forces and/or impacts, such as those having a cyclic nature resulting from walking or running, the resulting stresses and strains exerted within the bone in proximity to the bone engagement surface 1201 induce growth of new bone cells, which, gradually, over time, migrate into the regions above surface portions 1212. The new bone cells typically press on other cells, creating remodeling of the bone in engagement with bone engagement surface 1201, causing the bone to migrate into the regions above surface portions 1212 gradually, over time, and thus create an undercut locking engagement with the socket 1200.

In accordance with another preferred embodiment of the present invention, the partially hemispherical convex bone engagement surface 1204 is preferably configured with a configuration pattern similar to the hexagonal configuration pattern 1210.

In accordance with yet another preferred embodiment of the present invention, the generally annular outwardly extending protrusion 1206 is preferably configured with a configuration pattern similar to the hexagonal configuration pattern 1210 or configured with a pattern made of pattern segments similar to the hexagonal configuration pattern 1210.

Figure 3:
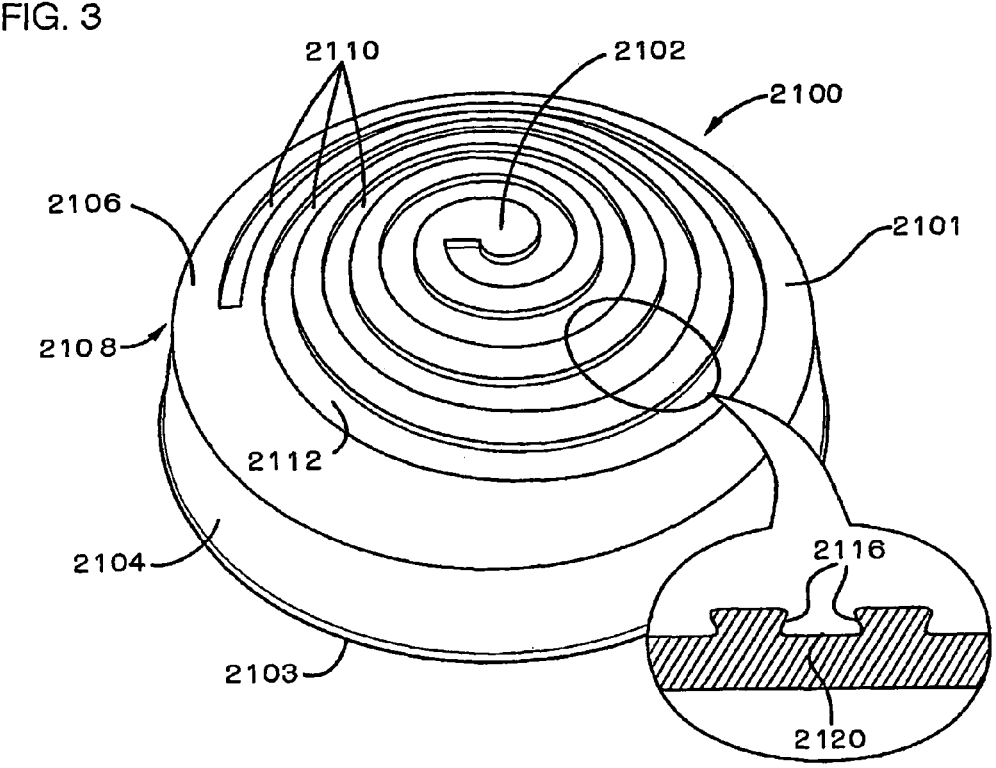

Reference is now made to FIG. 3, which is a pictorial illustration of an implantable artificial socket constructed and operative in accordance with a preferred embodiment of the present invention and which is particularly suitable for use in a hip joint.

As seen in FIG. 3, an implantable artificial socket, designated by reference numeral 2100, is formed preferably by injection molding of a bio stable and bio compatible pliable material such as an elastomer, preferably polyurethane, having mechanical properties which are characterized by a non-linear stress strain relationship.

Preferably, implantable artificial socket 2100 is of generally uniform thickness and defines a generally hemispherical convex bone engagement surface 2101 and a partially hemispherical convex bone engagement surface 2104 which preferably have formed thereon, at any suitable location between its apex 2102 and its rim 2103, a generally annular outwardly extending protrusion 2106 similar to a generally annular outwardly extending protrusion 1106 as shown in FIG. 1 hereinabove, preferably defining a generally annular undercut 2108. Alternatively, the protrusion 2106 may be any other suitable annular or non-annular, continuous or discontinuous, generally peripheral, protrusion. The protrusion 2106 is preferably arranged for snap fit engagement with a corresponding groove formed by reaming of a bone.

In accordance with another preferred embodiment of the present invention, the relationship between the form and the dimensions of implantable artificial socket 2100 and the protrusion 2106 are, with respect to the form and the dimensions of the corresponding reamed bone, preferably arranged for press fit and snap fit engagement with the bone. The press fit feature is typically provided by making the outer dimensions of socket 2100 slightly larger than the corresponding dimensions of the machined bone surface onto which the socket fits.

The convex bone engagement surface 2101 is preferably configured with a spiral configuration pattern 2110 preferably defined by a recess 2112 configured in a spiral. Spiral recess 2112 is defined by wall surfaces 2116 and a bottom surface 2120. In accordance with a preferred embodiment of the present invention, spiral recess 2112 is configured with wall surfaces 2116 being inclined outwardly toward the bottom surface 2120, creating an undercut configuration having a relatively wider cross sectional dimension near the bottom surface and a relatively narrower cross sectional dimension away from the bottom surface. It is appreciated that, even though the illustrated embodiment shows a circular spiral configuration pattern 2110, any suitable spiral configuration pattern, such as an elliptic or non-symmetric spiral pattern, or any combination thereof, may be provided.

It is a particular feature of the embodiment of FIG. 3 that when the artificial joint equipped with implantable artificial socket 2100 experiences forces and/or impacts, such as those having a cyclic nature resulting from walking or running, the resulting stresses and strains exerted within the bone in proximity to the bone engagement surface 2101 induce growth of new bone cells, which, gradually, over time, migrate into the spiral recess 2112. The new bone cells typically press on other cells, creating remodeling of the bone in engagement with bone engagement surface 2101, causing the bone to migrate into the spiral recess 2102 gradually over time and thus create an undercut locking engagement with the socket 2100. In accordance with another preferred embodiment of the present invention, the partially hemispherical convex bone engagement surface 2104 is preferably configured with a configuration pattern similar to the hexagonal configuration pattern 2110.

In accordance with yet another preferred embodiment of the present invention, the generally annular outwardly extending protrusion 2106 is preferably configured with a configuration pattern similar to the hexagonal configuration pattern 2110 or configured with a pattern made of pattern segments similar to the hexagonal configuration pattern 2110.

Figure 4:
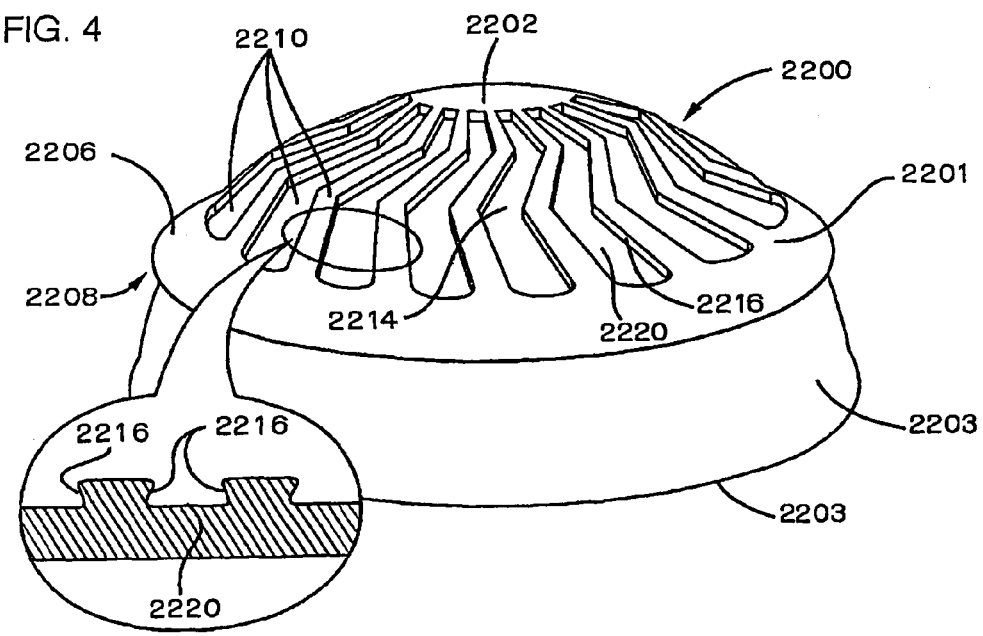

Reference is now made to FIG. 4, which is a pictorial illustration of an implantable artificial socket constructed and operative in accordance with a preferred embodiment of the present invention and which is particularly suitable for use in a hip joint.

As seen in FIG. 4, an implantable artificial socket, designated by reference numeral 2200, is formed preferably by injection molding of a bio stable and bio compatible pliable material such as an elastomer, preferably polyurethane, having mechanical properties which are characterized by a non-linear stress strain relationship.

Preferably, implantable artificial socket 2200 is of generally uniform thickness and defines a generally hemispherical convex bone engagement surface 2201 and a partially hemispherical convex bone engagement surface 2204 which preferably have formed thereon, at any suitable location between its apex 2202 and its rim 2203, a generally annular outwardly extending protrusion 2206 similar to a generally annular outwardly extending protrusion 1106 as shown in FIG. 1 hereinabove, preferably defining a generally annular undercut 2208. Alternatively, the protrusion 2206 may be any other suitable annular or non-annular, continuous or discontinuous, generally peripheral, protrusion. The protrusion 2206 is preferably arranged for snap fit engagement with a corresponding groove formed by reaming of a bone.

In accordance with another preferred embodiment of the present invention the relationship between the form and the dimensions of implantable artificial socket 2200 and the protrusion 2206 are, with respect to the form and the dimensions of the corresponding reamed bone, preferably arranged for press fit and snap fit engagement with the bone. The press fit feature is typically provided by making the outer dimensions of socket 2200 slightly larger than the corresponding dimensions of the machined bone surface onto which the socket fits.

The convex bone engagement surface 2201 is preferably configured with a pattern 2210 preferably defined by a plurality of multidirectional generally radially extending elongate recesses 2214. Recesses 2214 are defined by wall surfaces 2216 and a bottom surface 2220. In accordance with a preferred embodiment of the present invention, recesses 2214 are configured with wall surfaces 2216 being inclined outwardly toward the bottom surface 2220, creating an undercut configuration having a relatively wider cross sectional dimension near the bottom surface and a relatively narrower cross sectional dimension away from the bottom surface.

It is a particular feature of the embodiment of FIG. 4 that when the artificial joint equipped with implantable artificial socket 2200 experiences forces and/or impacts, such as those having a cyclic nature resulting from walking or running, the resulting stresses and strains exerted within the bone in proximity to the bone engagement surface 2201 induce growth of new bone cells, which, gradually, over time, migrate into the recesses 2214. The new bone cells typically press on other cells, creating remodeling of the bone in engagement with bone engagement surface 2201, causing the bone to migrate into the channels 2214 gradually, over time, and thus create an undercut locking engagement with the socket 2200.

It is appreciated that the hexagonal configuration pattern 1110 of FIG. 1 and the hexagonal configuration pattern 1210 of FIG. 2 are approximately obverse versions of the same pattern. It is appreciated that similar obverse versions of the configuration patterns of FIGS. 3 and 4 may also be provided. It is further appreciated that the illustrated patterns are intended as examples only, and any suitable configuration pattern, such as geometric or fractal patterns, may also be provided.

It is further appreciated that even though the illustrated embodiments comprise continuous configuration patterns, prostheses comprising any suitable combination of continuous or discontinuous configuration patterns, covering all or selected portions of the bone contact surface, may also be provided. In accordance with another preferred embodiment of the present invention, the partially hemispherical convex bone engagement surface 2204 is preferably configured with a configuration pattern similar to the hexagonal configuration pattern 2210.

In accordance with yet another preferred embodiment of the present invention, the generally annular outwardly extending protrusion 2206 is preferably configured with a configuration pattern similar to the hexagonal configuration pattern 2210 or configured with a pattern made of pattern segments similar to the hexagonal configuration pattern 2210.

It is further appreciated that in preferred embodiments of implants described in FIGS. 1-4 hereinabove implants may be constructed with any of the following: Where the material of the bone interface element being more flexible than that of bone; Where bone interface element is formed with at least one hollow portion; Where bone interface element contains at least one passageway for fluids; Where bone interface element is shock-absorbing; and wherein bone interface has mechanical properties of mammalian cartilage; Where bone interface is more resilient that the acetabulum or femoral head;

Where bone-interfacing element, connected to a first bone of a joint, articulates with a second element. Where said articulation may be mechanically delimited. Where an acetabular implant articulates with an artificial ball; Where ball has at least one delimiting element; Where ball delimiting element is constructed as a protrusion; where ball is more shock absorbing then the femur and acetabulum; Where ball is formed with a plurality of portions having different mechanical properties; where the plurality of portions are omega shaped; Where ball comprises an outer shell and an inner core; wherein said artificial ball is formed with a plurality of alternating adjacent first and second portions, said first portions being generally more rigid than said second portions. Where artificial ball is formed with hollows filled with fluids; Where artificial ball is formed with hollows and passageways for fluids; where said fluids are the synovial fluids;

Where said first and said second joint portions articulate with a third intermediate portion. Where motion with respect to said third portion is mechanically delimited;

Where bone-interface comprises at least two layers;

Where bone engaging element and artificial articulating element are separate. Where said bone engaging element and articulating element are connected by snap-fit, bayonet or thread.

Where bone interface element has a cut-out portion; where there is provided a fitting element for engagement at said cut out portion; where there is provided a locking portion for said engagement; where bone interface element is configured to receive the prongs of an insertion tool;

It is further appreciated that the abovementioned preferred embodiments may be deployed by a minimally invasive surgical technique, wherein a joint prosthesis comprising an artificial socket formed by expansion of an artificial socket precursor of relatively reduced dimensions, is configured for insertion into a joint environment with reduced disturbance of joint ligaments, said expansion taking place in situ between existing ligaments to a desired socket shape.

Figure 5A:
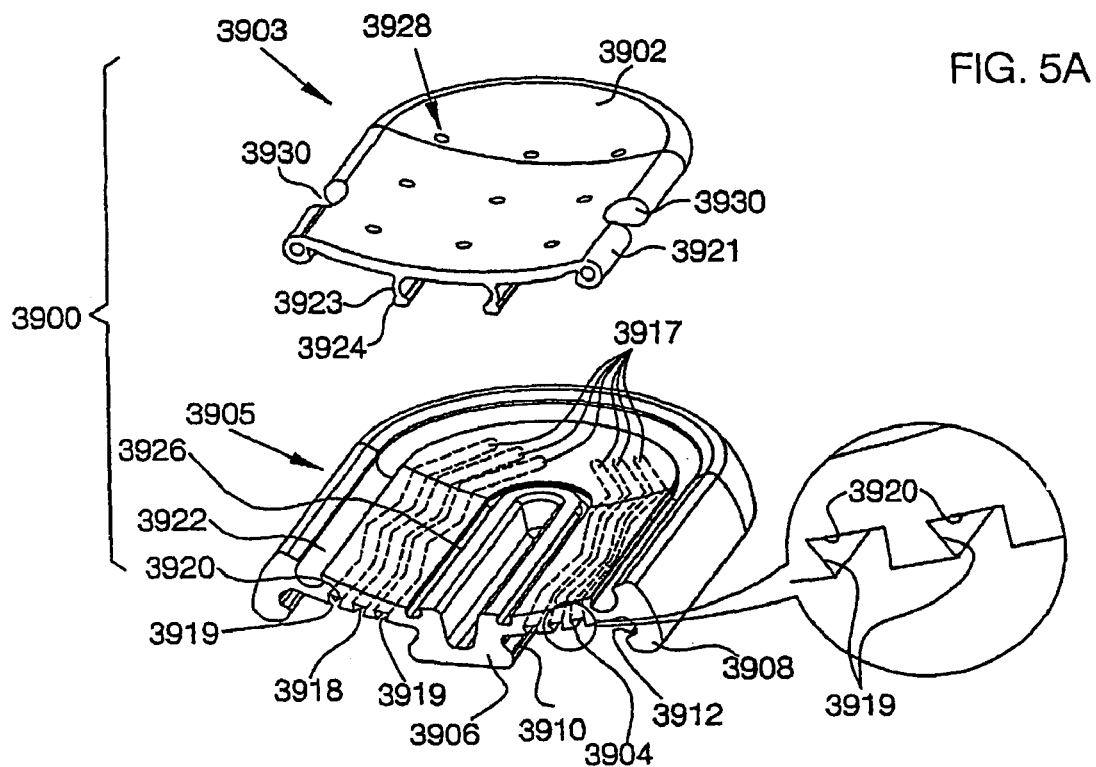
FIG. 5A is a simplified exploded view illustration of an implantable artificial tibial socket assembly constructed and operative in accordance with a preferred embodiment of the present invention in association with a suitably machined tibia.
Figure 5B:
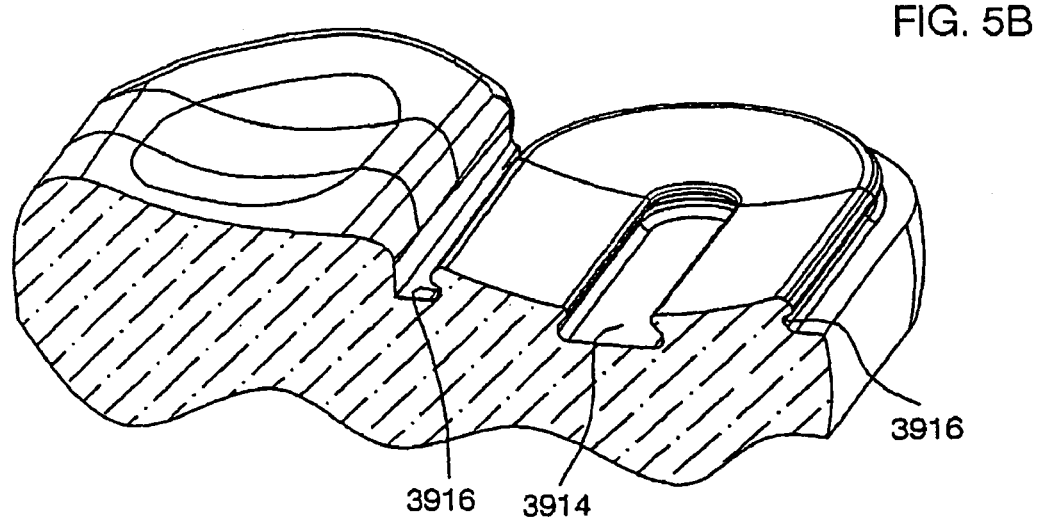
FIG. 5B is a simplified illustration a tibia, suitably machined to receive the implantable artificial tibial socket assembly of FIG. 5A.
Figure 6:
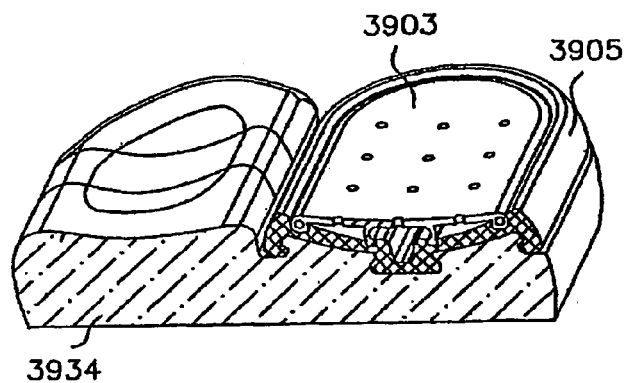
FIG. 6 is a simplified assembled view illustration of the implantable artificial tibial socket assembly of FIGS. 5A and 5B mounted onto a tibia in accordance with a preferred embodiment of the present invention.

Reference is now made to FIG. 5A, which is a simplified exploded view illustration of an implantable artificial tibial socket assembly constructed and operative in accordance with a preferred embodiment of the present invention in association with a suitably machined tibia and to FIG. 5B, which is a simplified illustration a tibia, suitably machined to receive the implantable artificial tibial socket assembly of FIG. 5A and to FIG. 6 which is a simplified illustration of implantable artificial tibial socket assembly assembled unto tibia 3934 and constructed and operative in accordance with a preferred embodiment of the present invention.

As seen in FIGS. 5A and 5B, an implantable artificial tibial socket assembly, designated by reference numeral 3900, is formed preferably by injection molding of a bio stable and bio compatible pliable material such as an elastomer, preferably polyurethane, having mechanical properties which are characterized by a nonlinear stress strain relationship.

Preferably, implantable artificial socket assembly 3900 defines a concave articulation surface 3902, which is defined on an articulation portion 3903, and a bone engagement surface 3904, which is defined on a bone engagement portion 3905. Bone engagement surface 3904 preferably has formed thereon multiple protrusions. In the illustrated embodiment, there are provided an inner protrusion 3906 and an outer peripheral protrusion 3908, defining respective undercuts 3910 and 3912. Alternatively, protrusions 3906 and 3908 may be any other suitable open or closed protrusions. Protrusions 3906 and 3908 are preferably arranged for snap fit engagement with corresponding grooves 3914 and 3916 provided by machining of the tibia.

In accordance with a preferred embodiment of the present invention, bone engagement surface 3904 has formed thereon a pattern 3917 defined by a plurality of multidirectional elongate recesses 3918 similar to the pattern 2210 shown in FIG. 4. Alternatively, pattern 3917 may be a hexagonal configuration pattern, similar to pattern 1110 of FIG. 1 or 1210 of FIG. 2, or a spiral configuration pattern similar to pattern 2110 of FIG. 3. Additionally, as described hereinabove, obverse patterns of these patterns or any other suitable configuration pattern may also be provided.

Recesses 3918 are configured with wall surfaces 3919 and a bottom surface 3920. In accordance with a preferred embodiment of the present invention recesses 3918 are configured to have wall surfaces 3919 inclined outwardly toward bottom surface 3920, creating an undercut configuration having a relatively wider cross sectional dimension near the bottom surface and a relatively narrower cross sectional dimension away from the bottom surface.

Articulation portion 3903 is formed with a highly resilient hollow peripheral rim 3921 arranged for snap fit engagement with a corresponding peripheral socket 3922 formed in a surface of bone engagement portion 3905, opposite to bone engagement surface 3904 thereof. Articulation portion 3903 also is formed with a support protrusion 3923, defining an undercut 3924 and arranged for resilient snap fit locking engagement with a corresponding groove 3926 formed in bone engagement portion 3905.

In accordance with a preferred embodiment of the present invention, articulation portion 3903 has formed in articulation surface 3902 a plurality of thoroughgoing apertures 3928 and side openings 3930, which allow synovial fluid to pass therethrough for lubrication of the articulation surface 3902.

It is a particular feature of the embodiment of FIG. 5A that when the artificial joint equipped with implantable artificial tibial socket assembly 3900 experiences forces and/or impacts, such as those having a cyclic nature resulting from walking or running, the resulting stresses and strains exerted within the bone in proximity to the bone engagement surface 3904 induce growth of new bone cells, which, gradually, over time, migrate into the recesses 3918. The new bone cells typically press on other cells, creating remodeling of the bone in engagement with bone engagement surface 3904, causing the bone to migrate into the recesses 3918 gradually, over time, and thus create an undercut locking engagement with the socket assembly 3900.

It is noted as seen in FIG. 6 and also in FIGS. 7A and 7B below that implantable artificial tibial socket assembly 3900 assembled unto tibia 3934 is shown as an embodiment of the present invention wherein no pattern such as the pattern 3917 is formed on bone engagement surface 3904. The bone engagement surface 3904 may be formed additionally, as described hereinabove, obverse patterns of these patterns or any other suitable configuration pattern or any other non-smooth textures may also be provided.

Figure 7A:
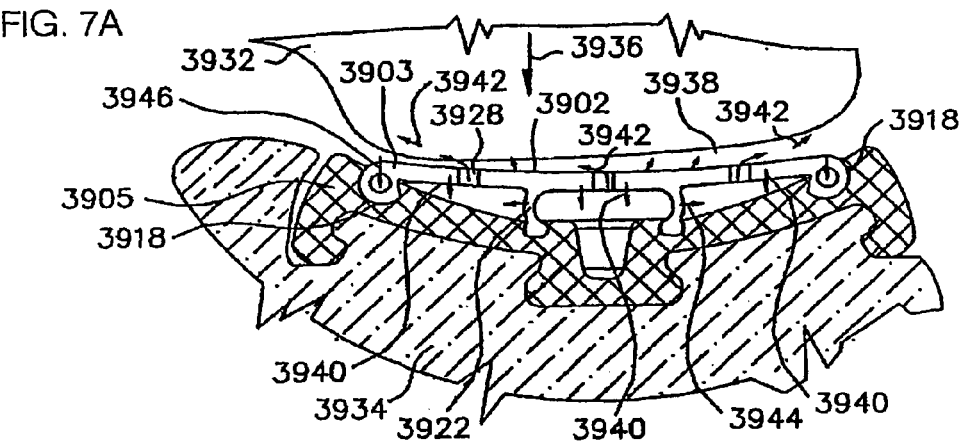
FIGS. 7A and 7B are sectional illustrations showing the implantable artificial tibial socket assembly of FIGS. 5A and 5B and FIG. 6 mounted onto a tibia in two alternative operative orientations.
Figure 7B:
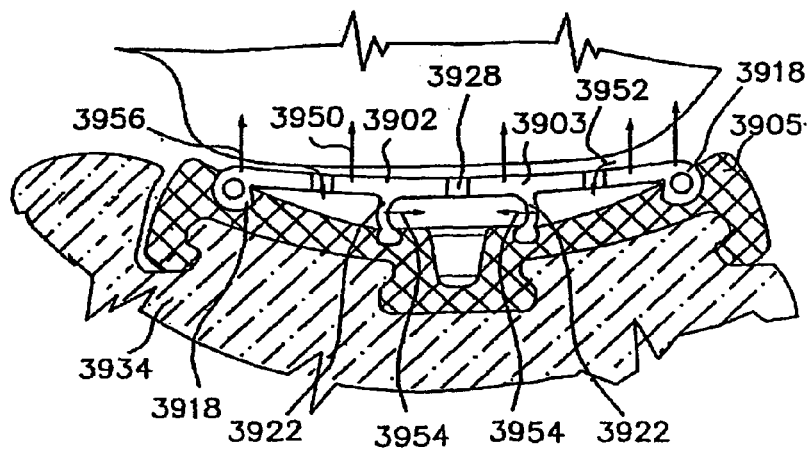

Reference is now made to FIGS. 7A and 7B, which are sectional illustrations showing the implantable artificial tibial socket assembly of FIGS. 29 & 30 mounted onto a tibia in two alternative operative orientations. FIG. 31A shows an operative orientation wherein the joint is loaded, e.g. the femur, here designated by reference numeral 3932, presses downward onto the tibia, here designated by reference numeral 3934. The loading force is designated by arrow 3936.

As seen in FIG. 7A, application of force 3936 causes the articulation portion 3903 to be resiliently displaced toward the bone engagement portion 3905, thus causing synovial fluid, located between the articulation portion 3903 and the bone engagement portion 3905 to be forced through apertures 3928 and openings 3930 so as to lie on and over articulation surface 3902 and to provide enhanced lubrication for the articulation of an articulation surface 3938 of femur 3932 with articulation surface 3902.

Considering FIGS. 7A and 7B, it is seen that the application of force 3936, causes movement of articulation portion 3903 as indicated by arrows 3940, and corresponding flow of synovial fluid as indicated by arrows 3942. This movement is accompanied by resilient buckling of protrusion 3922, as indicated by arrows 3944 and compression of resilient rim 3918, as indicated by arrows 3946.

Release of force 3936 causes movement of articulation portion 3903 as indicated by arrows 3950, and corresponding flow of synovial fluid as indicated by arrows 3952. This movement is accompanied by resilient return of protrusion 3922 to its unstressed orientation, as indicated by arrows 3954 and decompression of resilient rim 3918, as indicated by arrows 3956.

It is a particular feature of the construction of articulation portion 3903 and of bone engagement portion 3905 that the application of force 3936 does not cause significant deformation of the geometry of articulation surface 3902.

It is an additional particular feature of the construction of articulation portion 3903 and of bone engagement portion 3905 that wear or deformation of the articulation surface 3902 may be relatively easily remedied by "plug-in" snap fit replacement of the articulation portion 3903 into engagement with the bone engagement portion 3905, which need not necessarily be replaced.

Figure 8B:
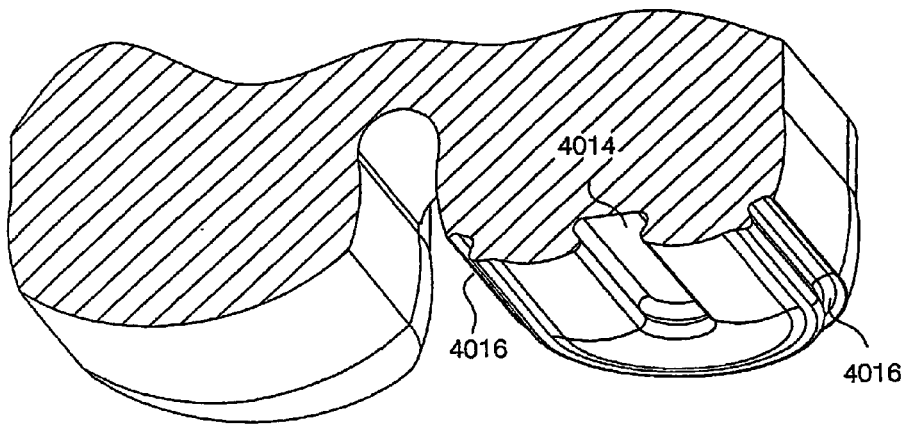
FIGS. 8A and 8B are simplified exploded view illustrations of an implantable artificial femoral surface element assembly constructed and operative in accordance with a preferred embodiment of the present invention.
Figure 8A:
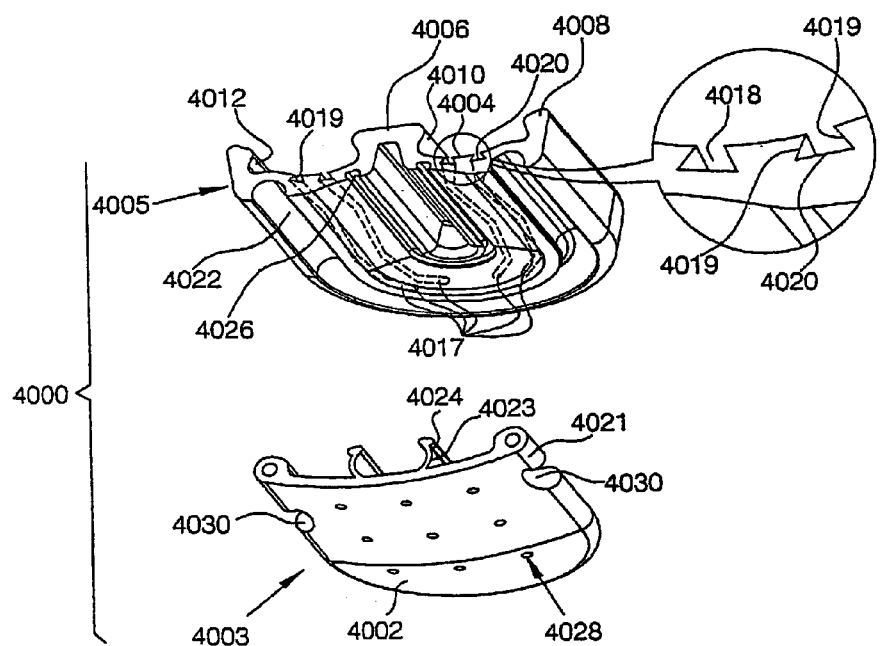
Figure 9:
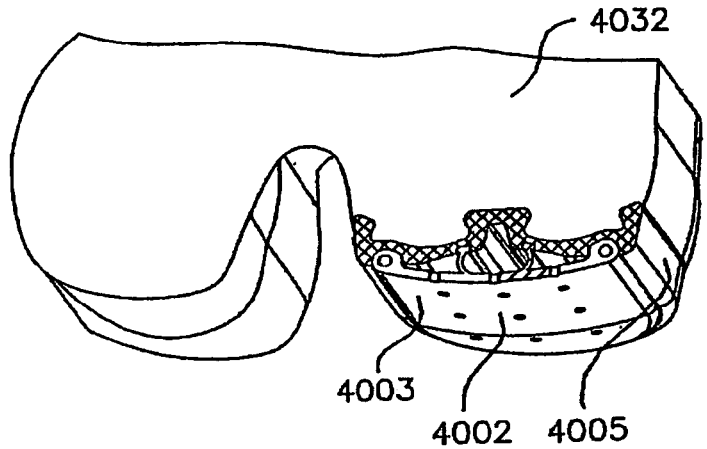
FIG. 9 is a simplified assembled view illustration of the implantable artificial femoral surface element assembly of FIG. 8A mounted onto a tibia in accordance with a preferred embodiment of the present invention.

Reference is now made to FIGS. 8A and 8B, which is a simplified exploded view illustration of an implantable artificial femoral surface element assembly constructed and operative in accordance with a preferred embodiment of the present invention in association with a suitably machined femur and to FIG. 8B, which is a simplified illustration of a femur, suitably machined to receive the implantable artificial femoral surface element assembly of FIG. 8A and to FIG. 9 which is a simplified illustration of implantable artificial femoral surface element assembly assembled unto femur 4032 and constructed and operative in accordance with a preferred embodiment of the present invention.

As seen in FIGS. 8A and 8B, an implantable artificial femoral surface element assembly, designated by reference numeral 4000, is formed preferably by injection molding of a bio stable and bio compatible pliable material such as an elastomer, preferably polyurethane, having mechanical properties which are characterized by a nonlinear stress strain relationship.

Preferably, implantable artificial socket assembly 4000 defines a convex articulation surface 4002, which is defined on an articulation portion 4003, and a bone engagement surface 4004, which is defined on a bone engagement portion 4005. Bone engagement surface 4004 preferably has formed thereon multiple protrusions.

In the illustrated embodiment, there are provided an inner protrusion 4006 and an outer peripheral protrusion 4008, defining respective undercuts 4010 and 4012. Alternatively, protrusions 4006 and 4008 may be any other suitable open or closed protrusions. Protrusions 4006 and 4008 are preferably arranged for snap fit engagement with corresponding grooves 4014 and 4016 provided by machining of a femur medial condyle.

In accordance with a preferred embodiment of the present invention, bone engagement surface 4004 has formed thereon a pattern 4017 defined by a plurality of multidirectional elongate recesses 4018 similar to the pattern 2210 shown in FIG. 4. Alternatively, pattern 4017 may be a hexagonal configuration pattern, similar to pattern 1110 of FIG. 1 or 1210 of FIG. 2, or a spiral configuration pattern similar to pattern 2110 of FIG. 3. Additionally, as described hereinabove, obverse patterns of these patterns or any other suitable configuration pattern may also be provided.

Recesses 4018 are configured with wall surfaces 4019 and a bottom surface 4020. In accordance with a preferred embodiment of the present invention recesses 4018 are configured to have wall surfaces 4019 inclined outwardly toward bottom surface 4020, creating an undercut configuration having a relatively wider cross sectional dimension near the bottom surface and a relatively narrower cross sectional dimension away from the bottom surface.

Articulation portion 4003 is formed with a highly resilient hollow peripheral rim 4021 arranged for snap fit engagement with a corresponding peripheral socket 4022 formed in a surface of bone engagement portion 4005, opposite to bone engagement surface 4004 thereof. Articulation portion 4003 also is formed with a support protrusion 4023, defining an undercut 4024, and arranged for resilient snap fit locking engagement with a corresponding groove 4026 formed in bone engagement portion 4005.

In accordance with a preferred embodiment of the present invention, articulation portion 4003 has formed in articulation surface 4002 a plurality of thoroughgoing apertures 4028 and side openings 4030, which allow synovial fluid to pass therethrough for lubrication of the articulation surface 4002.

It is a particular feature of the embodiment of FIGS. 8A and 8B that when the artificial joint equipped with implantable artificial femoral surface element assembly 4000 experiences forces and/or impacts, such as those having a cyclic nature resulting from walking or running, the resulting stresses and strains exerted within the bone in proximity to the bone engagement surface 4004 induce growth of new bone cells which gradually over time migrate into the recesses 4018. The new bone cells typically press on other cells, creating remodeling of the bone in engagement with bone engagement surface 4004, causing the bone to migrate into the recesses 4018 gradually over time and thus to create an undercut locking engagement with the socket assembly 4000.

It is noted as seen in FIG. 9 and also in FIGS. 10A and 10B below that implantable artificial femoral surface element assembly 4000 assembled unto femur 4032 is shown as an embodiment of the present invention wherein no pattern such as the pattern 4017 is formed on bone engagement surface 4004. The bone engagement surface 4004 may be formed additionally, as described hereinabove, obverse patterns of these patterns or any other suitable configuration pattern or any other non-smooth textures may also be provided.

Figure 10A:
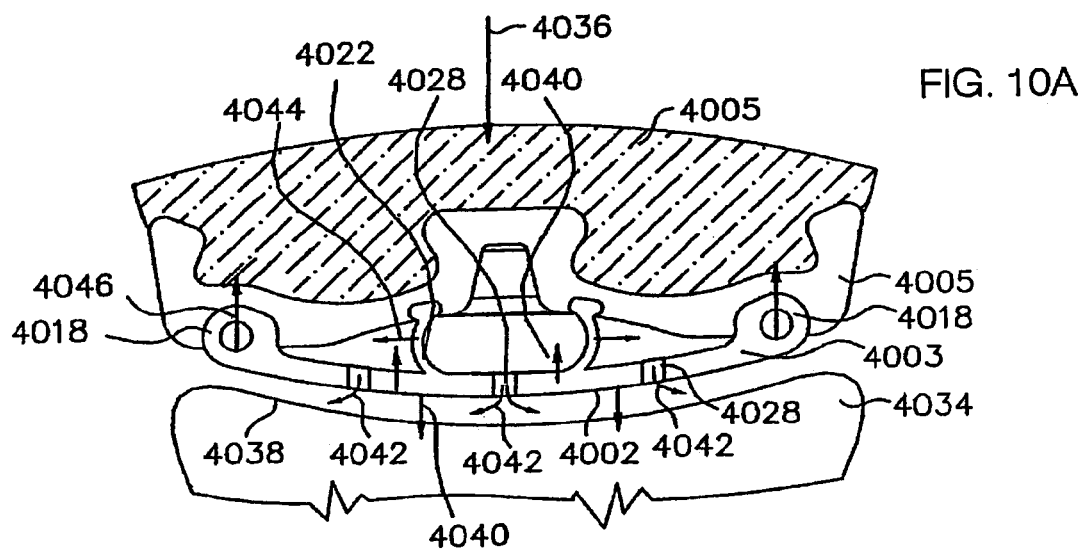
FIGS. 10A and 10B are sectional illustrations showing the implantable artificial tibial socket assembly of FIGS. 8A and 8B and FIG. 9 mounted onto a tibia in two alternative operative orientations.
Figure 10B:
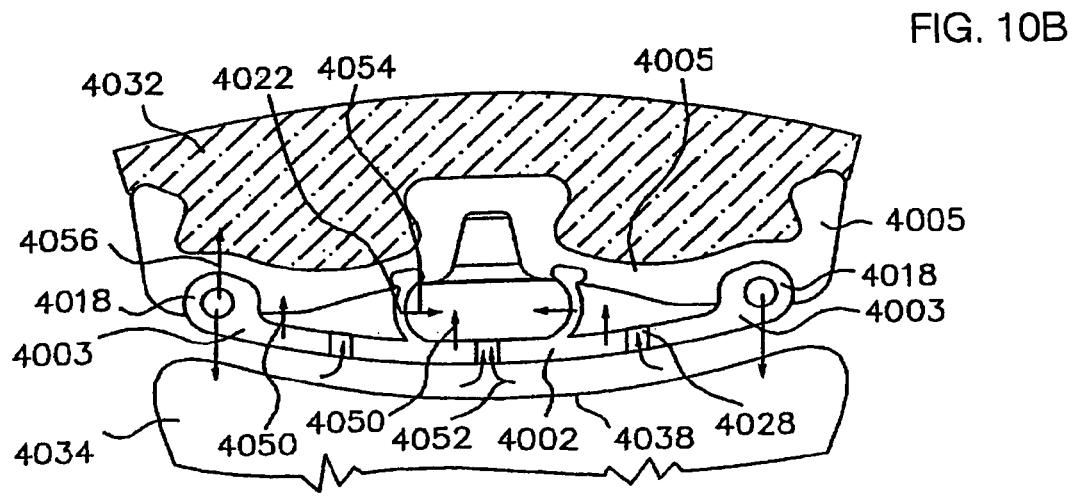

Reference is now made to FIGS. 10A and 10B, which are sectional illustrations showing the implantable artificial femoral surface element assembly of FIG. 8A mounted onto a femoral medial condyle 4032 in two alternative operative orientations. FIG. 10A shows an operative orientation wherein the joint is loaded, e.g. the femur, here designated by reference numeral 4032, presses downward onto the tibia, here designated by reference numeral 4034. The loading force is designated by arrow 4036.

As seen in FIG. 10A, application of force 4036 causes the articulation portion 4003 to be resiliently displaced toward the bone engagement portion 4005, thus causing synovial fluid, located between the articulation portion 4003 and the bone engagement portion 4005 to be forced through apertures 4028 and openings 4030 so as to lie on and over articulation surface 4002 and to provide enhanced lubrication for the articulation of an articulation surface 4038 of tibia 4034 with articulation surface 4002.

Considering FIGS. 10A and 10B, it is seen that the application of force 4036, causes movement of articulation portion 4003 as indicated by arrows 4040, and corresponding flow of synovial fluid as indicated by arrows 4042. This movement is accompanied by resilient buckling of protrusion 4022, as indicated by arrows 4044 and compression of resilient rim 4018, as indicated by arrows 4046.

Release of force 4036 causes movement of articulation portion 4003 as indicated by arrows 4050, and corresponding flow of synovial fluid as indicated by arrows 4052. This movement is accompanied by resilient return of protrusion 4022 to its unstressed orientation, as indicated by arrows 4054 and decompression of resilient rim 4018, as indicated by arrows 4056.

It is a particular feature of the construction of articulation portion 4003 and of bone engagement portion 4005 that the application of force 4036 does not cause significant deformation of the geometry of articulation surface 4002.

It is an additional particular feature of the construction of articulation portion 4003 and of bone engagement portion 4005 that wear or deformation of the articulation surface 4002 may be relatively easily remedied by "plug-in" snap fit replacement of the articulation portion 4003 into engagement with the bone engagement portion 4005, which need not necessarily be replaced.

Figure 11A:
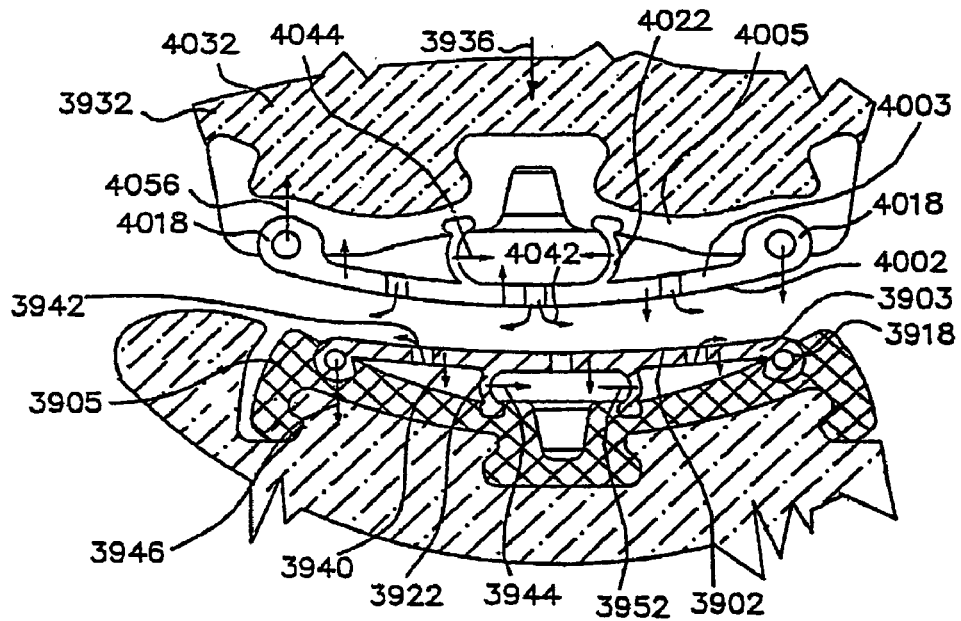
FIGS. 11A and 11B are sectional illustrations showing the implantable artificial tibial socket assembly of FIG. 5A to FIG. 7B and the implantable artificial femoral surface element assembly of FIG. 8A to FIG. 10B in respective first and second operative orientations in a total unicondylar knee replacement environment.
Figure 11B:
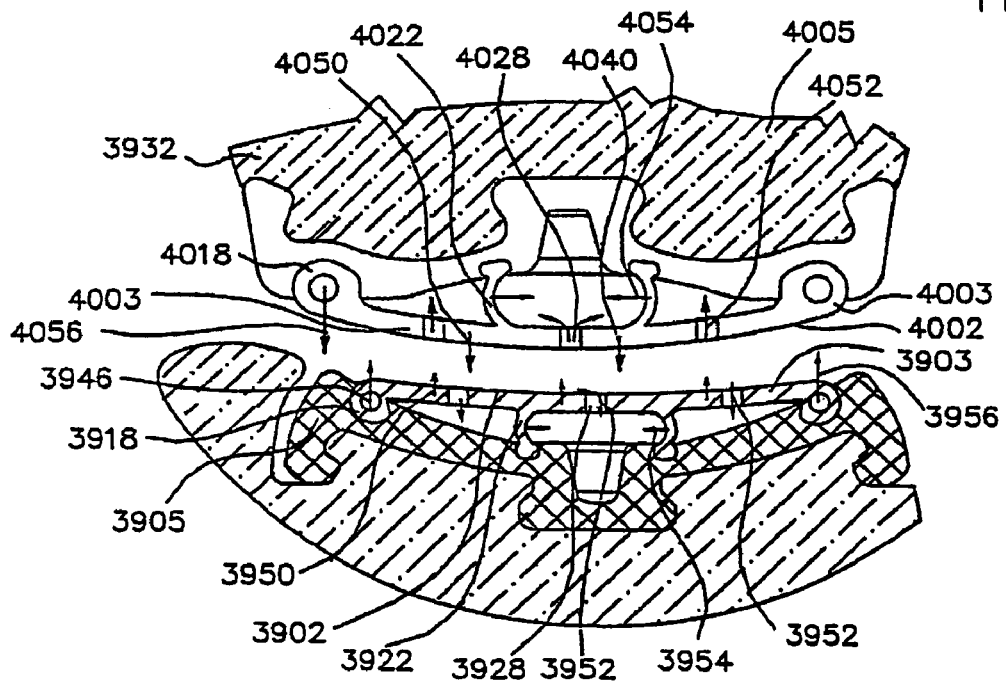

Reference is now made to FIGS. 11A and 11B, which are sectional illustrations showing the implantable artificial tibial socket assembly of FIGS. 5A-7B and the implantable artificial femoral surface element assembly of FIGS. 8A-10B in respective first and second operative orientations in a total unicondylar knee replacement environment.

As seen in FIG. 11A, application of force 3936 causes the articulation portion 3903 to be resiliently displaced toward the bone engagement portion 3905, thus causing synovial fluid, located between the articulation portion 3903 and the bone engagement portion 3905 to be forced through apertures 3928 and openings 3930 so as to lie on and over articulation surface 3902 and to provide enhanced lubrication for the articulation of an articulation surface 3938 of femur 3932 with articulation surface 3902.

It is seen that the application of force 3936, causes movement of articulation portion 3903 as indicated by arrows 3940, and corresponding flow of synovial fluid as indicated by arrows 3942. This movement is accompanied by resilient buckling of protrusion 3922, as indicated by arrows 3944 and compression of resilient rim 3918, as indicated by arrows 3946.

As also seen in FIG. 11A, application of force 3936 causes the articulation portion 4003 to be resiliently displaced toward the bone engagement portion 4005, thus causing synovial fluid, located between the articulation portion 4003 and the bone engagement portion 4005 to be forced through apertures 4028 and openings 4030 so as to lie on and over articulation surface 4002 and to provide enhanced lubrication for the articulation of an articulation surface 4038 of tibia 4034 with articulation surface 4002.

It is noted that the application of force 3936, causes movement of articulation portion 4003 as indicated by arrows 4040, and corresponding flow of synovial fluid as indicated by arrows 4042. This movement is accompanied by resilient buckling of protrusion 4022, as indicated by arrows 4044 and compression of resilient rim 4018, as indicated by arrows 4046.

Release of force 3936 causes movement of articulation portion 3903 as indicated by arrows 3950, and corresponding flow of synovial fluid as indicated by arrows 3952. This movement is accompanied by resilient return of protrusion 3922 to its unstressed orientation, as indicated by arrows 3954 and decompression of resilient rim 3918, as indicated by arrows 3956.

Release of force 3936 also causes movement of articulation portion 4003 as indicated by arrows 4050, and corresponding flow of synovial fluid as indicated by arrows 4052. This movement is accompanied by resilient return of protrusion 4022 to its unstressed orientation, as indicated by arrows 4054 and decompression of resilient rim 4018, as indicated by arrows 4056.

It is a particular feature of the construction of articulation portion 3903 and of bone engagement portion 3905 that the application of force 3936 does not cause significant deformation of the geometry of articulation surface 3902.

Similarly, it is a particular feature of the construction of articulation portion 4003 and of bone engagement portion 4005 that the application of force 3936 does not cause significant deformation of the geometry of articulation surface 4002.

It is an additional particular feature of the construction of articulation portion 3903 and of bone engagement portion 3905 that wear or deformation of the articulation surface 3902 may be relatively easily remedied by "plug-in" snap fit replacement of the articulation portion 3903 into engagement with the bone engagement portion 3905, which need not necessarily be replaced.

Similarly, is an additional particular feature of the construction of articulation portion 4003 and of bone engagement portion 4005 that wear or deformation of the articulation surface 4002 may be relatively easily remedied by "plug-in" snap fit replacement of the articulation portion 4003 into engagement with the bone engagement portion 4005, which need not necessarily be replaced.

It is appreciated that the structures and methodology described hereinabove with reference to FIGS. 5A-11B are applicable not only to the medial condyle but also equally to the lateral condyle.

In another preferred embodiment of the present invention, the structures and methodology described hereinabove with reference to FIGS. 5A-11B are applicable by employing bone engagement portion 3905 as a "tibia surface element" utilizing the bone side configuration and construction of bone engagement portion 3905 for anchoring it to the tibia and also providing another configuration on the articulation side of bone engagement portion 3905 for operating in an articulation mode with the femur articulating surface.

In yet another preferred embodiment of the present invention, the structures and methodology described hereinabove with reference to FIGS. 5A-11B are applicable by employing bone engagement portion 4005 as a "femur surface element" utilizing the bone side configuration and construction of bone engagement portion 4005 for anchoring it to the femur and also providing another configuration on the articulation side of bone engagement portion 4005 for operating in an articulation mode with the tibia articulating surface.

Reference is now made to FIGS. 60, 61, 62 and 63, which are meshed sectional illustrations of the first, second, third and fourth (final) stages in press fit and snap fit installation of an implantable artificial socket 5400, of a similar type to implantable artificial sockets 1100 shown hereinabove in FIG. 1 and/or 1200 shown hereinabove in FIG. 2 and/or 2100 shown hereinabove in FIG. 3 and/or 2200 shown hereinabove in FIG. 4 or similar types, in a machined acetabulum 5420 in accordance with a preferred embodiment of the present invention wherein snap fit and press fit engagement situation with the machined acetabulum the dimensions and configuration of one or both of the implantable artificial socket 5400 and the machined acetabulum 5420 are such that both snap fit and press fit engagement are provided.

Figure 60:
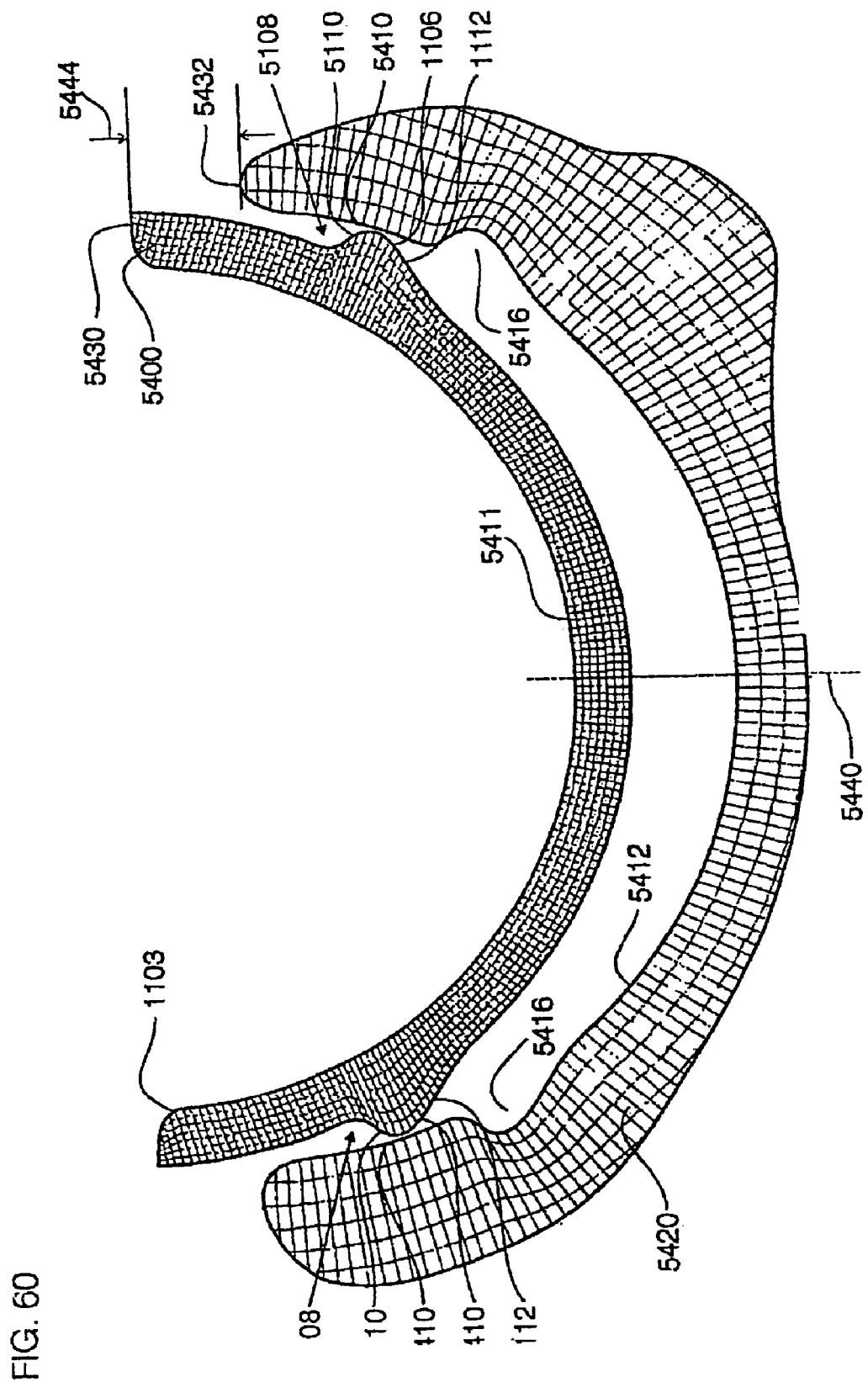
FIG. 60 is a simplified meshed sectional illustration of a first stage in a press fit and snap fit installation of an implantable artificial socket in a reamed acetabulum in accordance with a preferred embodiment of the present invention.

As seen in FIG. 60 in the first stage in press fit and snap fit installation of an implantable artificial socket 5400 in a machined acetabulum 5420 a surgeon, preferably using his fingers, gently introduces the artificial acetabulum socket into position machined acetabulum. At the positioning stage shown in FIG. 60, there is provided an implantable artificial socket 5400 having an annular outwardly extending protrusion 5406, which lies in touching, generally non-compressive engagement with an annular portion 5410 of a generally spherical inner concave surface 5412 of a machined acetabulum 5420. Annular portion 5410 lies above a groove 5416, formed in generally spherical inner concave surface 5412, which is designed to receive protrusion 5406. Accordingly, engagement of protrusion 5406 with annular portion 5410 causes the implantable artificial acetabulum socket 5400 to rest at a position wherein an outer edge thereof, designated by reference numeral 5430 lies above a corresponding outer edge 5432 of machined acetabulum 5420. The separation between the planes of outer edge 5430 of implantable artificial acetabulum socket 5400 and of outer edge 5432 along their mutual axis of symmetry 5440 is indicated by arrows 5444.

As can be seen at the positioning stage shown in FIG. 60, which is the first step of the snap fit and press fit engagement, from a consideration of the meshed sectional illustration of FIG. 60, substantially no stress is applied to the implantable artificial acetabulum socket 5400 and to machined acetabulum 5420 by the engagement thereof.

Figure 61:
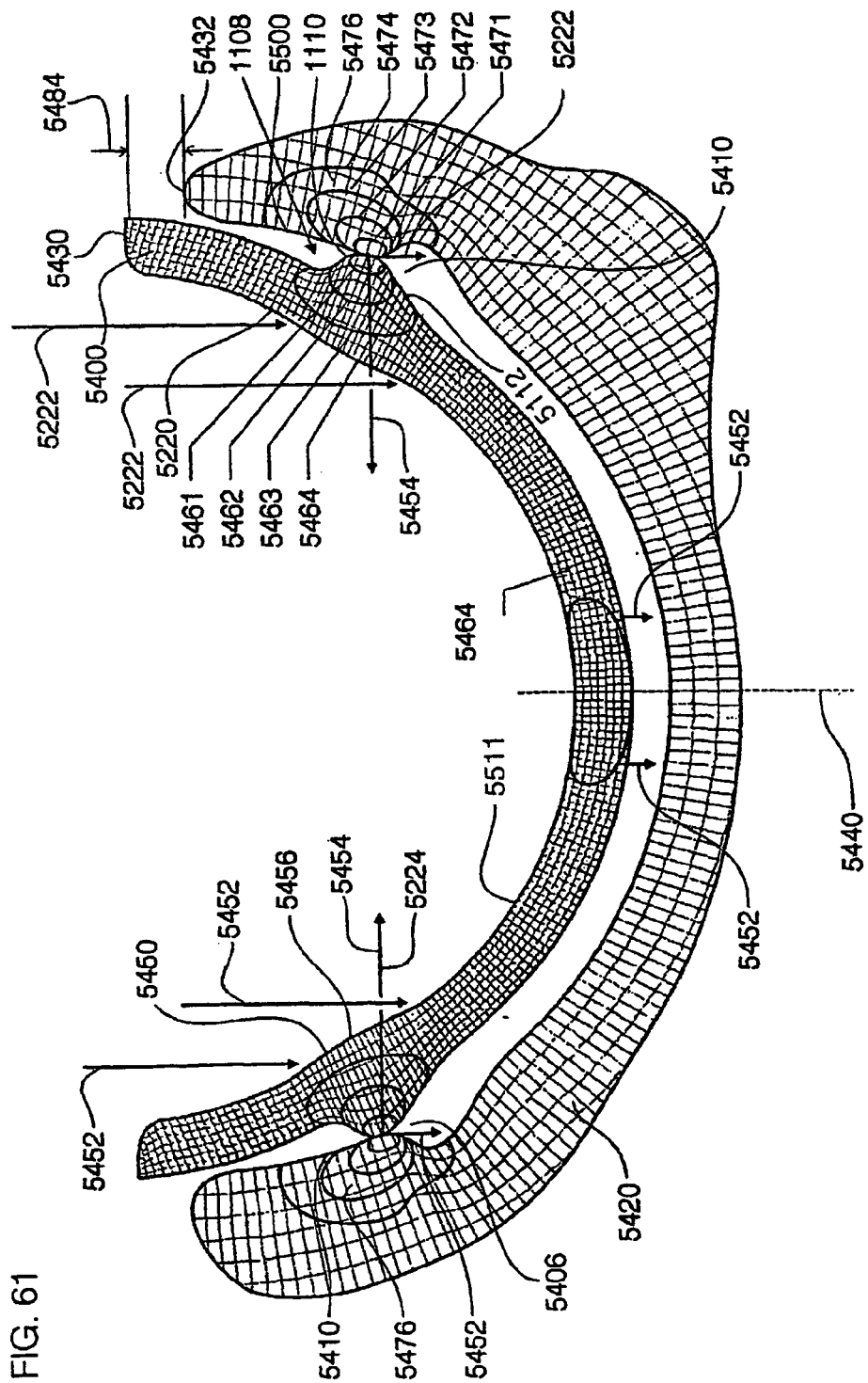
FIG. 61 is a simplified meshed sectional illustration of a second stage in a press fit and snap fit installation of an implantable artificial socket in a reamed acetabulum in accordance with a preferred embodiment of the present invention, showing stress fields.

Reference is now made to FIG. 61, which is a meshed sectional illustration corresponding the second step of the snap fit and press fit engagement following placement of implantable artificial acetabulum socket into position as described hereinabove with reference to FIG. 60. At this second step the surgeon, preferably using his fingers, gently engages the artificial acetabulum socket 5400 preferably at locations, designated in FIG. 61 by reference numeral 5450 on inner concave surface 5511 thereof and presses thereon in a direction indicated by arrows 5452, which direction lies generally along axis 5440.

As seen in FIG. 61, the application of this pressure causes displacement of artificial acetabulum socket 5400 in direction 5452. Due to the concave configuration of surface 5412 at annular surface portion 5410, this displacement produces radially inward compression of artificial acetabulum socket 5400 at protrusion 5406, as indicated by arrows 5454. This radially inward compression results in deformation of the artificial acetabulum socket 5400 at protrusion 5406 and in the general region thereof, as indicated, inter alia by arrows 5456.

The racially inward compression and the resulting deformation of artificial acetabulum socket 5400 produces stresses in the acetabulum socket 5400, as illustrated, inter alia, by stress contour lines 5461, 5462, 5463 and 5464. The above-described engagement of artificial acetabulum socket 5400 with the machined acetabulum 5420 causes forces to be applied to the machined acetabulum 5420, producing compression stresses therein, as illustrated, inter alia, by stress contour lines 5471, 5472, 5473 and 5474 in a region designated by reference numeral 5476, in the vicinity of annular surface portion 5410. It is appreciated that the stresses thus produced in machined acetabulum 5420 produce corresponding strains therein. Both the stresses and the strains have positive medical implications, as will be discussed hereinbelow.

Displacement of artificial acetabulum socket 5400 in direction 5452 is seen to reduce the separation between the planes of outer edge 5430 of implantable artificial acetabulum socket 5400 and of outer edge 5432 along axis 5440, indicated by arrows 5484.

Figure 62:
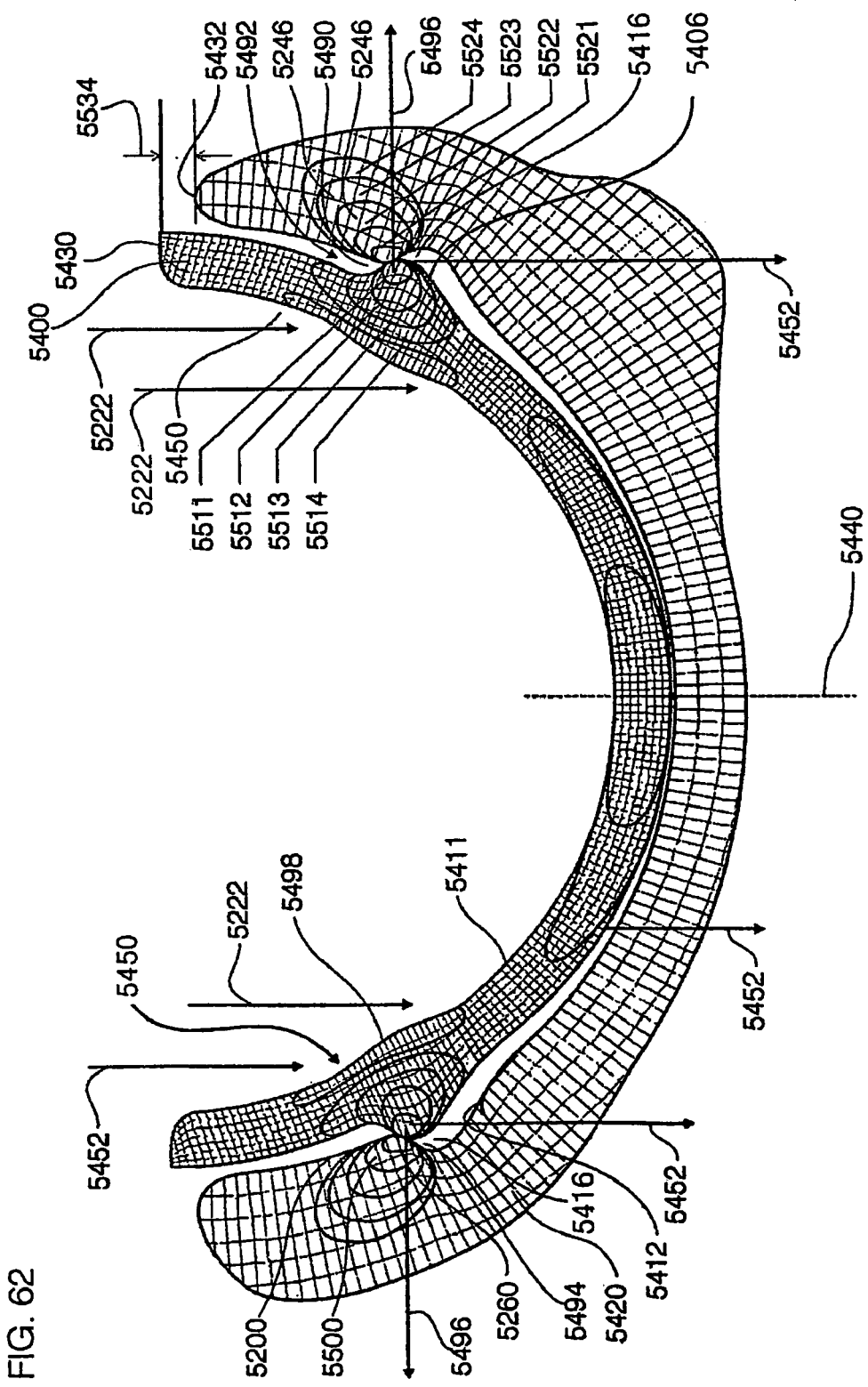
FIG. 62 is a simplified meshed sectional illustration of a third stage in a press fit and snapfit installation of an implantable artificial socket in a reamed acetabulum in accordance with a preferred embodiment of the present invention, showing stress fields.

Reference is now made to FIG. 62, which is a meshed sectional illustration corresponding to the third step of the snap fit and press fit engagement following second step as described hereinabove with reference to FIG. 61. At this stage the surgeon, preferably using his fingers, presses further on the artificial acetabulum socket 5400 preferably at locations, designated by reference numeral 5450 on inner concave surface 5411 thereof in the direction indicated by arrows 5452.

As seen in FIG. 62, the application of this further pressure, causes further displacement of artificial acetabulum socket 5400 in direction 5452. This further displacement produces sliding pressure engagement between underlying surface portion 5490 of protrusion 5406 at the undercut 5492 and a radially outward extending surface portion 5494 of groove 5416. It is noted that the resiliency of the artificial acetabulum socket 5400 causes radially outward displacement of protrusion 5406, as indicated by arrows 5496. The resulting radially outward decompression results in different deformation of the artificial acetabulum socket 5400 at protrusion 5406 and in the general region thereof, as indicated, inter alia by arrows 5498.

This results in reduced and changed stress patterns in both the artificial acetabulum socket 5400 and in the machined acetabulum 5420 at region 5500 thereof, as indicating by stress contour lines 5511, 5512, 5513 and 5514 in artificial acetabulum socket 5400 and by stress contour lines 5521, 5522, 5523 and 5524 in machined acetabulum 5420.

The further displacement of artificial acetabulum socket 5400 in direction 5452 is seen to further reduce the separation between the planes of outer edge 5430 of implantable artificial acetabulum socket 5400 and of outer edge 5432 along axis 5440, indicated by arrows 5534.

Figure 63:
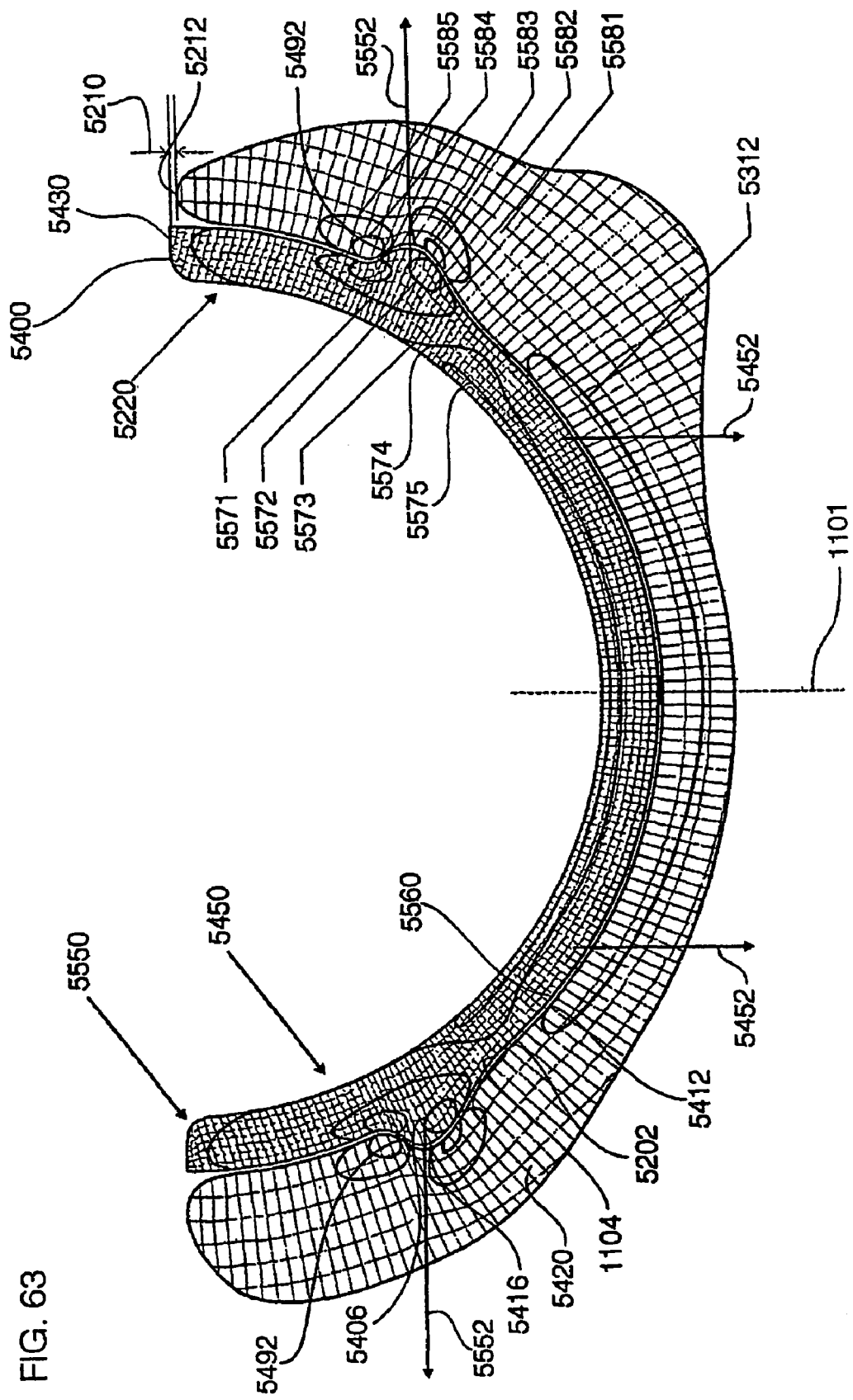
FIG. 63 is a simplified meshed sectional illustration of a final stage in a press fit and snap fit installation of an implantable artificial socket in a reamed acetabulum in accordance with a preferred embodiment of the present invention, showing stress fields.

Reference is now made to FIG. 63, which is a meshed sectional illustration corresponding to the fourth and final step of the snap fit and press fit engagement following third step as described hereinabove with reference to FIG. 62. At this stage the surgeon, preferably using his fingers, now presses on the artificial acetabulum socket 5400 preferably at locations, designated by reference numeral 5550 on edges 5430 thereof in the direction indicated by arrows 5452.

As seen in FIG. 63, the application of this further pressure, causes further displacement of artificial acetabulum socket 5400 in direction 5452. This further displacement produces sliding snap fit and press fit engagement between protrusion 5406 and groove 5416.

It is noted that the resiliency of the artificial acetabulum socket 5400 causes radially outward displacement of protrusion 5406, as indicated by arrows 5552. The resulting radially outward decompression generally eliminates deformation of the artificial acetabulum socket 5400 at protrusion 5406 and in the general region thereof designated by reference numeral 5450.

It is noted that the snap fit and press fit engagement shown in FIG. 63 produces pressure engagement between concave surface 5412 of the machined acetabulum 5420 and the convex facing surface 5560 of artificial acetabulum socket 5400, generally along the entire extent thereof. Accordingly the stresses in both the acetabulum socket 5400 and in the machined acetabulum 5420 are generally greater and are not localized in the region of the snap fit engagement therebetween or limited to that region as indicated by stress contour lines 5571, 5572, 5573, 5574 and 5575 in artificial acetabulum socket 5400 and by stress contour lines 5581, 5582, 5583, 5584 and 5585 in acetabulum 5420.

It is also appreciated that the snap fit and press fit engagement of the artificial acetabulum socket 5400 with the machined acetabulum 5420 produces locking of the artificial acetabulum socket 5400 in groove 5416, wherein undercut 5492 prevents disengagement of protrusion 5406 from groove 5416.

It is known in the art that "bone adaptation is likely to be responsive to a range of factors that constitute the "load history" such as strain magnitude, cycle number, frequency etc. Such adaptive response has recently been proposed as being over the short term. With regards the long term "load history" it is hypothesized that bone response to strains within a certain range induce bone modeling and remodelling but that such activity is followed by a quiescent period. It has also been suggested that bone has memory and will adapt to previous stimuli. Thus it can be stated that bone adaptation is both spatially and temporally regulated, by a small subset of the "loading history" and that frequency may be more important than magnitude, whereby high rates of loading result in an increase in interfacial stiffness with an implant, by means of bone remodelling and an overall increase in bone mass. The influence of increased stiffness on fluid movement within cannaliculi will further alter the stimulation of osteocytes which in turn impact upon the relay mechanism for load bearing stimuli." From publication Journal of Prosthetic Dentistry—Vol. 81 No. 5 pp 553-561 "Toward an understanding of implant occlusion and strain adaptive bone modeling and remodeling" by Stanford C.-Brand R. May 1999.

It is further known in the art that species such as humans, eagles, sharks and tigers all model and remodel their bones to configuration and size for sustaining close to exactly the same strain in their bone substance when engaged in their normal physical activity.

It is further known in the art that bone remodeling mechanism is a function of mechanical & environmental conditions wherein cells subjected to specific mechanical and environmental conditions would transform into a specific type of bone tissue for example as a function of micro strain ranges. At a first active strain range no cell growth occurs and at a second active strain range cancellous cell growth occurs and at a third active strain range cartilage cell growth occurs and at a fourth active strain range cortical cell growth occurs and at a fifth active strain range irreversible damage of bone occurs, as published by Binderman I et al: Calcified Tissue International 1988; 42: 261-267;

It is further known in the art that cells subjected to compression and low oxygen tensions would develop into chondroblasts and cartilage and that cells subjected to constant compressive stresses [hydrostatic stress] inhibit endochondral ossification=>Cartilage and that cells subjected to compressive hydrostatic pressures greater than about 0.15 MPa and strains less than about 15% stimulate enchondral ossification, as published by Yasui N et al: J Bone Joint Surg 1997; 79B: 824-830;

As illustrated in FIG. 63 the stress fields produced for a situation where the dimensions and configuration of one or both of the implantable artificial socket 5400 and the machined acetabulum 5420 of a patient are such that both snap fit and press fit engagement are provided. The stress fields produced by the snap fit and press fit engagement are shown distributed within the substance of implantable artificial socket 5400 and within certain regions of the substance of the bone of acetabulum 5420.

As will be discussed hereinbelow in FIGS. 75A, 75B, 76A, 76B; 77A, 77B, 78A and 78B additional stress fields may be superimposed onto the stress fields produced by the snap fit and press fit engagement by external loading exerted on an artificial hip joint constructed and operative in accordance with a preferred embodiment of the present invention resulting combined stress fields produced by both the external loads and the stresses produced by the snap fit and press fit installation of an implantable artificial socket 5420 operative as a component of said hip joint.

It is further appreciated that the implants of the present invention are constructed to control the stress and strain distribution at the bone-implant interface, and within the substance of the surrounding bone, resulting in a positive bone remodeling, creating a mechanical environment with conditions that initiate net remodeling activity growing new bone cells of structural characteristics. As described hereinbelow the implants of the present invention are constructed to control the strain distribution by targeting specific locations within the bone substance to be subjected to desired strain.

In accordance with preferred embodiments of the present invention, artificial sockets such as implantable artificial socket 5420, as well as other prostheses described in embodiments of this invention, any combination of the design parameter grouped in following parenthesis (design loading on the prostheses described in this invention; and the configuration and construction of the prostheses described in this invention; and of the mechanical properties of the bio stable and bio compatible pliable material from which the prostheses are formed described in this invention; and of insertedly molded in the prostheses of deformation control elements described in this invention) and employed by persons skilled in the art produce desired controlled deformations within the prosthesis. Under these combined conditions desired controlled deformations produced within the prosthesis substance are associated with the transmission of compression stress of desired magnitude distributed in desired region within the prosthesis.

It is appreciated by persons skilled in the art that with the stress fields shown in FIG. 63 there are also associated strain fields. It is for purpose of clarity only that only one type of field is shown in FIG. 63, and in other embodiments described in this invention, as is the case also in descriptions of the entirety of the embodiments of this invention while associated strain fields are known to exist where stress fields do exist but are not specifically shown.

It is a particular feature of the construction of the pliable implants described in this invention that loading exerted on an implant at a specific location results in deformations and compression stress fields in a number of regions of the implant including regions remote from the loading application region.

This feature is partially comparable in principle (for further clarification only) to fluid behavior as in terms of hydrostatic pressure distribution generated by pressurized fluid within a container (rigid or flexible) and wherein the outer surfaces of the prosthesis are comparable to the walls of said example pressurized container and wherein the pressure distribution within an implant substance differs from said example by not being uniform in the manner found in a pressurized vessel. When example container is by further example of a flexible construction such as in a water bed, the loading by a person's weight lying on the bed results in uniform pressure remote from the lying person's location. This feature is further compared (for further clarification only) in principle to fluid behavior as in terms of flow within conduits. Said example fluid flow is influenced by adequate cross section of the example conduit which effects effortlessness of fluid flow or by sharp turns and by locally narrowed passageways which hinder the flow in the conduit.

In actual implant configuration there is also provided in accordance with preferred embodiments described in this invention adequate thickness of the implants (which are the parallel to the conduit cross section example) and there are also avoided sharp geometrical turns and folds and locally narrowed thickness (which are compared to the impediments caused by sharp turns and locally narrowed passageways which hamper the flow in the example conduit) and thus optimal control is achieved of deformations and compression stress field in desired regions of the implant including regions remote from the loading application region and which further exert, as described hereinabove, desired strain for effecting positive bone adaptation in response to said exerted load on the implant.

As seen hereinabove in FIGS. 60, 61, 62 and 63 implantable artificial socket 5400, is installed in a machined acetabulum 5420 in accordance with a preferred embodiment of the present invention wherein both snap fit and press fit engagement are provided for the socket 5400 with the machined acetabulum 5420 producing mechanical locking fixation of the artificial acetabulum socket 5400 in groove 5416, wherein undercut 5492 prevents disengagement of protrusion 5406 from groove 5416.

It is known in the art that in the vicinity of rigid implants, such as metal implants, there are regions of stress shielding in some parts of the bone, meaning that such rigid implants take load formerly transferred to the bone, thereby shielding the bone from the load and causing bone resorption. Bone resorption results in remodeling the bone geometry which is the cause in many cases to implant loosening. This process has been observed in regions such as in the proximal medial bone after hip replacement, and such as under the tibial component of knee replacements.

Avoidance of bone resorption and deterioration and loss of bone geometry responsible for sustaining the long term effectiveness of the mechanical locking fixation of the artificial acetabulum socket 5400 is brought about by the implant strain control in accordance with this invention described hereinabove and more specific by the targeting of specific locations within the bone substance to be subjected to desired strain as is taught to promote bone regeneration and strengthening as detailed in bibliography known in the art cited hereinabove as opposed to the bone resorption and deterioration phenomena common in prior art devices.

It is noted that the snap fit and press fit engagement shown in FIG. 63 produces pressure engagement between concave surface 5412 of the machined acetabulum 5420 and the convex facing surface 5560 of artificial acetabulum socket 5400, generally along the entire extent thereof. Accordingly the stresses in both the acetabulum socket 5400 and in the machined acetabulum 5420 are generally greater and are not localized in the region of the snap fit engagement therebetween or limited to that region as indicated by stress contour lines 5571, 5572, 5573, 5574 and 5575 in artificial acetabulum socket 5400 and by stress contour lines 5581, 5582, 5583, 5584 and 5585 in acetabulum 5420.

As seen hereinabove in FIGS. 60, 61, 62 and 63 implantable artificial socket 5400, of a similar type to implantable artificial sockets 1100 shown hereinabove in FIG. 1 and/or 1200 shown hereinabove in FIG. 2 and/or 2100 shown hereinabove in FIG. 3 and/or 2200 shown hereinabove in FIG. 4 or similar types are installed in a machined acetabulum 5420 in accordance with a preferred embodiment of the present invention.

In another preferred embodiment of the present invention implantable artificial socket 5400 is of type wherein the convex bone engagement surface is preferably configured with a partial configuration pattern on a very limited area of the convex bone engagement surface, or alternatively in another preferred embodiment of the present invention implantable artificial socket 5400 is of type wherein the convex bone engagement surface is preferably not configured with any configuration pattern. Such embodiments of the present invention are particularly suitable for patients with limited mobility and who are only capable of low level of activity. For this type of patient the stress fields produced for a situation of wherein both snap fit and press fit engagement are provided as illustrated hereinabove in FIG. 63 are sustained for most of the patient's life and wherein no significant superimposed stresses exerted by external load resulting from the patient's level of activity are superimposed for any considerable periods of time of the patient's life. This is the case of patients with limited mobility and who are only capable of low level of activity.

Reference is now made to FIGS. 64A and 64B are respective pictorial and partially cut away illustrations of a bone engaging interface of an implantable tooth implant assembly constructed and operative in accordance with a preferred embodiment of the present invention; which is particularly suitable for use in a dental fixture and as an artificial periodontal ligament replacement.

As seen in FIGS. 64A and 64B, a bone engaging interface of an implantable dental implant, designated by reference numeral 5750, is formed preferably by injection molding of polyurethane. Preferred polyurethane materials are described hereinbelow.

Preferably, bone engaging interface of an implantable tooth implant assembly 5750 is of generally uniform thickness, is symmetric about an axis 5751 and defines a concave inner fixture anchoring surface 5752, having a beveled edge 5753, and there is also provided on fixture anchoring surface 5752 a recess 5754 matched with a protrusion 5662 provide on a fixture 5660 for snap fit engagement with bone engaging interface of an implantable tooth implant assembly fixture designated by reference numeral 5660. Bone engaging interface of an implantable tooth implant assembly 5750 has a generally convex outer bone engagement surface 5754 which preferably has formed thereon at any suitable location between its apex and its rim at least one generally annular outwardly extending protrusion 5756, preferably defining a generally annular undercut 5758. Alternatively, the protrusion 5756 may be any other suitable non-annular, open or closed, generally peripheral protrusion. The protrusion 5756 is preferably arranged for snap fit engagement with a corresponding groove formed by machining of a jaw bone.

There is also provided in accordance with a preferred embodiment of the present invention a method for implanting a peripheral and continuous recess (not shown) between the protrusion 5756 and the rim of bone engaging interface of an implantable tooth implant assembly 5750. The bone remodeling process described hereinabove results in the migration of bone cells into said peripheral and continuous recess and thus creates a peripheral continuous seal operative as a barrier separating the germ filled oral cavity from the sterile bone and blood supply underneath.

Preferably, the protrusion 5756 has a cross-sectional configuration, which is characterized in that an underlying surface portion 5760 of protrusion 5756, at the undercut 5758, defines a slope which is sharper than a corresponding slope of an overlying surface portion 5762 of protrusion 5756.

It is a particular feature of the bone engaging interface of an implantable tooth implant assembly 5750 that it is constructed from a single layer, preferably, molded of a polyurethane of durometer number 80 shore A, and includes an inserted internal deformation control element 5776, illustrated pictorially in FIG. 64B. The deformation control element 5776 is preferably constructed of a rigid material such as metal or composite material. Preferably control element 5776 is molded of a relatively rigid polyurethane, typically one having a Shore hardness of approximately 70D, and may have carbon whiskers embedded therein. Alternatively the deformation control element 5776 is preferably formed of woven high performance fibers such as carbon fibers, KEVLAR®, DYNEEMA®, and glass fibers.

Preferably, deformation control element 5776 is configured and insertably positioned within bone engaging interface of an implantable tooth implant assembly 5750 with portions of PU material of the single molded layer covering it outwardly, inwardly and towards the rim of bone engaging interface of an implantable tooth implant assembly 5750.

The deformation control element 5776 preferably has an overall generally annular configuration defined by a web portion 5782, a first thickened portion 5784, having a circular cross section, and a second thickened portion 5786, having a circular cross section. Deformation control element 5776 is further defined by rectangular cut-outs 5792 separated by flaps 5794 which terminate in thickened portions 5784 which are also separated by cut-outs 5792. Alternatively first thickened portion 5784 and second thickened portion 5786 having a non circular cross section.

In another preferred embodiment of the present invention bone engaging interface of an implantable tooth implant assembly 5750 is preferably incorporating a reinforcement 5798 constructed of high performance fibers such as carbon fibers, Kevlar®, Dyneema®, and glass fibers. Bone engaging interface of an implantable tooth implant assembly 5750 reinforced by fiber reinforcement 5798 imitates the function of the periodontal ligament which is constructed in nature with structural fiber tissue and which encapsulate a natural tooth.

It is a particular feature of the configuration and construction of bone engaging interface of an implantable tooth implant assembly 5750 according to the principle detailed hereinabove (for further clarification only) to enable fluid flow within conduits, providing adequate cross section avoiding sharp turns and locally narrowed "passageways" which hinder transforming deformation and compression stresses to various portions of bone engaging interface of an implantable tooth implant assembly 5750. This construction and configuration of bone engaging interface of 5750 ensure also that the placing therein of fiber reinforcement 5798 is done in a continuous orientation wherein individual fibers and woven fibers are not bent in sharp turn or sharply warped. Continuity of reinforcement fibers allows said fibers to function optimally in tension.

In another preferred embodiment of the present invention, bone engaging interface of an implantable tooth implant assembly 5750 is configured and constructed from material layers and reinforcement, providing shock absorbing characteristics, allowing a small amount of movement of the tooth in response to moments and forces and impacts of the three phases of the masticatory cycle (chewing): the preparatory phase and the crushing phase and the gliding (grinding) phase. Even though shock absorbing is the most important role of the natural periodontal ligament it is removed during operation which caused stress concentration and micro-fractures in alveolar bone.

It is appreciated that the present invention resolve problems associated with the removal of the periodontal ligament in operation. Without periodontal dental implant lacks the sensory advantages of a natural tooth. The dental implant is unable to adapt to occlusal trauma resulting trauma in microfractures of the crestal bone and bone resorption, and chronic screw loosening of the screw-retained prosthesis, porcelain fracture, unseating of attachments, excessive occlusal wear, denture sores, purulence, redness, swelling and patient discomfort.

Bone engaging interface 5750 replaces the periodontal ligament and is constructed and operational for replacing the lost shock absorbing function of the periodontal ligament and restores natural capabilities of a natural healthy tooth.

In accordance with another preferred embodiment of the present invention the relationship between the form and the dimensions of bone engaging interface of an implantable tooth implant assembly 5750 and the protrusion 5760 are, with respect to the form and the dimensions of the corresponding machined jaw bone, preferably arranged for press fit and snap fit engagement with the jaw bone. The press fit feature is typically provided by making the outer dimensions of bone engaging interface 5750 slightly larger than the corresponding dimensions of the machined jaw bone surface onto which the interface fits.

The convex bone engagement surface 5754 is preferably configured with a pattern 5600 preferably defined by a plurality of multidirectional generally radially extending elongate recesses 5614. Recesses 5614 are defined by wall surfaces 5616 and a bottom surface 5620. In accordance with a preferred embodiment of the present invention, recesses 5614 are configured with wall surfaces 5616 being inclined outwardly toward the bottom surface 5620, creating an undercut configuration having a relatively wider cross sectional dimension near the bottom surface and a relatively narrower cross sectional dimension away from the bottom surface.

It is a particular feature of the embodiment of FIG. 64A that when bone engaging interface of an implantable tooth implant assembly 5750 equipped with implantable dental implant fixture designated by reference numeral 5660 experiences forces and/or impacts, such as those having a cyclic nature resulting from the masticatory cycle, the resulting stresses and strains exerted within the jaw bone in proximity to the bone engagement surface 5754 induce growth of new bone cells, which, gradually, over time, migrate into the recesses 5614. The new bone cells typically press on other cells, creating remodeling of the bone in engagement with bone engagement surface 5754, causing the bone to migrate into the channels 5614 gradually, over time, and thus create an undercut locking engagement with the interface 5750. Same process causing bone to migrate into the peripheral and continuous recess mentioned hereinabove and thus create a peripheral continuous seal operative as a barrier separating the germ filled oral cavity from the sterile bone and blood supply underneath.

In accordance with another preferred embodiment of the present invention, the convex bone engagement surface 5775 is preferably configured with a configuration pattern similar to any configuration pattern such as configuration pattern as shown in FIGS. 1-5.

In accordance with yet another preferred embodiment of the present invention, the generally annular outwardly extending protrusion 5760 is preferably configured with a configuration pattern similar to the configuration pattern 5600 or configured with a pattern made of pattern segments similar to the configuration pattern 5600.

Still further in accordance with a preferred embodiment of the present invention, preferably at least two ridge elements 5632 are integrally formed with rim 5630 of bone engaging interface of an implantable tooth implant assembly 5750. The grip element 5630 preferably has an overall generally segmented or continuous annular configuration. Grip element 5630 is shown in FIG. 64A as a segmented annular configuration defined by a web portion 5634 and thickened portion 5636. Grip ridge elements 5632 are constructed operatively in accordance with still another preferred embodiment of the present invention as described in FIGS. 65A and B hereinbelow to be gripped by the jaws of an implanter tool which may be provided for the surgeon to perform the implanting of implantable tooth implant assembly 5650.

FIG. 65A is a sectional illustrations of an implantable tooth implant assembly 5650 mounted onto a jaw 5661 bone and FIG. 65B is a sectional illustrations of an implantable tooth implant assembly 5651 mounted onto a jaw bone 5661 in accordance with a preferred embodiments of the present invention; constructed and operative in accordance with a preferred embodiment of the present invention and which is particularly useful for shock absorbing and sealed fixation to the jaw bone.

In accordance with a preferred embodiment of the present invention as seen in FIG. 65A dental crown prosthesis 5654 is mounted on crown abutment 5658 preferably constructed from a shock absorbing material and operative in accordance with a preferred embodiment of the present invention as a shock absorber for crown prosthesis 5654. Crown abutment 5658 is fixed into fixture designated by numeral 5660. Fixture 5660 is fixed into bone engaging interface of an implantable tooth implant assembly 5750 detailed in FIGS. 64A and B.

Preferably in accordance with a preferred embodiment of the present invention, dental crown prosthesis 5654 is formed with a mounting cavity having an abutment engaging surface 5664 formed with a generally annular inwardly extending protrusion 5668. In accordance with a preferred embodiment of the present invention dental crown prosthesis 5654 is snap fitted onto crown abutment 5658 wherein a protrusion element 5668 is snap fitted onto a matching recess 5670 formed on crown abutment 5658 engaging surface.

In accordance with a preferred embodiment of the present invention crown abutment 5658 is fixed into fixture designated by numeral 5660, or alternatively snap fitted onto bone engaging interface, or alternatively snap fitted and press fitted onto bone engaging interface, or alternatively is mounted onto bone engaging interface by a bayonet-type connection, or alternatively screwed onto bone engaging interface and wherein threaded configuration is provided on matching engagement surfaces of both crown abutment 5658 and Fixture 5660.

In accordance with a preferred embodiment of the present invention fixture 5660 is press fitted onto bone engaging interface, or alternatively snap fitted onto bone engaging interface, or alternatively snap fitted and press fitted onto bone engaging interface, or alternatively is mounted onto bone engaging interface by a bayonet-type connection, or alternatively screwed onto bone engaging interface and wherein threaded configuration is provided on matching engagement surfaces of both crown abutment 5658 and bone engaging interface 5750.

In accordance with a preferred embodiment of the present invention as seen in FIG. 65B crown abutment 5659 is directly fixed into bone engaging interface of an implantable tooth implant assembly 5750 without an intermediary element such as fixture 5660. In accordance with a preferred embodiment of the present invention crown abutment 5658 is press fitted onto bone engaging interface, or alternatively snap fitted onto bone engaging interface, or alternatively snap fitted and press fitted onto bone engaging interface, or alternatively is mounted onto bone engaging interface by a bayonet-type connection, or alternatively screwed onto bone engaging interface and wherein threaded configuration is provided on matching engagement surfaces of both crown abutment 5658 and bone engaging interface 5750.

Still further in accordance with a preferred embodiment of the present invention, implantable tooth implant assembly 5650 is preferably implanted into a jaw bone by an implanter tool which is constructed and operative for performing the surgery by simpler and reduced number of stages of the operation. Grip ridge elements 5632 of bone engaging interface of an implantable tooth implant assembly 5750 are constructed operatively are constructed and operative in accordance with still another preferred embodiment of the present invention to be gripped by the jaws of an implanter tool which may be provided for the surgeon to perform the implanting of implantable dental implant 5600 or 5601 simultaneously with the bone engaging interface 5750 in one smooth easy-to-perform installation process. Although implanter tool suitable to operate in conjunction with grip ridge element 5632 is not shown, its function utilizing grip ridge element 5632 and the pliability of the interface 5750 is described hereinbelow.

In accordance with a preferred embodiment of the present invention preferably an implanter tool simultaneously grasps grip ridge elements 5632 and exerts stretching forces designated by numerals 5650 resultant of which is along the general direction of axis 5751 operating on ridge elements 5632 and exerting pushing forces designated by numerals 5652 resultant of which is along the general direction of axis 5751, operating on concave inner fixture anchoring surface 5752 bone engaging interface of an implantable tooth implant assembly 5750.

The simultaneous pushing forces 5652 operating on concave inner fixture anchoring surface 5752 are being exerted directly by an element of the implanter tool or alternatively by fixture 5660 as seen in FIG. 65A, or alternatively by crown abutment 5658 as seen in FIG. 65B and wherein any of elements of the implanter tool or fixture 5660 or crown abutment 5658 are placed inside bone engaging interface 5750 and grasped by the implanter tool. The simultaneous stretching and pushing operation stretches bone engaging interface of an implantable tooth implant assembly 5750 and allows easy insertion into the machined jaw bone following the simultaneous stretching and pushing operation.

In accordance with a preferred embodiment of the present invention, a surgeon using an implanter tool inserts into a suitably machined jaw bone the train comprised of implanter tool and a combination of elements of implantable tooth implant assembly 5650 and positioned for implanting. Following the placing described hereinabove the surgeon proceeds to operate the implanter to continuously change flexing and pushing forces until the implantable tooth implant assembly 5650 or assembly 5651 is properly installed by press fit onto bone engaging interface, or alternatively snap fitted onto bone engaging interface, or alternatively snap fitted and press fitted onto bone engaging interface.

Still further in accordance with a preferred embodiment of the present invention, preferably grip ridge elements such as grip ridge elements 5632 shown in FIG. 64A are formed and operative with an implanter tool as described hereinabove on any of implantable artificial sockets 5400 shown in FIGS. 60 61 62 and 63, and implantable artificial sockets 1100 shown hereinabove in FIG. 1 and socket 1200 shown hereinabove in FIG. 2 and socket 2100 shown hereinabove in FIG. 3 and sockets 2200 shown hereinabove in FIG. 4.

In accordance with a preferred embodiment of the present invention, a surgeon using an implanter tool implants into a suitably machined acetabulum bone the train comprised of implanter tool and any of socket 5400 shown in FIGS. 60 61 62 and 63, and implantable artificial sockets 1100 shown hereinabove in FIG. 1 and socket 1200 shown hereinabove in FIG. 2 and socket 2100 shown hereinabove in FIG. 3 and sockets 2200 shown hereinabove in FIG. 4 implanting any of said devices by press fit onto bone engaging interface, or alternatively snap fitted onto bone engaging interface, or alternatively snap fitted and press fitted onto bone engaging interface.

Reference is now made to FIG. 66 which is a partially cut away illustration of a bone engaging interface integrally formed with a gum embankment element of an implantable tooth implant assembly implanted in a suitable machined jaw bone 5684 constructed and operative in accordance with a preferred embodiment of the present invention; which is particularly suitable for use in a dental fixture and as an artificial periodontal ligament replacement.

As seen in FIG. 66 a bone engaging interface of an implantable dental implant, designated by reference numeral 5674 is configured and constructed similar to bone engaging interface 5750 as shown in FIG. 64A and extended therefrom outwardly and upwardly from rim 5678 a flexible gum embankment element 5680 constructed and operative to protect the gum 5682 following a surgery.

It is further appreciated that in preferred embodiments of implants described in FIGS. 64A, 64B, 65A, 65B and 66 hereinabove implants may be constructed with any of the following: Where the material of the bone interface element being more flexible than that of bone; Where bone interface element is shock-absorbing; and wherein bone interface has mechanical properties of mammalian cartilage; Where bone interface is more resilient that the jaw bone;

Where the abutment is formed with a plurality of portions having different mechanical properties; Where abutment comprises an outer shell and an inner core; wherein said artificial abutment is formed with a plurality of alternating adjacent first and second portions, said first portions being generally more rigid than said second portions and wherein bone-interface comprises at least two layers;

Reference is now made to FIGS. 74A, 75B, 75A, 75B, 76A, 76B, 77A, 77B, 78A and 78B, which are simplified meshed sectional illustrations of an artificial hip joint constructed and operative in accordance with preferred embodiments of the present invention, showing stress fields and associated strain fields produced and the force distributions produced by snap fit with press-fit installation of an implantable artificial socket 6100 of the type of implantable artificial socket 5400 shown in FIGS. 60, 61, 62 and 63, or of a similar type to implantable artificial sockets 1100 shown hereinabove in FIG. 1 and/or 1200 shown hereinabove in FIG. 2 and/or 2100 shown hereinabove in FIG. 3 and/or 2200 shown hereinabove in FIG. 4 or similar types are installed in a machined acetabulum in a situation where the dimensions and configuration of one or both of the implantable artificial socket and the machined acetabulum are such that both snap-fit and press-fit engagement are provided into a suitably machined natural acetabulum of a patient wherein bone engagement surface of implantable artificial socket engages machined surface of natural acetabulum. In alternative embodiments of the present invention convex bone engagement surfaces of artificial sockets described in FIGS. 74A, 75B, 75A, 75B, 76A, 76B, 77A, 77B, 78A and 78B hereinbelow are not configured with any configuration pattern.

In accordance with yet another preferred embodiment of the present invention convex bone engagement surfaces of artificial sockets described in FIGS. 74A, 75B, 75A, 75B, 76A, 76B, 77A, 77B, 78A and 78B hereinbelow are configured with a configuration pattern.

As described in FIG. 63 hereinabove it is appreciated by persons skilled in the art that with the stress field shown there is also an associated strain field and it is for purpose of clarity that only one type of field is shown here and the existed strain field is not shown.

It is a particular feature of the construction of implantable artificial socket constructed and operative in a hip join environment detailed in FIGS. FIGS. 74A, 75B, 75A, 75B, 76A, 76B, 77A, 77B, 78A and 78B controlling, as is described in FIG. 63 hereinabove, the stress and strain distribution within the substance of the surrounding bone, resulting in a positive bone remodeling, creating a mechanical environment with conditions that initiate net remodeling activity growing new bone cells of structural characteristics and targeting specific locations within the bone substance to be subjected to desired strain.

As illustrated in FIGS. 74A and 74B the stress fields produced and force distribution produced in a situation as mentioned hereinabove that both snap-fit and press-fit engagement are provided into a suitably machined natural acetabulum 6102 of a patient wherein bone engagement surface 6101 of implantable artificial socket 6100 engages machined surface 6103 of natural acetabulum 6102. The stress fields produced by the snap-fit and press-fit engagement are shown distributed within the substance of implantable artificial socket 6100 and within substantial regions of the substance of the bone of acetabulum 6102 and there exist also associated strain fields with in said regions of the substance of the bone of acetabulum 6102.

As a result an associated strain fields are created within substantial regions of the substance of the bone of acetabulum 6102 with strain magnitudes comparable to those found in bones of a physically active person. Said strain field activate bone growth and bone remodeling in said regions of the substance of the bone of acetabulum 6102 and enhance anchoring and adhesion of the prostheses to the bone.

A conventional artificial femoral head 6104 is mounted onto a conventional femoral stem in an orientation whereby an axis of symmetry 6112, of implantable artificial socket 6100, and an axis of symmetry 6114, of artificial femoral head 6104, are substantially aligned. A separation between the planes of outer edge 6122 of implantable artificial acetabulum socket 6100 and of outer edge 6124 of natural acetabulum 6102 along axis 6112 is created, as indicated by arrows 6126. FIGS. 74A and 74B illustrate a situation wherein the patient is not exerting any external force on the hip joint.

The snap-fit with press-fit installation, illustrated in FIG. 60, FIG. 61, FIG. 62 and FIG. 63, produces snap-fit engagement between protrusion 6132 and groove 6134, formed in natural acetabulum 6102, with pressure engagement between convex surface 6142 of protrusion 6132 and the concave surface 6144 of groove 6134. The snap-fit with press-fit installation also produces pressure engagement between concave surface 6146, of the machined acetabulum 6102, and the convex facing surface 6148, of artificial acetabulum socket 6100, generally along the entire extent thereof.

As further illustrated in FIG. 60, FIG. 61, FIG. 62 and FIG. 63, the above-described engagement of artificial acetabulum socket 6100 with the machined acetabulum 6102 causes deformation of artificial acetabulum socket 6100 and produces stressing in the acetabulum socket 6100, as illustrated, inter alia, by stress contour lines 6161 and 6162. The stresses and strains which occur within artificial acetabulum socket 6100, and the deformation of socket 6100 which is associated with these stresses and strains, transfer onto the surface 6146 of the machined acetabulum 6102 a distributed force pattern 6172, as seen in FIG. 74B.

In accordance with another preferred embodiment of the present invention the partially hemispherical convex bone engagement surface of the outer region 6174 of implantable artificial acetabulum socket 6100 is not configured with a configuration pattern and is not engaged by contact with any part of a bone or any apparatus on its outer surface 6176 so that outer edge 6122 of outer region 6174 is not constrained and is free to deform along axis 6112 in the situation of a snap-fit and press-fit engagement as indicated by the separation 6126 of outer edge 6122.

In accordance with yet another preferred embodiment of the present invention, the partially hemispherical convex bone engagement surface of the outer region 6174 of implantable artificial acetabulum socket 6100 is configured with a configuration pattern of types shown hereinabove in FIGS. 1 to 4. Bone remodeling process described hereinabove fixedly anchors the bone with the configuration pattern configured on the partially hemispherical convex bone engagement surface of the outer region 6174. The outer region 6174 of implantable artificial acetabulum socket 6100 is partially constrained and a reduced deformation occurs along axis 6112 compared to a situation described hereinabove wherein outer region 6174 of implantable artificial acetabulum socket 6100 is not configured with a configuration pattern and the said decreased deformation result in an improved fixation and longevity of implantable artificial acetabulum socket 6100.

As seen in FIG. 74B the distributed force pattern 6172 is characterized by a peak distributed force regions 6180, a medium distributed force region 6181 with distributed forces smaller than those of peak region 6180, a reduced force region 6182 and a reduced force region 6183 in proximity to outer region 6174 of natural acetabulum 6102 due to the freedom of outer region 6174 to deform.

As illustrated in FIGS. 75A and 75B a changed stress fields distributed within substantial regions of the bone substance of natural acetabulum 6102 and changed force pattern and deformations is resulted from loading of the joint by force indicated by numerals 6200 with respect to stress fields, distributed force pattern and deformation, as seen in FIGS. 74A and 74B. As it occurs in the life cycle of the joint loading the load force 6200 may be a static loading of a cyclic loading. The significance of cyclic strain field (resulting from cyclic loading) in bone and the regeneration of bone cells associated with said strain fields are detailed in FIG. 63 hereinabove. There is no expression in FIGS. 75A and 75B to eventual cyclic loading cases however it is appreciated by persons skilled in the art that the cyclic stress distribution exerted by cyclic load can be understood observing the static stress distribution as described in FIG. 75B and in 76A, 76B, 77A, 77B, 78A and 78B hereinbelow. And it is further understood as detailed in FIG. 63 hereinabove that there exist strain fields associated with said stress fields.

When the patient exerts an external force 6200 on the hip joint, the separation between the planes of outer edge 6122 of implantable artificial acetabulum socket 6100 and of outer edge 6124 of natural acetabulum 6102 along axis 6112, indicated by arrows 6202, is greater than that of separation 6126, shown in FIG. 74A, wherein the patient is not exerting any external force on the hip joint.

As seen in FIGS. 75A and 75B the combined action of above-described snap-fit with press-fit engagement with external force 6200 on the hip joint produce stresses in the acetabulum socket 6100, as illustrated, inter alia, by stress contour lines 6261, 6262, 6263 and 6264 which cover larger stressed area compared with those areas in the stressed acetabulum socket 6100, as shown in FIGS. 74A and 74B, and include regions with larger stresses than produced stresses in the acetabulum socket 6100, as illustrated, inter alia, by stress contour lines 6161 and 6162 as seen in FIG. 74A, and by stress contour lines 6271 and 6272, and 6273 which cover larger stressed area compared to the stressed natural acetabulum 6102, as shown in FIGS. 74A and 74B, and include regions with larger stresses than produced stresses in the natural acetabulum 6102, as illustrated, inter alia, by stress contour lines 6171 and 6172 as seen in FIG. 74A.

The stresses and strains which occur within artificial acetabulum socket 6100 and the deformation of socket 6100 which is associated with these stresses and strains transfer a distributed force pattern 6272 onto the surface 6146 of the machined acetabulum 6102, as illustrated in FIG. 75B.

The distributed force pattern 6272 is characterized by a reduced force region 6282 and a reduced force region 6283 in proximity to outer region 6174 of natural acetabulum 6102 due to the freedom of outer region 6174 to deform and a first peak force region 6284 and a second peak force region 6285 and a trough force region 6286. The distributed force pattern 6272 is of larger force magnitude that that of distributed force pattern 6172 shown for comparison as a dotted line in FIG. 75B.

The differences in the distributed force pattern 6272 for a loaded joint versus the force pattern 6172 of an unloaded socket 6100 installed in a snap-fit and press-fit engagement may vary as load 6200 varies. In the case of a very small load 6200 there will be very small variation of force patterns 6172 and 6272. This maybe the case for patients with limited mobility, as described in FIG. 63 hereinabove, and who are only capable of low level of activity. Socket 6100 is suitable or this type of patient very small variation between force patterns 6172 and 6272 are sustained for most of the patient's life and wherein no significant superimposed stresses exerted by external load resulting from the patient's level of activity are superimposed for any considerable periods of time of the patient's life.

In another preferred embodiment of the present invention implantable artificial socket 6100 is of type wherein the convex bone engagement surface is preferably configured with a partial configuration pattern on a very limited area of the convex bone engagement surface, or alternatively in another preferred embodiment of the present invention implantable artificial socket 5400 is of type wherein the convex bone engagement surface is preferably not configured with any configuration pattern.

As illustrated in FIGS. 76A and 76B a changed stress fields distributed within substantial regions of the bone substance of natural acetabulum 6402 and changed force pattern and deformations is resulted from loading of the joint by force indicated by numerals 6400 with respect to stress fields, distributed force pattern and deformation, as seen in FIGS. 75A and 75B.

FIGS. 76A and 76B show said joint constructed and operative in accordance with a preferred embodiment of the present invention, and showing stress fields distributed, force patterns and deformations resulting from loading of the joint incorporating an implantable artificial socket 6500 which is modified by variations in its thickness at various locations and/or preferable constructed with at least one additional layer. As seen in FIG. 76A artificial socket 6500 is constructed from three layers showing intermediate layer 6323, performing as a deformation control layer, preferably, molded of a polyurethane of durometer number 70 shore D and preferably, including carbon whiskers. Resulting from loading of the joint by force indicated by numerals 6400 modified stress fields distributed, force patterns and deformations are shown with respect to stress fields, distributed force pattern and deformation as seen in FIGS. 75A and 75B, wherein implantable artificial acetabulum socket 6100 is constructed with even thickness and of a unitary construction of one layer.

In the situation detailed in FIGS. 76A and 76B, the dimensions and configuration of one or both of the implantable artificial socket 6500 and the machined acetabulum are such that both snap-fit and press-fit engagement are provided into a suitably machined natural acetabulum 6302 of a patient, and a conventional artificial femoral head 6304 is mounted onto a conventional femoral stem in a matching orientation of both axis of symmetry 6112 of implantable artificial socket 6500 and axis of symmetry 6314 of artificial femoral head 6304 coincide, and wherein a separation between the planes of outer edge 6322 of implantable artificial acetabulum socket 6500 and of outer edge 6124 of natural acetabulum 6102 along axis 6112 is created, as indicated by arrows 6306.

The uneven thickness portion of artificial acetabulum socket 6500 comprises a region 6228 of a thickness less than the average thickness of uneven thickness portion and a region 6230 of a thickness greater than the average thickness of uneven thickness portion. This unique configuration produces variations of the stresses and strains which occur within artificial acetabulum socket 6500 and the deformation of socket 6500 which is associated with these stresses and strains transfer onto the surface 6446 of the machined acetabulum 6402 as a distributed force pattern 6472, as seen in FIG. 76B, compared to the stresses and strains which occurs within artificial acetabulum socket 6100 and the deformation of socket 6100 which is associated with these stresses and strains transfer onto the surface 6146 of the machined acetabulum 6102 detailed in FIG. 75A.

Thickness variations and or multi layer construction of socket 6500 produce stress variations in the natural acetabulum 6402 such that thicker portions of socket 6500 produce higher stress regions and thinner portions of socket 6500 produce lower stress regions.

As seen in FIGS. 76A and 76B, the distributed force pattern 6472 varies from distributed force pattern 6272 of FIGS. 75A and 75B, shown in FIG. 76B by a dotted line. When compared to distributed force pattern 6272, detailed in FIG. 75B, distributed force pattern 6472 is characterized by a first peak force region 6484 which is lower than that of the peak force region 6284 of distributed force pattern 6272 due to a lesser stressed region corresponding to the region 6228 of a thickness thinner than the average thickness of uneven thickness portion, and a trough force region 6386 which is larger than and a trough force region 6286 of distributed force pattern 6272 due to a lesser stressed region corresponding to the region 6230 of a thickness thicker than the average thickness of uneven thickness portion.

Distributed force pattern 6472 is also characterized by a second peak force region 6484 which is lower than that of the peak force region 6284 of distributed force pattern 6272 and by a reduced force region 6282 and a reduced force region 6283 in proximity to outer region 6174 of natural acetabulum 6102 due to the freedom of outer region 6174 to deform and a first peak force region 6284 and a second peak force region 6285.

The uneven thickness socket 6500 results in a distributed force pattern 6472, which describes a more even force distribution than that produced by socket 6100 configured of unitary construction with an even thickness.

Figure 77B:
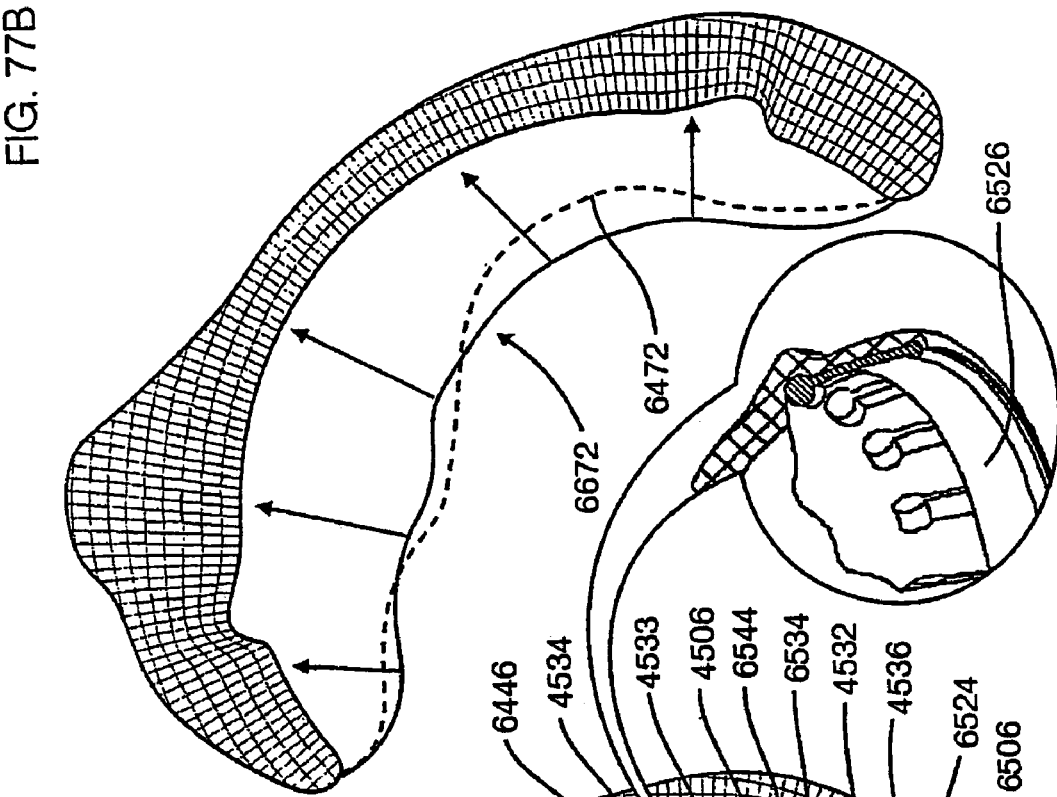
FIGS. 77A and 77B are simplified meshed sectional illustrations of an artificial hip joint constructed and operative in accordance with another preferred embodiment of the present invention, showing stress fields resulting from loading of the joint which are modified by provision of deformation control elements in the implantable artificial socket.
Figure 77A:
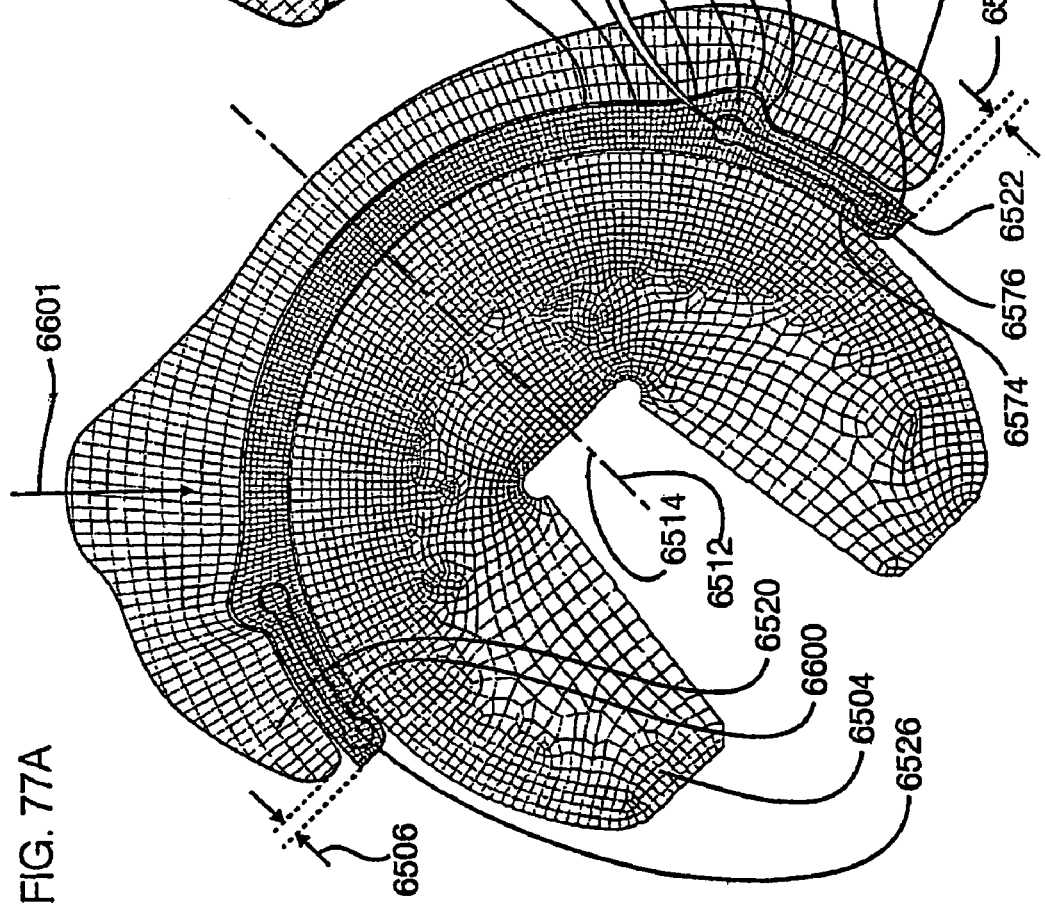
Figure 78B:
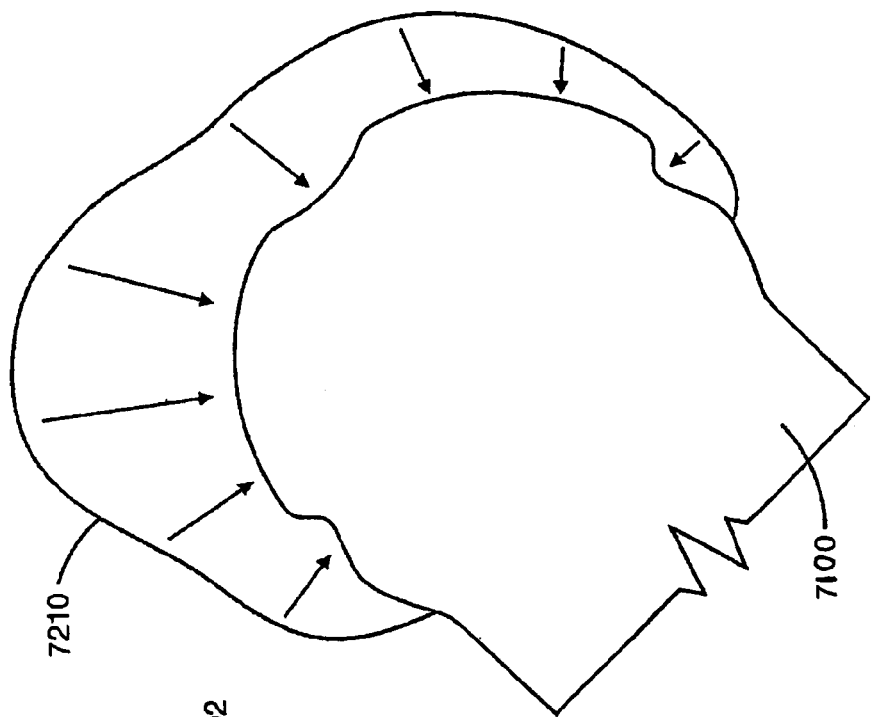
FIGS. 78A and 78B is a simplified meshed sectional illustration of an artificial hip joint constructed and operative in accordance with another preferred embodiment of the present invention, showing stress fields resulting from loading of the joint which are modified by provision of deformation control elements in an implantable artificial femoral head surface element formed on a femoral head articulating therewith.
Figure 78A:
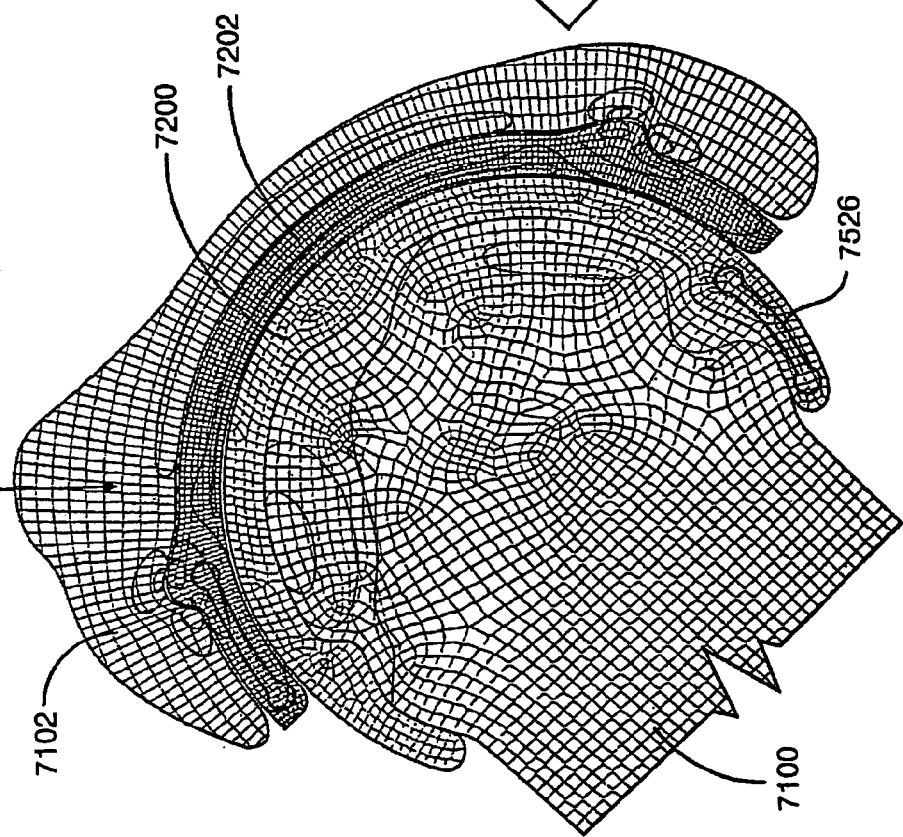

As illustrated in FIGS. 77A and 78A a changed stress fields distributed within substantial regions of the bone substance of natural acetabulum 6502 and changed force pattern and deformations is resulted from loading of the joint by force indicated by numerals 6601 with respect to stress fields, distributed force pattern and deformation, as seen in FIGS. 76A and 76B.

FIGS. 77A and 78A show said joint constructed and operative in accordance with a preferred embodiment of the present invention, and showing stress fields distributed, force patterns and deformations resulting from loading of the joint incorporating an implantable artificial socket 6600 which are modified by provision of deformation control element 6526 configured in the implantable artificial socket 6600.

In the situation detailed in FIGS. 77A and 78A the dimensions and configuration of one or both of the implantable artificial socket 6600 and the machined acetabulum are such that both snap-fit and press-fit engagement are provided into a suitably machined natural acetabulum 6502 of a patient, and a conventional artificial femoral head 6504 is mounted onto a conventional femoral stem in a matching orientation of both axis of symmetry 6512 of implantable artificial socket 6600 and axis of symmetry 6514 of artificial femoral head 6504 coincide, and wherein the separation between the planes of outer edge 6522 of implantable artificial acetabulum socket 6600 and of outer edge 6524 of natural acetabulum 6502 along axis 6512, indicated by arrows 6506.

The snap-fit with press-fit installation as seen in FIG. 60, FIG. 61, FIG. 62 and FIG. 63 produces snap-fit locking engagement between protrusion 6132 and groove 6134 formed in natural acetabulum 6502 with pressure engagement between convex surface 4533 of protrusion 4506 and the concave surface 6544 of groove 6534.

As seen in FIG. 65, a particular feature of the implantable artificial socket 6600 that it is constructed with deformation control element 6526 constructed in a similar manner to deformation control element 5776 in FIG. 64B, preferably, molded of a polyurethane of durometer number 70 shore D. Preferably, including carbon wiskers, of carbon woven fabric, or alternatively from other rigid material such as metal, high performance composite materials and the like. This unique construction of socket 6600 produces variations of the stresses and strains which occurs within artificial acetabulum socket 6600 and the deformation of socket 6600 which is associated with these stresses and strains transfer onto the surface 6446 of the machined acetabulum 6402 a distributed force pattern 6472 as seen in FIG. 78A compared to the stresses and strains which occurs within artificial acetabulum socket 6100 and the deformation of socket 6100 which is associated with these stresses and strains transfer onto the surface 6146 of the machined acetabulum 6102 detailed in FIG. 75A.

As seen in FIGS. 77A and 78A, the distributed force pattern 6572 varies from distributed force pattern 6172 shown in FIG. 75B by a dotted line. Distributed force pattern 6572 is mainly characterized by a reduced force region 6582 with a higher load than that of reduced force region 6282 of distributed force pattern 6272 and by a reduced force region 6583 in proximity to outer region 6574 of natural acetabulum 6502 with a higher load than that of reduced force region 6283 of distributed force pattern 6272 due to the restricted freedom of outer region 6574 to deform induced by deformation control element 6526. As deformation control element 6526 preferably, molded of a polyurethane of durometer number 70 shore D. Preferably, including carbon wiskers, of other rigid alternative constructions as detailed above, it is less flexible and it restrains the deformation of the entire socket 6300 along its tangential direction and in particular the deformation of its outer region 6574, first thickened portion 4534 of deformation control element 6526 is positioned within thickened portion inwards to protrusion 4506 of socket 6600. The surrounding molded material within the protrusion 4506 locks thickened portion 4534 from movement with reference to protrusion 4506. Protrusion 4506 is anchored within a matching machined groove 6134 formed in natural acetabulum 6502, and thus thickened portion 4534 is retrained from movement with reference to protrusion groove 6134 formed in natural acetabulum 6502.

As can be seen in FIG. 77A, the separation between the planes of outer edge 6522 of implantable artificial acetabulum socket 6600 and of outer edge 6524 of natural acetabulum 6502 along axis 6512, indicated by arrows 6506 is smaller than that of separation 6126 shown in FIG. 75A wherein there is no deformation control element such as deformation control element 6526 in socket 6100 of in socket 6500.

In the embodiments of this invention shown in FIGS. 74A, 75A and 76A the implantable artificial sockets 6100 or 6500 assembled unto machined natural acetabulum such as natural acetabulum 6102 are shown with bone engagement surfaces which are not formed with any configuration pattern such as the hexagonal configuration pattern 1110 shown in FIG. 1 hereinabove formed on convex bone engagement surface 1101 or such as the spiral configuration pattern 2110 shown in FIG. 3 hereinabove formed on convex bone engagement surface 2101 or configuration pattern shown in FIG. 4.

In other preferred embodiments of this invention bone engagement surfaces implantable artificial sockets 6100 or 6500 may be formed with suitable configuration patterns such as configuration patterns shown in FIGS. 1 to 4 hereinabove or any other suitable configuration pattern or alternatively may be preferably formed with any other none-smooth suitable surface textures.

As seen in FIGS. 77A and 77B, the distributed force pattern 6672 varies from distributed force pattern 6472 of FIGS. 76A and 76B, shown in FIG. 77B by a dotted line. When compared to distributed force pattern 6472, detailed in FIG. 76B, distributed force pattern 6672 is characterized by a more even force distribution than that produced by socket 6500 configured of FIG. 76A.

As described FIG. 63 hereinabove the outer surfaces of the prosthesis, as is the case in socket 6600 described in FIG. 77A, are comparable to the walls of said example pressurized container. Deformation control element 6526 operate in a manner a lid on a pressure container operates preventing pressure to escape from said container. In a similar manner Deformation control element 6526 prevent outward deformation to occur and thus seal the compression stresses within the outer surfaces of socket 6600.

As illustrated in FIGS. 78A and 78B the stress fields produced and force distribution produced in a situation wherein a snap-fit or both snap-fit and press-fit engagement of femoral head surface element 7200 are provided into a suitably machined natural femoral head 7100 and wherein a snap-fit or both snap-fit and press-fit engagement of a socket 7202 are provided into a suitably machined natural acetabulum 7102 of a patient operative in a hip joint environment and loaded by force 7000.

The stress fields produced due to loading 7000 by the engagement of both implants to respective bones are shown distributed within the substance of implants and artificial socket 7102 and femoral head 7100 and there exist also associated strain fields with in said regions of the substance of the femoral bone and the acetabulum bone. Femoral head surface element 7200 may be constructed in similar constructions of any of the implants shown hereinabove and in particular include deformation control element 7526.

It is a particular feature of the construction of implantable femoral head surface element 7200 constructed and operative in a hip join environment detailed in FIG. 78A controlling, as is described in FIG. 63 hereinabove, the stress and strain distribution within the substance of the surrounding femoral head bone, resulting in a positive bone remodeling, creating a mechanical environment with conditions that initiate net remodeling activity growing new bone cells of structural characteristics and targeting specific locations within the bone substance to be subjected to desired strain. The force distribution pattern on femoral head 7100 is designated by numeral 7210 and shown in FIG. 78B.

In accordance with yet another preferred embodiment of the present invention the implantable artificial socket for a joint also includes a bioactive coating. Preferably, the bioactive coating is formed by grit blasting. Alternatively, the bioactive coating is formed by spraying. In accordance with another preferred embodiment, the bioactive coating also includes an elastomer.

In accordance with yet another preferred embodiment of the present invention the implantable artificial femoral head resurfacing element also includes a bioactive coating. Preferably, the bioactive coating is formed by grit blasting. Alternatively, the bioactive coating is formed by spraying. In accordance with another preferred embodiment, the bioactive coating also includes an elastomer.

The surface roughness and surface porosity is provided preferably by co-spraying of an elastomer and bioactive materials composite coating. The premixed feedstock may be PU/HA (polyurethane/Hydroxylapatite), thus providing a co-spraying of PU/HA composite coating. The bioactive materials are preferably hydroxylapatite or any other suitable calcium phosphate-containing materials. These bioactive materials cause the contact surface of the artificial implantation device to become bioactive, stimulating bone growth to provide an adhesion of the implant to the bone and accelerate osteointegration.

The feedstock for this coating can be in powder form, where a combination of PU and HA powders are preferably blended in suitable ratios and sprayed to form the desired coating. Alternatively, the feedstock can be a PU rod that is co-sprayed with HA powder particles that are fed separately into the molten particle flow. The PU rod can also be extruded with HA powder mixed within it so that a composite rod feedstock is obtained. Alternatively, any other suitable method of combining the PU and the bioactive materials may be used. The rod will then be fed directly though the spray device and the resulting coating will contain both HA and PU particles forming the desired matrix.

In accordance with a preferred embodiment of the present invention a spraying apparatus is used, as described hereinabove, to modify the contact surface of the artificial implantation device by coating. This coating is preferably provided using a combustion process, which utilizes an oxygen-fuel mixture and heats the particles as they are fed through a gravity hopper through the center of the spraying apparatus. A nozzle directs the combustion gasses and the molten particles towards the contact surface of the artificial implantation device. The combustion of the gasses occurs within a chamber in the nozzle and a carrier gas is used to propel the molten particles forward, and prevent them from sticking to the nozzle walls. When using rod feedstock (in place of powder), atomizing gas is used to break the tip of the molten rod into discrete particles.

A coating of molten polyurethane particles can be applied to the contact surface of the artificial implantation device in order to create a rough porous surface into which the bone can grow. The process may start with a preheating step that is designed to melt the surface of the implant and provide for a chemical bond between the surface and the polyurethane particles, although the process can be applied to a cold surface as well. The thickness of the coating can be regulated.

The coating deposited using the above mentioned combustion spray process may be a Polymer-Hydroxylapatite composite coating. This coating system consists of a combination of polyurethane particles that will be co-sprayed with HA powder. The resulting coating will form a polymer scaffold like structure that will entrap the HA particles within. This composite structure will help anchor the implant by enabling bone attachment to the exposed HA particles and eventually bone interdigitation in the pores created as the HA resorbs with time.

Alternatively, a coating can be deposited onto the contact surface of artificial the implantation device by means of dipping, whereby a slurry is made of a polymer material, having a certain quantity of bioactive particles mixed within it The artificial implantation device is dipped into the slurry, after which it is allowed to dry. As the slurry dries, a composite polymer/bioactive material coating is created, where the bioactive particles are trapped within the polymer matrix.

The coating may be an elastomer on elastomer coating, such as a polyurethane on polyurethane coating. The polyurethane coating can have a hardness of 55D and upwards for enhancing bio-stability on the outer surface, while the artificial implantation device and contact surface is of hardness 80A.

In addition to the enhanced bone adhesion methods described herein, the contact surface of an artificial implantation device may also be treated using one of the following Surface Modification processes: Atomic cleaning, adhesion promotion, molecular grafting, cell attachment enhancement, and Plasma Enhanced Chemical Vapor Deposition (PECVD) coatings, such as implemented by the MetroLine Surface, Inc. Surface modification processes improve the articulating properties of the contact surface by reducing friction and thereby enhance the resistance to wear.

The following is a brief description of a best mode manufacturing process of the implantable artificial socket 1100 shown in FIGS. 1A to 1C. The manufacturing process typically comprises the steps as described hereinbelow. It is appreciated that the steps of the manufacturing process are monitored and controlled in order to assure the quality of the products meets the required standards.

Step 1. Material Identification:

A preferable material used for manufacturing a cup used for preparing the implantable artificial socket 1100 is Polycarbonate Urethane Bionate 80A, which is supplied by Polymer Technology Group Inc., 2810 7$^{th}$ Street, Berkeley, Calif. 94710, U.S.A.

Step 2. Equipment used for Cup Manufacturing:

Step 2.1. Equipment Use for Pre-Injection Drying:

A desiccant that has the ability to be connected directly to the screw of an injection molding machine and reach 50 deg dew point, is preferably used.

Step 2.2. Equipment Use for Cup Injection:

The injection molding machine includes computerized data acquisition ability and an 18-20 mm diameter cylinder, for example an ARBURG 4020 device.

Step 2.3. Equipment Use for Post-Injection Curing:

Industrial oven capable of maintaining 80° C.±2° C. for approximately 15 hours.

Step 3. Preprocess for the Raw Material:

The drying of the raw material is performed using a desiccant dehumidifier, outside of a clean room.

Step 3.1. The Drying Process Typically Includes the Steps:
I. 12 hours at 65° C. [−50 dew point]
II. 4 hours at 93° C. [−50 dew point]

The final product humidity should be preferably between 0.01%-0.02%.

Step 4. The Manufacturing Process:
1. Drying of the material for 16 hours by special drier (−50° C.) desiccant.
2. Direct transfer of the material in the drier to the injection machine, i.e. connecting a drier device directly to the machine.
3. Injection molding.
4. Curing in an oven for 16 hours.
5. Packaging.
6. Sterilization in Gamma.

Preferred polyurethane materials for use in the embodiments described hereinabove include the following materials.

The following materials are manufactured by POLYMER TECHNOLOGY GROUP PTG.

Bionate® polycarbonate-urethane is among the most extensively tested biomaterials ever developed. The Polymer Technology Group Incorporated acquired the license to manufacture this thermoplastic elastomer from Corvita Corporation (who marketed it under the name Corethane®) in 1996.

Carbonate linkages adjacent to hydrocarbon groups give this family of materials oxidative stability, making these polymers attractive in applications where oxidation is a potential mode of degradation, such as in pacemaker leads, ventricular assist devices, catheters, stents, and many other biomedical devices. Polycarbonate urethanes were the first biomedical polyurethanes promoted for their biostability.

Bionate® polycarbonate-urethane is a thermoplastic elastomer formed as the reaction product of a hydroxyl terminated polycarbonate, an aromatic diisocyanate, and a low molecular weightglycol used as a chain extender.

The scope of Bionate PCUs tests—encompassing Histology, Carcinogenicity, Biostability, and Tripartite Biocompatiblity Guidance for Medical Devices—reassures medical device and implant manufacturers of the material's biocompatibility. This allows biomaterials decision makers the ability to choose an efficacious biomaterial that will add to the cost-effectiveness of the development of their device or implant Below is a summary of the extensive biocompatibility testing conducted on Bionate PCUs, including its successful completion of a 2-year carcinogenicity study.

Copolymers of silicone with poplyurethanes:
PurSil™ Silicone Polyether Urethane
CarboSil™ Silicone Polycarbonate Urethane Silicones have long been known to be biostable and biocompatible in most implants, and also frequently have the low hardness and low modulus useful for many device applications. Conventional silicone elastomers can have very high ultimate elongations, but only low to moderate tensile strengths. Consequently, the toughness of most biomedical silicone elastomers is not particularly high. Another disadvantage of conventional silicone elastomers in device manufacturing is the need for cross-linking to develop useful properties. Once cross-linked, the resulting thermoset silicone cannot be redissolved or remelted.

In contrast, conventional polyurethane elastomers are generally thermoplastic with excellent physical properties. Thermoplastic urethane elastomers (TPUs) combine high elongation and high tensile strength to form tough, albeit fairly high-modulus elastomers. Aromatic polyether TPUs can have excellent flex life, tensile strength exceeding 5000 psi, and ultimate elongations greater than 700 percent. They are often used for continuously flexing, chronic implants such as ventricular-assist devices, intraaortic balloons, and artificial heart components. TPUs can easily be processed by melting or dissolving the polymer to fabricate it into useful shapes.

The prospect of combining the biocompatibility and biostability of conventional silicone elastomers with the processability and toughness of TPUs is an attractive approach to what would appear to be a nearly ideal biomaterial. For instance, it has been reported that silicone acts synergistically with both polycarbonate- and polyether-based polyurethanes to improve in vivo and in vitro stability. In polycarbonate-based polyurethanes, silicone copolymerization has been shown to reduce hydrolytic degradation of the carbonate linkage, whereas in polyether urethanes, the covalently bonded silicone seems to protect the polyether soft segment from oxidative degradation in vivo.

PTG synthesized and patented silicone-polyurethane copolymers by combining two previously reported methods: copolymerization of silicone (PSX) together with organic (non-silicone) soft segments into the polymer backbone, and the use of surface-modifying end groups to terminate the copolymer chains. Proprietary synthesis methods make high-volume manufacturing possible.

PurSil™ silicone-polyether-urethane and CarboSil™ silicone-polycarbonate-urethane are true thermoplastic copolymers containing silicone in the soft segment. These high-strength thermoplastic elastomers are prepared through a multi-step bulk synthesis where polydimethylsiloxane (PSX) is incorporated into the polymer soft segment with polytetramethyleneoxide (PTMO) (PurSil) or an aliphatic, hydroxyl-terminated polycarbonate (CarboSil). The hard segment consists of an aromatic diisocyanate, MDI, with a low molecular weight glycol chain extender. The copolymer chains are then terminated with silicone (or other) Surface-Modifying End Groups™. We also offer aliphatic (AL) versions of these materials, with a hard segment synthesized from an aliphatic diisocyanate.

Many of these silicone urethanes demonstrate previously unavailable combinations of physical properties. For example, aromatic silicone polyetherurethanes have a higher modulus at a given shore hardness than conventional polyether urethanes—the higher the silicone content, the higher the modulus (see PurSil Properties). Conversely, the aliphatic silicone polyetherurethanes have a very low modulus and a high ultimate elongation typical of silicone homopolymers or even natural rubber (see PurSil AL Properties). This makes them very attractive as high-performance substitutes for conventional cross-linked silicone rubber. In both the PTMO and PC families, certain polymers have tensile strengths three to five times higher than conventional silicone biomaterials.

Surface Modifying End Groups™ (SMEs) are surface-active oligomers covalently bonded to the base polymer during synthesis. SMEs—which include silicone (S), sulfonate (SO), fluorocarbon (F), polyethylene oxide (P), and hydrocarbon (H) groups-control surface chemistry without compromising the bulk properties of the polymer. The result is key surface properties, such as thromboresistance, biostability, and abrasion resistance, are permanently enhanced without additional post-fabrication treatments or topical coatings. This patented technology is applicable to a wide range of PTG's polymers.

SMEs provide a series of (biomedical) base polymers that can achieve a desired surface chemistry without the use of additives. Polyurethanes prepared according to PTG's development process couple endgroups to the backbone polymer during synthesis via a terminal isocyanate group, not a hard segment. The added mobility of endgroups relative to the backbone is thought to facilitate the formation of uniform overlayersby the surface-active (end) blocks. The use of the surface active endgroups leaves the original polymer backbone intact so the polymer retains strength and processability. The fact that essentially all polymer chains carry the surface-modifying moiety eliminates many of the potential problems associated with additives.

The SME approach also allows the incorporation of mixed endgroups into a single polymer. For example, the combination of hydrophobic and hydrophilic endgroups gives the polymer amphipathic characteristics in which the hydrophobic versus hydrophilic balance may be easily controlled.

The following Materials are manufactured by CARDIO-TECH CTE:

CHRONOFLEX®: Biodurable Polyurethane Elastomers are polycarbonate aromatic polyurethanes.

The ChronoFlex® family of medical-grade segmented polyurethane elastomers have been specifically developed by CardioTech International to overcome the in vivo formation of stress-induced microfissures.

HYDROTHANE™: Hydrophilic Thermoplastic Polyurethanes

HydroThane™ is a family of super-adsorbent, thermoplastic, polyurethane hydrogels, ranging in water content from 5 to 25% by weight, HydroThane™ is offered as a clear resin in durometer hardness of 80A and 93 Shore A.

The outstanding characteristic of this family of materials is the ability to rapidly absorb water, high tensile strength, and high elongation. The result is a polymer having some lubricious characteristics, as well as being inherently bacterial resistant due to their exceptionally high water content at the surface.

HydroThane™ hydrophilic polyurethane resins are thermoplastic hydrogels, and can be extruded or molded by conventional means. Traditional hydrogels on the other hand are thermosets and difficult to process.

The following materials are manufactured by THERMEDICS:

Tecothane® (aromatic polyether-based polyurethane), Carbothane® (aliphatic polycarbonate-based polyurethane), Tecophilic® (high moisture absorption aliphatic polyether-based polyurethane) and Tecoplast® (aromatic polyether-based polyurethane).

Polyurethanes are designated aromatic or aliphatic on the basis of the chemical nature of the diisocyanate component in their formulation. Tecoflex, Tecophilic and Carbothane resins are manufactured using the aliphatic compound, hydrogenated methylene diisocyanate (HMDI). Tecothane and Tecoplast resins use the aromatic compound methylene diisocyanate (MDI). AU the formulations, with the exception of Carbothane, are formulated using polytetramethylene ether glycol (PTMEG) and 1,4 butanediol chain extender. Carbothane is specifically formulated with a polycarbonate diol (PCDO).

These represent the major chemical composition differences among the various families. Aromatic and aliphatic polyurethanes share similar properties that make them outstanding materials for use in medical devices. In general, there is not much difference between medical grade aliphatic and aromatic polyurethanes with regard to the following chemical, mechanical and biological properties:

High tensile strength (4,000 10,000 psi)
High ultimate elongation (250 700%)
Wide range of durometer (72 Shore A to 84 Shore D)
Good biocompatibility
High abrasion resistance
Good hydrolytic stability
Can be sterilized with ethylene oxide and gamma irradiation
Retention of elastomeric properties at low temperature
Good melt processing characteristics for extrusion, injection molding, etc.

With such an impressive array of desirable features, it is no wonder that both aliphatic and aromatic polyurethanes have become increasingly the material of choice in the design of medical grade components. There are, however, distinct differences between these two families of polyurethane that could dictate the selection of one over the other for a particular application:

Yellowing

In their natural states, both aromatic and aliphatic polyurethanes are clear to very light yellow in color. Aromatics, however, can turn dark yellow to amber as a result of melt processing or sterilization, or even with age. Although the primary objection to the discoloration of aromatic clear tubing or injection molded parts is aesthetic, the yellowing, which is caused by the formation of a chromophore in the MDI portion of the polymer, does not appear to affect other physical properties of the material. Radiopaque grades of Tecothane also exhibit some discoloration during melt processing or sterilization. However, both standard and custom compounded radiopaque grades of Tecothane have been specifically formulated to minimize this discoloration Solvent Resistance Aromatic polyurethanes exhibit better resistance to organic solvents and oils than do aliphatics—especially as compared with low durometer (80 85 Shore A) aliphatics, where prolonged contact can lead to swelling of the polymer and short-term contact can lead to surface tackiness. While these effects become less noticeable at higher durometers, aromatics exhibit little or no sensitivity upon exposure to the common organic solvents used in the health care industry.

Softening at Body Temperature

Both aliphatic and aromatic polyether-based polyurethanes soften considerably within minutes of insertion in the body. Many device manufacturers promote this feature of their urethane products because of patient comfort advantage as well as the reduced risk of vascular trauma. However, this softening effect is less pronounced with aromatic resins than with aliphatic resins.

Melt Processing Temperatures

Tecothane, Tecoplast and Carbothane melt at temperatures considerably higher than Tecoflex and Tecophilic. Therefore, processing by either extrusion or injection molding puts more heat history into products manufactured from Tecothane, Tecoplast and Carbothane. For example, Tecoflex EG-80A and EG-60D resins mold at nozzle temperatures of approximately 310° F. and 340° F. respectively.

Tecothane and Carbothane products of equivalent durometers mold at nozzle temperatures in the range of 380° F. to 435° F.

Tecoflex®

A family of aliphatic, polyether-based TPU's. These resins are easy to process and do not yellow upon aging. Solution grade versions are candidates to replace latex.

Tecothane®

A family of aromatic, polyether-based TPUs available over a wide range of durometers, colors, and radiopacifiers. One can expect Tecothane resins to exhibit improved solvent resistance and biostability when compared with Tecoflex resins of equal durometers.

Carbothane®

A family of aliphatic, polycarbonate-based TPUs available over a wide range of durometers, colors, and radiopacifiers. This type of TPU has been reported to exhibit excellent oxidative stability, a property which may equate to excellent long-term biostability. This family, like Tecoflex, is easy to process and does not yellow upon aging.

Tecophilic®

A family of aliphatic, polyether-based TPU's which have been specially formulated to absorb equilibrium water contents of up to 150% of the weight of dry resin.

Tecogel, a new member to the Tecophilic family, is a hydrogel that can be formulated to absorb equilibrium water contents between 500% and 2000% of the weight of dry resin. The materials were designed as a coating cast from an ethanol/water solvent system.

Tecoplast®

A family of aromatic, polyether-based TPUs formulated to produce rugged injection molded components exhibiting high durometers and heat deflection temperatures.

Four families of polyurethanes, named Elast-Eon™, are available from AorTech Biomaterials.

Elast-Eon™ 1, a Polyhexamethylene oxide (PHMO), aromatic polyurethane, is an improvement on conventional polyurethane in that it has a reduced number of the susceptible chemical groups. Elast-Eon™ 2, a Siloxane based macrodiol, aromatic polyurethane, incorporates siloxane into the soft segment Elast-Eon™ 3, a Siloxane based macrodiol, modified hard segment, aromatic polyurethane, is a variation of Elast-Eon™ 2 with further enhanced flexibility due to incorporation of siloxane into the hard segment. Elast-Eon™ 4 is a modified aromatic hard segment polyurethane.

The following materials are manufactured by Bayer Corporation:

Texin 4210—Thermoplastic polyurethane/polycarbonate blend for injection molding and extrusion.

Texin 4215—Thermoplastic polyurethane/polycarbonate blend for injection molding and extrusion.

Texin 5250—Aromatic polyether-based medical grade with a Shore D hardness of approximately 50 for injection molding and extrusion. Complies with 21 CFR 177.1680 and 177.2600.

Texin 5286—Aromatic polyether-based medical grade with Shore A hardness of approximately 86 for injection molding or extrusion. Complies with 21 CFR 177.1680 and 177.2600.

Texin 5290—Aromatic polyether-based medical grade with a Shore A hardness of approximately 90. Complies with 21 CFR 177.1680 and 177.2600.

It is appreciated that the devices described hereinabove, while preferably formed by injection molding of polyurethane, may also be formed by any suitable manufacturing method and may be formed of any suitable medical grade elastomers. It is further appreciated that any of the following manufacturing methods may be utilized: injection molding including inserting inserts, compression molding including inserting inserts, injection—compression molding including inserting inserts, compression molding of prefabricated elements pre-formed by any of the above methods including inserting inserts, spraying including inserting inserts, dipping including inserting inserts, machining from stock or rods, machining from pre-fab elements including inserting inserts.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

It is appreciated that even though the illustrated embodiments hereinabove show specific prosthetic devices, the provision of configuration patterns described herein may also be applied to any prosthesis that includes a bone engagement surface.

It is a particular feature of preferred embodiments of the prostheses described hereinabove that the combination of their configuration with the mechanical properties of the pliable material from which they are formed promotes bone growth and bone remodeling, enhancing anchoring and adhesion of the prostheses to the bone. The mechanical properties of the pliable material are characterized by a non-linear stress strain relationship, such that when one region of the prosthesis is subject to loading, the prosthesis deforms in one or more regions, including regions not directly adjacent to the region subject to the loading. These deformations are associated with the fluid-like quality of the pliable material and are not found in rigid materials. The loading and the deformations within the prosthesis cause pressure exerted by the prosthesis onto the adjacent bone to be distributed in a manner similar to hydrostatic pressure generated by pressurized fluid within a container.

This results in the creation of strain fields in the bone adjacent to the prosthesis with strain magnitudes comparable to those found in bones of a physically active person. It is this strain field, which is created in substantial portions of the bone, that activates bone growth and bone remodeling simulating natural bone growth and remodeling.

The bone remodeling process, associated with preferred embodiments of the prostheses of the present invention, may be a continuous process throughout the life of the prostheses. As described hereinabove, the migration of bone cells into the channels or recesses proceeds gradually over time. As new bone cells fill in the voids defined between the recessed area of the prosthesis and the bone surface, new areas of contact are created between bone and the walls of the recessed area. These new contact areas are operative to participate regionally in the remodeling process described hereinabove.

The remodeling process contributes to the strengthening of the entire bone, including the new bone formed within the recessed areas. Even after the new bone cells fill the entire recess, the process of bone remodeling may continue through the entire bone contact surface.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. An implantable artificial joint prosthesis comprising:
   at least one joint defining element defining a bone-engaging surface, said bone-engaging surface including an anchoring mechanism operative for enhancing anchoring and adhesion of the joint defining element to the bone to enhance the stability and longevity of the prosthesis without the use of cement, wherein said bone-engaging surface is configured with a hexagonal configuration pattern, said hexagonal configuration pattern defined by a plurality of protruding hexagonal contact surface portions sized and shaped for direct contact with bone, each surrounded by a peripheral channel.

2. An implantable artificial joint prosthesis according to claim 1 and wherein said at least one joint defining element is formed of a material having mechanical properties which are characterized by a nonlinear stress strain relationship.

3. An implantable artificial joint prosthesis according to claim 1 and wherein said at least one joint defining element defines a generally hemispherical convex bone-engaging surface.

4. An implantable artificial joint prosthesis according to claim 3 and wherein said at least one bone engagement surface has formed thereon a generally annular outwardly extending protrusion.

5. An implantable artificial joint prosthesis according to claim 4 and wherein said protrusion defines a generally annular undercut.

6. An implantable artificial joint prosthesis according to any of the preceding claims and wherein said at least one bone-engaging surface is arranged for snap fit engagement with a bone.

7. An implantable artificial joint prosthesis according to any of claims 1, 2, 3, 4, or 5, wherein said at least one bone-engaging surface is arranged for press fit engagement with a bone.

8. An implantable artificial joint prosthesis according to claim 1 and wherein said channels are each defined by wall surfaces and a bottom surface.

9. An implantable artificial joint prosthesis according to claim 1 and wherein said channels are defined to provide an undercut engagement portion.

10. An implantable artificial joint prosthesis according to claim 8 and wherein said channels are defined to provide an undercut engagement portion.

11. An implantable artificial joint prosthesis according to claim 10 and wherein said undercut engagement portion comprises a relatively wider cross sectional dimension near said bottom surface and a relatively narrower cross sectional dimension away from said bottom surface.

12. An implantable acetabular prosthesis comprising:
an acetabular cup formed of a polymer having a non-linear stress-strain relationship, the acetabular cup having an outer surface and an opposing inner surface, the outer surface including a bone-engaging portion having a partially hemispherical convex shape including a plurality of recessed channels oriented to define a plurality hexagonal contact surfaces, the plurality of recessed channels having a dovetail shape defined by a bottom surface and opposing side surfaces extending at an oblique angle with respect to the bottom surface such that the opposing side surfaces are separated by a first distance at a first position adjacent the bottom surface and separated by a second distance, less than the first distance, at a second position spaced from the bottom surface.

13. The acetabular prosthesis of claim 12, wherein the outer surface further comprises an annular protrusion extending annularly around the outer surface of the acetabular cup between an apex of the acetabular cup and a rim of the acetabular cup.

14. The acetabular prosthesis of claim 13, wherein the annular protrusion defines an annular undercut.

15. The acetabular prosthesis of claim 14, wherein the annular protrusion is arranged for snap-fit engagement with a prepared portion of an acetabulum.

16. The acetabular prosthesis of claim 15, wherein the annular protrusion bounds the bone-engaging portion of the outer surface.

17. The acetabular prosthesis of claim 16, wherein the bone-engaging portion is positioned closer to the apex of the acetabular cup than the rim of the acetabular cup relative to the annular protrusion.

18. The acetabular prosthesis of claim 17, wherein the acetabular cup has a generally uniform thickness between the outer surface and the opposing inner surface.

19. The acetabular prosthesis of claim 18, wherein the acetabular cup is formed of an injection molded polyurethane.

20. An implantable acetabular cup comprising:
a body formed of a flexible polymer having a non-linear stress-strain relationship, the body having an outer surface and an opposing inner surface, the outer surface including a bone-engaging portion having a partially hemispherical convex shape including a plurality of bone contact portions bounded by a plurality of recessed channels, the plurality of recessed channels having a dovetail cross-section generally defined by a bottom surface and opposing side surfaces extending at an oblique angle with respect to the bottom surface such that the opposing side surfaces are separated by a first distance adjacent the bottom surface and are separated by a second distance, less than the first distance, adjacent the bone contact portions, wherein the body is configured for implantation into a prepared acetabulum without the use of cement such that at least the bone contact portions of the body directly contact the prepared acetabulum.

21. The implantable acetabular cup of claim 20, wherein the plurality of bone contact portions have a geometrical profile.

22. The implantable acetabular cup of claim 21, wherein the plurality of bone contact portions have a generally hexagonal profile.

23. The implantable acetabular cup of claim 20, wherein the outer surface further comprises an annular protrusion extending annularly around the outer surface of the body between an apex of the body and a rim of the body.

24. The acetabular prosthesis of claim 23, wherein the annular protrusion defines an annular undercut.

25. The acetabular prosthesis of claim 24, wherein the annular protrusion is arranged for snap-fit engagement with a prepared portion of an acetabulum.

26. The acetabular prosthesis of claim 25, wherein the annular protrusion bounds the bone-engaging portion of the outer surface.

27. The acetabular prosthesis of claim 26, wherein the bone-engaging portion is positioned closer to the apex of the acetabular cup than the rim of the acetabular cup relative to the annular protrusion.

28. An implantable acetabular cup comprising:
a body formed of a flexible polymer having a non-linear stress-strain relationship, the body having an outer surface and an opposing inner surface, the outer surface including a bone-engaging portion having a partially hemispherical convex shape including a plurality of bone contact portions bounded by a plurality of recessed channels, the plurality of recessed channels having a dovetail cross-section generally defined by a bottom surface and opposing side surfaces extending at an oblique angle with respect to the bottom surface such that the opposing side surfaces are separated by a first distance adjacent the bottom surface and are separated by a second distance, less than the first distance, adjacent the bone contact portions;

wherein at least the bone-engaging portion of the outer surface includes a bioactive coating.

29. The implantable acetabular cup of claim 28, wherein the bioactive coating comprises an elastomer.

* * * * *